US008883429B2

(12) United States Patent
Tomaskova et al.

(10) Patent No.: US 8,883,429 B2
(45) Date of Patent: Nov. 11, 2014

(54) VIRAL DIAGNOSTICS

(75) Inventors: Jana Tomaskova, Bratislava (SK); Juraj Kopacek, Bratislava (SK); Jaromir Pastorek, Bratislava (SK); Silvia Pastorekova, Bratislava (SK)

(73) Assignee: Bioscience Slovakia, Bratislava (SK)

( * ) Notice: Subject to any disclaimer, the term of this patent is extended or adjusted under 35 U.S.C. 154(b) by 0 days.

(21) Appl. No.: 13/345,334

(22) Filed: Jan. 6, 2012

(65) Prior Publication Data
US 2012/0237922 A1 Sep. 20, 2012

Related U.S. Application Data

(60) Provisional application No. 61/430,822, filed on Jan. 7, 2011.

(51) Int. Cl.
*G01N 33/53* (2006.01)
*A61K 39/395* (2006.01)
*C12N 5/02* (2006.01)
*A61K 39/42* (2006.01)
*C07K 16/10* (2006.01)
*G01N 33/569* (2006.01)
*C12Q 1/70* (2006.01)

(52) U.S. Cl.
CPC ............ *C12Q 1/701* (2013.01); *C07K 16/10* (2013.01); *G01N 33/56983* (2013.01)
USPC ... 435/7.1; 424/178.1; 424/130.1; 424/159.1; 435/325

(58) Field of Classification Search
USPC .......................................................... 435/5
See application file for complete search history.

(56) References Cited

PUBLICATIONS

Center for Disease Control (CDC), Lymphocytic Choriomeningitis Virus infection in organ transplant recipients—Massachusetts, Rhode Island, 2005, Morbidity and Mortality Weekly Report, 2005, 54(21):529-552.*
Ciurea et al., Persistence of lymphocytic choriomeningitis virus at very low levels in immune mice, 1999, PNAS, 96(21):11964-11969.*
International Search Report and Written Opinion; Tietze-Epoupa, Beatrix ; Oct. 25, 2012; World Intellectual Property Organization (WIPO) (International Bureau of); PCT/IB2012/000293; 18 pages.
Besselsen et al; Detection of lymphocytic choriomeningitis virus by use of fluorogenic nuclease reverse transcriptase-polymerase chain reaction analysis; Comparative Medicine; 2003; pp. 53(1):65-69.
Jamieson et al; Lymphocytic choriomeningitis virus: An emerging obstetric pathogen?; American Journal of Obstetrics and Gynecology; 2006; pp. 194:1532-1536.
McCausland et al; Quantitative PCR technique for detecting lymphocytic choriomeningitis virus in vivo; Journal of Virological Methods; 2007; pp. 147(1):167-176.
Invitation to Pay Additional Fees and, Where Applicable, Protest Fee; Tietze-Epoupa, Beatrix ; 2012; European Patent Office (EPO); PCT/IB2012/000293; 8 pages.
Tomaskova et al; Molecular characterization of the genes coding for glycoprotein and L protein of lymphocytic choriomeningitis virus strain MX; Virus Gen

VIRAL DIAGNOSTICS

RELATED APPLICATIONS

This application claims benefit of U.S. Provisional Application No. 61/430,822 filed Jan. 7, 2011, the entire content of which application is hereby expressly incorporated by reference herein in its entirety.

TECHNICAL FIELD

The present disclosure relates to compositions and methods for detecting viruses in subjects.

BACKGROUND

Compositions and methods for reliable detection and diagnosis of certain viruses are limited. Techniques for discriminating between acute and chronic viral infections are also limited and can be unreliable.

SUMMARY

The present disclosure provides compositions and methods for detecting lymphocytic choriomeningitis virus (LCMV) in subjects and/or for discriminating between acute and chronic LCMV infections. Accordingly, the present disclosure can be used, e.g., to identify LCMV and develop personalized therapies for the treatment of LCMV infection (e.g., to select subjects for LCMV antiviral therapy and to monitor and, if necessary, modify, LCMV antiviral therapy), reduce LCMV spread, reduce host-to-host LCMV transmission, reduce LCMV disease development and pathogenesis, and for evaluation of LCMV pathological states.

Accordingly, in one aspect, the disclosure provides a method for determining whether a subject is infected with lymphocytic choriomeningitis virus (LCMV), the method comprising: selecting a subject with increased susceptibility to LCMV infection; obtaining a sample from the subject; contacting the sample with one or more compositions for detecting LCMV; and determining whether the one or more compositions for detecting LCMV is associated with a marker of LCMV from the sample, wherein detection of an association indicates that that the subject is infected with LCMV.

In another aspect, the disclosure provides a method for determining whether a subject is infected with lymphocytic choriomeningitis virus (LCMV), the method comprising: selecting a subject suspected of being infected with LCMV; obtaining a sample from a subject; contacting the sample with one or more compositions for detecting LCMV; and determining whether the one or more compositions for detecting LCMV is associated with a marker of LCMV from the sample, wherein detection of an association indicates that the subject is infected with LCMV.

In still another aspect, the disclosure provides a method for determining whether a subject is infected with lymphocytic choriomeningitis virus (LCMV), the method comprising: obtaining a sample from a subject; contacting the sample with at least two compositions selected from the group consisting of: one or more probes or primers that bind specifically to one or more LCMV nucleic acids or a portion of one or more LCMV nucleic acids; one or more LCMV proteins or fragments thereof; and one or more compositions for detecting one or more LCMV peptides or LCMV peptide fragments (e.g., one or more antibodies or antibody fragments); and determining whether the two or more compositions are associated with a marker of LCMV from the sample, wherein detection of an association indicates that the subject is infected with LCMV.

In yet another aspect, the disclosure provides a method for determining whether a subject is infected with lymphocytic choriomeningitis virus (LCMV), the method comprising: selecting a subject experiencing or at risk for hypoxia; obtaining a sample from the subject: contacting the sample with one or more compositions for detecting LCMV; and determining whether the one or more compositions for detecting LCMV is associated with a marker of LCMV from the sample, wherein detection of an association indicates that the subject is infected with LCMV.

In some embodiments, the subject can be e.g., pregnant, immunocompromised, a transplant recipient, at risk for developing cancer, or having cancer, or any combination thereof. In some embodiments, the subject can be experiencing a hypoxic condition or at risk for a hypoxic condition.

In other embodiments, the one or more compositions for detecting LCMV can be one or more probes or primers that bind specifically to one or more LCMV nucleic acids or a portion of one or more LCMV nucleic acids.

In still other embodiments, the one or more compositions for detecting LCMV can be one or more LCMV proteins or fragments thereof.

In yet other embodiments, the one or more compositions for detecting LCMV can be one or more compositions for detecting one or more LCMV peptides or LCMV peptide fragments (e.g., one or more antibodies or antibody fragments).

In one aspect, the disclosure provides a composition comprising two or more compositions selected from the group consisting of: one or more probes or primers that bind specifically to one or more LCMV nucleic acids or a portion of one or more LCMV nucleic acids; one or more LCMV proteins or fragments thereof; and one or more compositions for detecting one or more LCMV peptides or LCMV peptide fragments (e.g., one or more antibodies or antibody fragments).

In another aspect, the disclosure provides a diagnostic kit, wherein the kit comprises: at least one isolated LCMV polypeptide or fragment thereof, e.g., an NP, GP, GPC, GP1, or ZP antigen, or fragment thereof. Alternatively or in addition, the kit can include at least one isolated antibody or antibody fragment that binds to an NP, GP, GPC, GP1, or ZP antigen, or antigen binding fragment thereof. Alternatively or in addition, the kit can include at least one probe or primer that binds specifically to one or more LCMV nucleic acids or a portion thereof, e.g., nucleic acids that encode NP, GP, GPC, GP1, or ZP antigens. In some instances, the kit can include any combination thereof.

In still another aspect, the disclosure provides a plurality of isolated polypeptides, wherein the plurality comprises or consists of at least two, e.g., three, four, or five, types of polypeptides, selected from the group consisting of isolated NP antigen or a fragment thereof, isolated GP antigen or a fragment thereof, isolated GPC antigen or a fragment thereof, isolated GP1 antigen or a fragment thereof, and isolated ZP antigen or a fragment thereof. In some instances, the disclosure provides a diagnostic kit comprising such a plurality of polypeptides.

In yet another aspect, the disclosure provides a plurality of isolated antibodies, e.g., monoclonal or polyclonal antibodies, wherein the plurality comprises or consists of antibodies that specifically bind to at least two, e.g., three, four, or five, types of polypeptides, selected from the group consisting of NP antigen or a fragment thereof, GP antigen or a fragment thereof, GPC antigen or a fragment thereof, GP1 antigen or a fragment thereof, and ZP antigen or a fragment thereof. In some instances, the disclosure provides a diagnostic kit comprising such a plurality of isolated antibodies.

In still another aspect, the disclosure provides a plurality of isolated nucleic acid probes or primers, wherein the plurality comprises or consists of probes or primers that specifically bind to nucleotide sequences that encode at least two, e.g., three, four, or five, types of polypeptides selected from the group consisting of NP antigen or a fragment thereof, GP antigen or a fragment thereof, GPC antigen or a fragment thereof, GP1 antigen or a fragment thereof, and ZP antigen or a fragment thereof. In some instances, the disclosure provides a diagnostic kit comprising such a plurality of probes or primers.

In some embodiments, a diagnostic kit described herein can further include an agent, e.g., an antiviral agent, for treating LCMV or a symptom thereof in a subject.

In yet another aspect, the disclosure provides a method of treating a subject for LCMV infection, comprising: obtaining a biological sample from a subject having or at risk for infection with LCMV; screening the sample using a diagnostic kit described above; a plurality of polypeptides described above; a plurality of antibodies described above; or the plurality of probes or primers described above; or any combination thereof; to determine whether the subject is infected with LCMV; and administering to the subject an agent, e.g., an antiviral agent, that treats LCMV or a symptom thereof if the patient is infected with LCMV. In some instances, the subject having or at risk for LCMV infection has a condition involving hypoxia. In some instances, the subject having or at risk for LCMV infection is pregnant, immunocompromised, a transplant recipient, at risk for developing cancer, or has cancer, or any combination thereof.

In still another aspect, the disclosure provides a method of determining whether a subject is infected with LCMV, the method comprising: obtaining a biological sample from a subject having or at risk for LCMV; contacting the sample with a plurality of polypeptides described above, a plurality of antibodies described above, or a plurality of probes or primers described above, or any combination thereof; determining whether the plurality of polypeptides, plurality of antibodies, plurality of probes or primers, or any combination thereof, associate with a marker of LCMV from the sample, wherein detection of an association indicates that the subject is infected with LCMV.

In another aspect, the disclosure provides a monoclonal antibody M59 that binds specifically to LCMV NP or antigen binding fragment thereof, e.g., a complementarity determining region (CDR), e.g., CDR3, thereof. In some instances, the disclosure provides a kit comprising such an antibody.

In another aspect, the disclosure provides a monoclonal antibody M87 that binds specifically to LCMV NP or antigen binding fragment thereof, e.g., a complementarity determining region (CDR), e.g., CDR3, thereof. In some instances, the disclosure provides a kit comprising such an antibody.

In another aspect, the disclosure provides a monoclonal antibody that binds specifically to LCMV GP1 or antigen binding fragment thereof, e.g., a complementarity determining region (CDR), e.g., CDR3, thereof. In some instances, the disclosure provides a kit comprising such an antibody.

In another aspect, the disclosure provides a monoclonal or polyclonal antibody that binds specifically to the amino acid sequence RSGWGWAGSDGKTT (SEQ ID NO:89), or an antigen binding fragment of such an antibody, e.g., a complementarity determining region (CDR), e.g., CDR3, thereof. In some instances, the disclosure provides a kit comprising such an antibody.

In another aspect, the disclosure provides a monoclonal antibody MJ3 that binds specifically to LCMV ZP or fragment thereof, e.g., a complementarity determining region (CDR), e.g., CDR3, thereof. In some instances, the disclosure provides a kit comprising such an antibody.

In some aspects, the disclosure provides methods of assessing (e.g., detecting, determining, evaluating, and/or monitoring) lymphocytic choriomeningitis virus (LCMV) infection or activity in a subject. Such methods can include selecting a subject for assessment, wherein candidate subjects have or are suspected of being exposed to LCMV or a LCMV infected person or animal. The methods also include obtaining or providing a sample from a selected subject, contacting the sample with one or more compositions for detecting LCMV, and determining whether the one or more compositions for detecting LCMV are associated with a marker of LCMV from the sample, wherein detection of an association indicates that that the subject is infected with LCMV.

In some aspects, the disclosure provides methods for assessing (e.g., detecting, determining, evaluating, and/or monitoring) lymphocytic choriomeningitis virus (LCMV), including levels (e.g., levels of LCMV nucleic acid, protein(s), and/or activity) in a subject, e.g., a subject infected with LCMV or that is suspected of being exposed to a source of LCMV infection, e.g., an LCMV infected human or animal. In some embodiments, such methods can include selecting a subject (e.g., a candidate subject), obtaining or providing a sample from the subject, contacting the sample with one or more compositions for detecting LCMV, and determining whether the one or more compositions for detecting LCMV is associated with a marker of LCMV from the sample, wherein detection of an association indicates that the subject is infected with LCMV.

In some aspects, the disclosure provides methods for assessing (e.g., detecting, determining, evaluating, and/or monitoring) lymphocytic choriomeningitis virus (LCMV), including levels (e.g., levels of LCMV nucleic acid, protein(s), and/or activity) in a subject, e.g., a subject infected with LCMV or that is suspected of being exposed to a source of LCMV infection, e.g., an LCMV infected human or animal. In some embodiments, methods include obtaining or providing a sample from a subject (e.g., a suitable subject), contacting the sample with at least two compositions selected from the group consisting of: one or more probes or primers that bind specifically to one or more LCMV nucleic acids or a portion of one or more LCMV nucleic acids; one or more LCMV proteins or fragments thereof; and one or more compositions for detecting one or more LCMV peptides or LCMV peptide fragments (e.g., one or more antibodies or antibody fragments); and determining whether the two or more compositions are associated with a marker of LCMV from the sample, wherein detection of an association indicates that the subject is infected with LCMV.

In some aspects, the disclosure provides methods for assessing (e.g., detecting, determining, evaluating, and/or monitoring) lymphocytic choriomeningitis virus (LCMV), including levels (e.g., levels of LCMV nucleic acid, protein(s), and/or activity) in a subject, e.g., a subject infected with LCMV or that is suspected of being exposed to a source of LCMV infection, e.g., an LCMV infected human or animal. In some embodiments, such methods can include, obtaining or providing a sample from the subject, contacting the sample with one or more compositions for detecting LCMV, and determining whether the one or more compositions for detecting LCMV is associated with a marker of LCMV from the sample, wherein detection of an association indicates that the subject is infected with LCMV.

In some embodiments, the methods of the disclosure can include selecting a subject that has or is at risk of a condition associated with an increased level of hypoxia and/or free radical formation. Such subjects include, for example, those that are pregnant, immunocompromised, transplant recipients, and/or that are at risk for developing cancer, or has cancer.

In some embodiments, the methods of the disclosure can include use of one or more compositions disclosed herein alone or in combination with any of the other compositions disclosed herein. For example, use of two or more compositions in combination is not limited to simultaneous use, but rather includes, for example, parallel use or subsequent use. In some embodiments, a result observed using one composition can be verified or confirmed using one or more of the other compositions disclosed herein.

In some embodiments, the methods of the disclosure can include use of one or more probes or primers that bind specifically to one or more LCMV nucleic acids or a portion of one or more LCMV nucleic acids. For example, such probes or primers can include nucleic acid probes or primers having 10 or more nucleic acids, wherein the 10 or more nucleic acids have at least at least 80% identity to one or more target regions within one or more of SEQ ID NOs:1-51, such that the one or more nucleic acid probes or primers bind specifically to the one or more target regions.

In some embodiments, the methods of the disclosure can include one or more probes or primers selected from the group consisting of one or more nucleic acid sequences with at least 80% identity to one or more of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73. In some embodiments, the methods of the disclosure can include one or more probes or primers selected from the group consisting of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73.

In some embodiments, the methods of the disclosure can include use of one or more probes or primers that bind to a nucleic acid encoding LCMV NP. For example, such probes or primers can include, SEQ ID NOs:58 and 59 or a pair of nucleic acid sequences with at least 80% identity to SEQ ID NOs:58 and 59; or SEQ ID NOs:66 and 67 or a pair of nucleic acid sequences with at least 80% identity to SEQ ID NOs:66 and 67.

In some embodiments, the methods of the disclosure can include use of one or more probes or primers that bind to a nucleic acid encoding LCMV GP. For example, such probes or primers can include SEQ ID NOs:60 and 61 or a pair of nucleic acid sequences with at least 80% identity to SEQ ID NOs:60 and 61; or SEQ ID NOs:68 and 69 or a pair of nucleic acid sequences with at least 80% identity to SEQ ID NOs:68 and 69.

In some embodiments, the methods of the disclosure can include use of one or more probes or primers that bind to a nucleic acid encoding LCMV ZP. For example, such probes or primers can include, SEQ ID NOs:62 and 63 or a pair of nucleic acid sequences with at least 80% identity to SEQ ID NOs:62 and 63; or SEQ ID NOs: 72 and 73 or a pair of nucleic acid sequences with at least 80% identity to SEQ ID NOs: 72 and 73.

In some embodiments, the methods of the disclosure can include use of one or more probes or primers that bind to a nucleic acid encoding LCMV L. For example, such probes or primers can include SEQ ID NOs: 70 and 71 or a pair of nucleic acid sequences with at least 80% identity to SEQ ID NOs: 70 and 71.

In some embodiments, the methods of the disclosure can include use of nucleic acids encoding two or more of LCMV NP, LCMV GP, LCMV ZP, and LCMV L.

In some embodiments, the methods of the disclosure can include use of SEQ ID NOs:58 and 59 or a pair of nucleic acid sequences with at least 80% identity to SEQ ID NOs:58 and 59, or SEQ ID NOs:66 and 67 or a pair of nucleic acid sequences with at least 80% identity to SEQ ID NOs:66 and 67, wherein the primers bind to LCMV NP; SEQ ID NOs:60 and 61 or a pair of nucleic acid sequences with at least 80% identity to SEQ ID NOs:60 and 61, or SEQ ID NOs:68 and 69 or a pair of nucleic acid sequences with at least 80% identity to SEQ ID NOs:68 and 69, wherein the primers bind to LCMV GP; SEQ ID NOs:62 and 63 or a pair of nucleic acid sequences with at least 80% identity to SEQ ID NOs:62 and 63, or SEQ ID NOs: 72 and 73 or a pair of nucleic acid sequences with at least 80% identity to SEQ ID NOs: 72 and 73, wherein the primers bind to LCMV ZP; or SEQ ID NOs: 70 and 71 or a pair of nucleic acid sequences with at least 80% identity to SEQ ID NOs: 70 and 71, wherein the primers bind to LCMV L.

In some embodiments, the methods of the disclosure can include use of one or more LCMV proteins or fragments thereof.

In some embodiments, the methods of the disclosure can include use of one or more antibodies or antibody fragments. In some embodiments, such antibodies or antibody fragments can include a monoclonal antibody having the same epitope specificity as hybridoma MJ3, LMBP accession number 9217CB, deposited with the Belgian Coordinated Collections of Microorganisms (BCCM) at Ghent University, Belgium. In some embodiments, such antibodies or antibody fragments can include a monoclonal antibody produced by hybridoma MJ3, LMBP accession number 9217CB, deposited with the Belgian Coordinated Collections of Microorganisms (BCCM) at Ghent University, Belgium. In some embodiments, such antibodies or antibody fragments can include a monoclonal antibody having the same epitope specificity as hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody produced by hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody having the same epitope specificity as hybridoma MJ3, LMBP accession number 9217CB, deposited with the Belgian Coordinated Collections of Microorganisms (BCCM) at Ghent University, Belgium, and a monoclonal antibody having the same epitope specificity as hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody produced by hybridoma MJ3, LMBP accession number 9217CB, deposited with the Belgian Coordinated Collections of Microorganisms (BCCM) at Ghent University, Belgium, and a monoclonal antibody produced by hybridoma M166, LMBP accession number 9216CB, deposited with the Belgian Coordinated Collections of Microorganisms (BCCM) at Ghent University, Belgium. In some embodiments, such antibodies or antibody fragments can include CDR3 (SEQ ID NO:78) of the heavy chain variable region of monoclonal antibody M87, comprising no (e.g., zero) or at least 1 (e.g., 1, 2, 3, 4, 5, less than 10, less than 20, less than 30, less than 50, or less than 100) conservative amino acid substitutions, and/or CDR2 (SEQ ID NO:77) of the heavy chain variable region of monoclonal antibody M87, comprising no (e.g., zero) or at least 1 (e.g., 1, 2, 3, 4, 5, less than 10, less than 20, less than 30, less than 50, or less than 100) conservative amino acid substitutions, and/or CDR1 (SEQ ID NO:76) of the heavy chain variable region of monoclonal antibody M87, comprising no (e.g., zero) or at least 1 (e.g., 1, 2, 3, 4, 5, less than 10, less than 20, less than 30, less than 50, or less than 100) conservative amino acid substitutions. In some embodiments, such antibodies or antibody fragments can include an antigen binding peptide (e.g., including an antibody and/or an antigen binding antibody fragment) with identity to SEQ ID NO: 74, wherein regions within the amino acid sequence that correspond to a complementarity determining region within SEQ ID NO:74 comprise one or more conservative amino acid substitutions, regions the amino acid sequence that correspond to a framework region within SEQ ID NO:74 have at least 80% identity to the corresponding region in SEQ ID NO:74, and/or the antigen binding peptide binds to LCMV NP.

In some aspects, the present disclosure includes compositions comprising combinations (e.g., including 1, 2 or 3) of: one or more probes or primers that bind specifically to one or more LCMV nucleic acids or a portion of one or more LCMV nucleic acids; one or more LCMV proteins or fragments thereof; and one or more antibodies or antibody fragments. In some embodiments, the one or more probes or primers of the compositions herein can include one or more nucleic acid probes or primers having 10 or more nucleic acids, wherein the 10 or more nucleic acids have at least at least 80% identity to one or more target regions within one or more of SEQ ID NOs:1-51, such that the one or more nucleic acid probes or primers bind specifically to the one or more target regions. In some embodiments, the one or more probes or primers of the compositions herein are selected from the group consisting of one or more nucleic acid sequences with at least 80% identity to one or more of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73. In some embodiments, the one or more probes or primers of the compositions herein are selected from the group consisting of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73. In some embodiments, the one or more probes or primers of the compositions herein include one or more probes or primers that bind to a nucleic acid encoding LCMV NP. In some embodiments, the one or more probes or primers of the compositions herein include one or more probes or primers selected from SEQ ID NOs:58 and 59 or a pair of nucleic acid sequences with at least 80% identity to SEQ ID NOs:58 and 59; or SEQ ID NOs:66 and 67 or a pair of nucleic acid sequences with at least 80% identity to SEQ ID NOs:66 and 67.

In some embodiments, the one or more probes or primers of the compositions herein include one or more probes or primers that bind to a nucleic acid encoding LCMV GP. For example, such probes or primers can include SEQ ID NOs:60 and 61 or a pair of nucleic acid sequences with at least 80% identity to SEQ ID NOs:60 and 61; or SEQ ID NOs:68 and 69 or a pair of nucleic acid sequences with at least 80% identity to SEQ ID NOs:68 and 69.

In some embodiments, the one or more probes or primers of the compositions herein include one or more probes or primers that bind to a nucleic acid encoding LCMV ZP. For example, such probes or primers can include SEQ ID NOs:62 and 63 or a pair of nucleic acid sequences with at least 80% identity to SEQ ID NOs:62 and 63; or SEQ ID NOs: 72 and 73 or a pair of nucleic acid sequences with at least 80% identity to SEQ ID NOs: 72 and 73.

In some embodiments, the one or more probes or primers of the compositions herein include one or more probes or primers that bind to a nucleic acid encoding LCMV L. For example, such probes or primers can include SEQ ID NOs: 70 and 71 or a pair of nucleic acid sequences with at least 80% identity to SEQ ID NOs: 70 and 71.

In some embodiments, the one or more probes or primers of the compositions herein include one or more probes or primers that bind to a nucleic acid encoding LCMV GP. For example, such probes or primers can include one or more probes or primers bind to nucleic acids encoding two or more of LCMV NP, LCMV GP, LCMV ZP, and/or LCMV L.

In some embodiments, the one or more probes or primers of the compositions herein include one or more probes or primers that bind to a nucleic acid encoding LCMV GP. For example, such probes or primers can include one or more probes or primers comprise: SEQ ID NOs:58 and 59 or a pair of nucleic acid sequences with at least 80% identity to SEQ ID NOs:58 and 59, or SEQ ID NOs:66 and 67 or a pair of nucleic acid sequences with at least 80% identity to SEQ ID NOs:66 and 67, wherein the primers bind to LCMV NP; SEQ ID NOs:60 and 61 or a pair of nucleic acid sequences with at least 80% identity to SEQ ID NOs:60 and 61, or SEQ ID NOs:68 and 69 or a pair of nucleic acid sequences with at least 80% identity to SEQ ID NOs:68 and 69, wherein the primers bind to LCMV GP; SEQ ID NOs:62 and 63 or a pair of nucleic acid sequences with at least 80% identity to SEQ ID NOs:62 and 63, or SEQ ID NOs: 72 and 73 or a pair of nucleic acid sequences with at least 80% identity to SEQ ID NOs: 72 and 73, wherein the primers bind to LCMV ZP; or SEQ ID NOs: 70 and 71 or a pair of nucleic acid sequences with at least 80% identity to SEQ ID NOs: 70 and 71, wherein the primers bind to LCMV L.

In some aspects, the present disclosure includes compositions comprising one or more antibodies. In some embodiments, such antibodies or antibody fragments can include a monoclonal antibody having the same epitope specificity as hybridoma MJ3, LMBP accession number 9217CB, deposited with the Belgian Coordinated Collections of Microorganisms (BCCM) at Ghent University, Belgium. In some embodiments, such antibodies or antibody fragments can include a monoclonal antibody produced by hybridoma MJ3, LMBP accession number 9217CB, deposited with the Belgian Coordinated Collections of Microorganisms (BCCM) at Ghent University, Belgium. In some embodiments, such antibodies or antibody fragments can include a monoclonal antibody having the same epitope specificity as hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody produced by hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody having the same epitope specificity as hybridoma MJ3, LMBP accession number 9217CB, deposited with the Belgian Coordinated Collections of Microorganisms (BCCM) at Ghent University, Belgium, and a monoclonal antibody having the same epitope specificity as hybridoma M166, LMBP accession number 9216CB, deposited with the Belgian Coordinated Collections of Microorganisms (BCCM) at Ghent University, Belgium. In some embodiments, such antibodies or antibody fragments can include a monoclonal antibody produced by hybridoma MJ3, LMBP accession number 9217CB, deposited with the Belgian Coordinated Collections of Microorganisms (BCCM) at Ghent University, Belgium, and a monoclonal antibody produced by hybridoma M166, LMBP accession number 9216CB, deposited with the Belgian Coordinated Collections of Microorganisms (BCCM) at Ghent University, Belgium. In some embodiments, such antibodies or antibody fragments can include CDR3 (SEQ ID NO:78) of the heavy chain variable region of monoclonal antibody M87, comprising one or more conservative amino acid substitutions, and/or CDR2 (SEQ ID NO:77) of the heavy chain variable region of monoclonal antibody M87, comprising one or more conservative amino acid substitutions, and/or CDR1 (SEQ ID NO:76) of the heavy chain variable region of monoclonal antibody M87, comprising one or more conservative amino acid substitutions.

In some embodiments, antibodies or antibody fragments included in the compositions of the disclosure can include CDR3 (SEQ ID NO:78) of the heavy chain variable region of monoclonal antibody M87, and/or CDR2 (SEQ ID NO:77) of the heavy chain variable region of monoclonal antibody M87, and/or CDR1 (SEQ ID NO:76) of the heavy chain variable region of monoclonal antibody M87.

In some embodiments, antibodies or antibody fragments included in the compositions of the disclosure can include an antigen binding peptide (e.g., including an antibody and/or antigen binding antibody fragment) with identity to SEQ ID NO: 74, wherein: regions within the amino acid sequence that correspond to a complementarity determining region within SEQ ID NO:74 comprise one or more conservative amino acid substitutions; regions the amino acid sequence that correspond to a framework region within SEQ ID NO:74 have at least 80% identity to the corresponding region in SEQ ID NO:74; and the antigen binding peptide binds to LCMV NP.

In some aspects, the present disclosure includes diagnostic kits. In some embodiments, such diagnostic kits can include, at least one isolated LCMV polypeptide or fragment thereof, wherein the LCMV polypeptide is an NP, GP, or ZP antigen, or fragment thereof; one or more isolated antibodies or antibody fragments that bind to an NP, GP, or ZP antigen, or antigen binding fragment thereof; and/or one or more probes or primers that bind specifically to one or more LCMV nucleic acids or a portion thereof; and/or combinations thereof.

In some embodiments, diagnostic kits of the present disclosure can include one or more probes or primers comprise one or more nucleic acid probes or primers having 10 or more nucleic acids, wherein the 10 or more nucleic acids have at least at least 80% identity to one or more target regions within one or more of SEQ ID NOs:1-51, such that the one or more nucleic acid probes or primers bind specifically to the one or more target regions. In some embodiments, probes or primers contained in the diagnostic kits of the present disclosure include probes or primers selected from the group consisting of one or more nucleic acid sequences with at least 80% identity to one or more of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73. In some embodiments, probes or primers contained in the diagnostic kits of the present disclosure include probes or primers selected from the group consisting of SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:68, SEQ ID NO:69, SEQ ID NO:70, SEQ ID NO:71, SEQ ID NO:72, SEQ ID NO:73.

In some embodiments, probes or primers contained in the diagnostic kits of the present disclosure include probes or primers that bind to a nucleic acid encoding LCMV NP. In some embodiments, such probes or primers can include, for example, SEQ ID NOs:58 and 59 or a pair of nucleic acid sequences with at least 80% identity to SEQ ID NOs:58 and 59; or SEQ ID NOs:66 and 67 or a pair of nucleic acid sequences with at least 80% identity to SEQ ID NOs:66 and 67.

In some embodiments, probes or primers contained in the diagnostic kits of the present disclosure include probes or primers that bind to a nucleic acid encoding LCMV GP. In some embodiments, such probes or primers can include, for example, SEQ ID NOs:60 and 61 or a pair of nucleic acid sequences with at least 80% identity to SEQ ID NOs:60 and 61; or SEQ ID NOs:68 and 69 or a pair of nucleic acid sequences with at least 80% identity to SEQ ID NOs:68 and 69.

In some embodiments, probes or primers contained in the diagnostic kits of the present disclosure include probes or primers that bind to a nucleic acid encoding LCMV ZP. In some embodiments, such probes or primers can include, for example, SEQ ID NOs:62 and 63 or a pair of nucleic acid sequences with at least 80% identity to SEQ ID NOs:62 and 63; or SEQ ID NOs: 72 and 73 or a pair of nucleic acid sequences with at least 80% identity to SEQ ID NOs: 72 and 73.

In some embodiments, probes or primers contained in the diagnostic kits of the present disclosure include probes or primers that bind to a nucleic acid encoding LCMV L. In some embodiments, such probes or primers can include, for example, SEQ ID NOs: 70 and 71 or a pair of nucleic acid sequences with at least 80% identity to SEQ ID NOs: 70 and 71.

In some embodiments, probes or primers contained in the diagnostic kits of the present disclosure include one or more probes or primers that bind to nucleic acids encoding two or more of LCMV NP, LCMV GP, LCMV ZP, and LCMV L.

In some embodiments, probes or primers contained in the diagnostic kits of the present disclosure include one or more of SEQ ID NOs:58 and 59 or a pair of nucleic acid sequences with at least 80% identity to SEQ ID NOs:58 and 59, or SEQ ID NOs:66 and 67 or a pair of nucleic acid sequences with at least 80% identity to SEQ ID NOs:66 and 67, wherein the primers bind to LCMV NP; SEQ ID NOs:60 and 61 or a pair of nucleic acid sequences with at least 80% identity to SEQ ID NOs:60 and 61, or SEQ ID NOs:68 and 69 or a pair of nucleic acid sequences with at least 80% identity to SEQ ID NOs:68 and 69, wherein the primers bind to LCMV GP; SEQ ID NOs:62 and 63 or a pair of nucleic acid sequences with at least 80% identity to SEQ ID NOs:62 and 63, or SEQ ID NOs: 72 and 73 or a pair of nucleic acid sequences with at least 80% identity to SEQ ID NOs: 72 and 73, wherein the primers bind to LCMV ZP; and/or SEQ ID NOs: 70 and 71 or a pair of nucleic acid sequences with at least 80% identity to SEQ ID NOs: 70 and 71, wherein the primers bind to LCMV L.

In some embodiments, diagnostic kits of the present disclosure include one or more isolated antibodies or antibody fragments. In some embodiments, isolated antibodies or antibody fragments included in the diagnostic kits of the present disclosure can include a monoclonal antibody having the same epitope specificity as hybridoma MJ3, LMBP accession number 9217CB, deposited with the Belgian Coordinated Collections of Microorganisms (BCCM) at Ghent University, Belgium. In some embodiments, isolated antibodies or antibody fragments included in the diagnostic kits of the present disclosure can include a monoclonal antibody produced by hybridoma MJ3, LMBP accession number 9217CB, deposited with the Belgian Coordinated Collections of Microorganisms (BCCM) at Ghent University, Belgium. In some embodiments, isolated antibodies or antibody fragments included in the diagnostic kits of the present disclosure can include a monoclonal antibody having the same epitope specificity as hybridoma M166, LMBP accession number 9216CB, deposited with the Belgian Coordinated Collections of Microorganisms (BCCM) at Ghent University, Belgium. In some embodiments, isolated antibodies or antibody fragments included in the diagnostic kits of the present disclosure can include a monoclonal antibody produced by hybridoma M166, LMBP accession number 9216CB, deposited with the Belgian Coordinated Collections of Microorganisms (BCCM) at Ghent University, Belgium. In some embodiments, isolated antibodies or antibody fragments included in the diagnostic kits of the present disclosure can include a monoclonal antibody having the same epitope specificity as hybridoma MJ3, LMBP accession number 9217CB, deposited with the Belgian Coordinated Collections of Microorganisms (BCCM) at Ghent University, Belgium, and a monoclonal antibody having the same epitope specificity as hybridoma M166, LMBP accession number 9216CB, deposited with the Belgian Coordinated Collections of Microorganisms (BCCM) at Ghent University, Belgium. In some embodiments, isolated antibodies or antibody fragments included in the diagnostic kits of the present disclosure can include a monoclonal antibody produced by hybridoma MJ3, LMBP accession number 9217CB, deposited with the Belgian Coordinated Collections of Microorganisms (BCCM) at Ghent University, Belgium, and a monoclonal antibody produced by hybridoma M166, LMBP accession number 9216CB, deposited with the Belgian Coordinated Collections of Microorganisms (BCCM) at Ghent University, Belgium.

In some embodiments, isolated antibodies or antibody fragments included in the diagnostic kits of the present disclosure can include CDR3 (SEQ ID NO:78) of the heavy chain variable region of monoclonal antibody M87, comprising one or more conservative amino acid substitutions, and/or CDR2 (SEQ ID NO:77) of the heavy chain variable region of monoclonal antibody M87, comprising one or more conservative amino acid substitutions, and/or CDR1 (SEQ ID NO:76) of the heavy chain variable region of monoclonal antibody M87, comprising one or more conservative amino acid substitutions.

In some embodiments, isolated antibodies or antibody fragments included in the diagnostic kits of the present disclosure can include CDR3 (SEQ ID NO:78) of the heavy chain variable region of monoclonal antibody M87, and/or CDR2 (SEQ ID NO:77) of the heavy chain variable region of monoclonal antibody M87, and/or CDR1 (SEQ ID NO:76) of the heavy chain variable region of monoclonal antibody M87.

In some embodiments, isolated antibodies or antibody fragments included in the diagnostic kits of the present disclosure can include an antigen binding peptide (e.g., an antibody or antigen binding antibody fragment) with identity to SEQ ID NO: 74, wherein: regions within the amino acid sequence that correspond to a complementarity determining region within SEQ ID NO:74 comprise one or more conservative amino acid substitutions; regions within the amino acid sequence that correspond to a framework region within SEQ ID NO:74 have at least 80% identity to the corresponding region in SEQ ID NO:74; and/or the antigen binding peptide binds to LCMV NP.

In some aspects, the present disclosure include pluralities of isolated polypeptides, wherein the plurality comprises at least two polypeptides selected from the group consisting of isolated NP antigen or a fragment thereof, isolated GP antigen or a fragment thereof, isolated GPC antigen or a fragment thereof, isolated GP1 antigen or a fragment thereof, and isolated ZP antigen or a fragment thereof. In some embodiments, pluralities of the disclosure can include: at least three polypeptides selected from the group consisting of isolated NP antigen or a fragment thereof, isolated GP antigen or a fragment thereof, isolated GPC antigen or a fragment thereof, isolated GP1 antigen or a fragment thereof, and isolated ZP antigen or a fragment thereof, at least four polypeptides selected from the group consisting of isolated NP antigen or a fragment thereof, isolated GP antigen or a fragment thereof, isolated GPC antigen or a fragment thereof, isolated GP1 antigen or a fragment thereof, and isolated ZP antigen or a fragment thereof, isolated NP antigen or a fragment thereof, isolated GP antigen or a fragment thereof, isolated GPC antigen or a fragment thereof, isolated GP1 antigen or a fragment thereof, and isolated ZP antigen or a fragment thereof. In some embodiments, such pluralities can be provided as or contained within a kit.

In some aspects, the present disclosure include pluralities of isolated antibodies or antibody fragments, wherein the plurality comprises antibodies or fragments that specifically bind to at least two polypeptides selected from the group consisting of NP antigen or a fragment thereof, GP antigen or a fragment thereof, GPC antigen or a fragment thereof, GP1 antigen or a fragment thereof, and ZP antigen or a fragment thereof.

In some aspects, the present disclosure include pluralities of isolated antibodies or antibody fragments, wherein the plurality comprises antibodies or fragments that specifically bind to at least three polypeptides selected from the group consisting of NP antigen or a fragment thereof, GP antigen or a fragment thereof, GPC antigen or a fragment thereof, GP1 antigen or a fragment thereof, and ZP antigen or a fragment thereof.

In some aspects, the present disclosure include pluralities of isolated antibodies or antibody fragments, wherein the plurality comprises antibodies or fragments that specifically bind to at least four polypeptides selected from the group consisting of NP antigen or a fragment thereof, GP antigen or a fragment thereof, GPC antigen or a fragment thereof, GP1 antigen or a fragment thereof, and ZP antigen or a fragment thereof.

In some aspects, the present disclosure include pluralities of isolated antibodies or antibody fragments, wherein the plurality comprises antibodies or fragments that specifically bind to NP antigen or a fragment thereof, GP antigen or a fragment thereof, GPC antigen or a fragment thereof, GP1 antigen or a fragment thereof, and ZP antigen or a fragment thereof.

In some embodiments, pluralities of the present disclosure can include a monoclonal antibody having the same epitope specificity as hybridoma MJ3, LMBP accession number 9217CB, deposited with the Belgian Coordinated Collections of Microorganisms (BCCM) at Ghent University, Belgium.

In some embodiments, pluralities of the present disclosure can include a monoclonal antibody produced by hybridoma MJ3, LMBP accession number 9217CB, deposited with the Belgian Coordinated Collections of Microorganisms (BCCM) at Ghent University, Belgium. In some embodiments, pluralities of the present disclosure can include a monoclonal antibody having the same epitope specificity as hybridoma M166, LMBP accession number 9216CB, deposited with the Belgian Coordinated Collections of Microorganisms (BCCM) at Ghent University, Belgium. In some embodiments, pluralities of the present disclosure can include a monoclonal antibody produced by hybridoma M166, LMBP accession number 9216CB. In some embodiments, pluralities of the present disclosure can include a monoclonal antibody having the same epitope specificity as hybridoma MJ3, LMBP accession number 9217CB, deposited with the Belgian Coordinated Collections of Microorganisms (BCCM) at Ghent University, Belgium, and a monoclonal antibody having the same epitope specificity as hybridoma M166, LMBP accession number 9216CB, deposited with the Belgian Coordinated Collections of Microorganisms (BCCM) at Ghent University, Belgium. In some embodiments, pluralities of the present disclosure can include a monoclonal antibody produced by hybridoma MJ3, LMBP accession number 9217CB, deposited with Belgian Coordinated Collections of Microorganisms (BCCM) at Ghent University, Belgium, and a monoclonal antibody produced by hybridoma M166, LMBP accession number 9216CB, deposited with Belgian Coordinated Collections of Microorganisms (BCCM) at Ghent University, Belgium.

In some embodiments, pluralities of the present disclosure can include an antigen binding peptide with identity to SEQ ID NO: 74, wherein: regions within the amino acid sequence that correspond to a complementarity determining region within SEQ ID NO:74 comprise one or more conservative amino acid substitutions; regions the amino acid sequence that correspond to a framework region within SEQ ID NO:74 have at least 80% identity to the corresponding region in SEQ ID NO:74; and/or the antigen binding peptide binds to LCMV NP.

In some aspects, the pluralities of the present disclosure can be provided as (e.g., sold, offered for sale, marketed, shipped, stored, and/or packaged) or contained within a diagnostic kit.

In some aspects, pluralities of the present disclosure can include probes or primers that specifically bind to nucleotide sequences that encode at least two polypeptides selected from the group consisting of NP antigen or a fragment thereof, GP antigen or a fragment thereof, GPC antigen or a fragment thereof, GP1 antigen or a fragment thereof, and ZP antigen or a fragment thereof. In some embodiments, pluralities of the present disclosure can include probes or primers that specifically bind to nucleotide sequences that encode at least three polypeptides selected from the group consisting of NP antigen or a fragment thereof, GP antigen or a fragment thereof, GPC antigen or a fragment thereof, GP1 antigen or a fragment thereof, and ZP antigen or a fragment thereof. In some embodiments, pluralities of the present disclosure can include probes or primers that specifically bind to nucleotide sequences that encode at least four polypeptides selected from the group consisting of NP antigen or a fragment thereof, GP antigen or a fragment thereof, GPC antigen or a fragment thereof, GP1 antigen or a fragment thereof, and ZP antigen or a fragment thereof. In some embodiments, pluralities of the present disclosure can include probes or primers that specifically bind to nucleotide sequences that encode NP antigen or a fragment thereof, GP antigen or a fragment thereof, GPC antigen or a fragment thereof, GP1 antigen or a fragment thereof, and ZP antigen or a fragment thereof.

In some aspects, the pluralities of the present disclosure can be provided as (e.g., sold, offered for sale, marketed, shipped, stored, and/or packaged) or contained within a diagnostic kit. In some embodiments, such diagnostic kits can further include at least one (e.g., 1 2, 3, 4, 5 or more) agent (e.g., a pharmaceutical) for treating LCMV or a symptom thereof in a subject. In some embodiments, at least one such agent is an antiviral agent.

In some embodiments, the present disclosure provides methods of treating a subjects for LCMV infection, comprising: obtaining a biological sample from a subject having or at risk for infection with LCMV; screening the sample using the method of claim 1 to determine whether the subject is infected with LCMV; and administering to the subject an agent that treats LCMV or a symptom thereof if the patient is infected with LCMV. In some embodiments, treatment methods of the present disclosure can include selecting a subject with or at risk for LCMV infection has a condition involving hypoxia. Such subjects can include, for example, those that are pregnant, immunocompromised, transplant recipients, and those at risk for developing cancer, or with cancer.

In some aspects, the present disclosure provides a monoclonal antibody M59 that binds specifically to LCMV NP or fragment thereof.

In some aspects, the present disclosure provides a monoclonal antibody M87 that binds specifically to LCMV NP or fragment thereof.

In some aspects, the present disclosure provides a monoclonal antibody that binds specifically to LCMV GP1 or fragment thereof.

In some aspects, the present disclosure provides a monoclonal antibody that binds specifically to the amino acid sequence RSGWGWAGSDGKTT (SEQ ID NO:89).

In some aspects, the present disclosure provides a monoclonal antibody MJ3 that binds specifically to LCMV ZP or fragment thereof.

In some aspects, the present disclosure provides an antigen binding fragment of one or more of the antibodies disclosed herein.

In some aspects, the present disclosure provides a complementarity determining region (CDR) of one or more of the antibodies disclosed herein. In some embodiments, the CDR is CDR3.

In some aspects, one or more of the antibodies or antibody binding fragments disclosed herein can be provided as (e.g., sold, offered for sale, marketed, shipped, stored, and/or packaged) or contained within a kit.

In some aspects, the present disclosure provides a monoclonal antibody having the same epitope specificity as hybridoma MJ3, LMBP accession number 9217CB, deposited with Belgian Coordinated Collections of Microorganisms (BCCM) at Ghent University, Belgium.

In some aspects, the present disclosure provides a monoclonal antibody produced by hybridoma MJ3, LMBP accession number 9217CB, deposited with Belgian Coordinated Collections of Microorganisms (BCCM) at Ghent University, Belgium.

In some aspects, the present disclosure provides a cell of hybridoma MJ3, LMBP accession number 9217CB, deposited with Belgian Coordinated Collections of Microorganisms (BCCM) at Ghent University, Belgium.

In some aspects, the present disclosure provides a monoclonal antibody having the same epitope specificity as hybridoma M166, LMBP accession number 9216CB, deposited with Belgian Coordinated Collections of Microorganisms (BCCM) at Ghent University, Belgium.

In some aspects, the present disclosure provides a monoclonal antibody produced by hybridoma M166, LMBP accession number 9216CB, deposited with Belgian Coordinated Collections of Microorganisms (BCCM) at Ghent University, Belgium.

In some aspects, the present disclosure provides a cell of hybridoma M166, LMBP accession number 9216CB, deposited with Belgian Coordinated Collections of Microorganisms (BCCM) at Ghent University, Belgium.

In some aspects, the present disclosure provides an isolated antibody or antibody fragment comprising CDR3 (SEQ ID NO:78) of the heavy chain variable region of monoclonal antibody M87, comprising one or more conservative amino acid substitutions, and/or CDR2 (SEQ ID NO:77) of the heavy chain variable region of monoclonal antibody M87, comprising one or more conservative amino acid substitutions, and/or CDR1 (SEQ ID NO:76) of the heavy chain variable region of monoclonal antibody M87, comprising one or more conservative amino acid substitutions.

In some aspects, the present disclosure provides an isolated antibody or antibody fragment comprising CDR3 (SEQ ID NO:78) of the heavy chain variable region of monoclonal antibody M87, and/or CDR2 (SEQ ID NO:77) of the heavy chain variable region of monoclonal antibody M87, and/or CDR1 (SEQ ID NO:76) of the heavy chain variable region of monoclonal antibody M87.

In some aspects, the present disclosure provides an antigen binding peptide (e.g., an antibody or antibody fragment) with identity to SEQ ID NO: 74, wherein: regions within the amino acid sequence that correspond to a complementarity determining region within SEQ ID NO:74 comprise one or more conservative amino acid substitutions; regions the amino acid sequence that correspond to a framework region within SEQ ID NO:74 have at least 80% identity to the corresponding region in SEQ ID NO:74; and the antigen binding peptide binds to LCMV NP.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is an illustration showing the structure of LCMV, including the outer trans-membrane glycoproteins 1 and 2 (GP1 and GP2), Z protein, NP, RNA, and L protein of LCMV virion and virus replication strategy.

FIG. 1B is a schematic illustrating the LCMV life cycle.

FIG. 2 (i.e., FIG. 2i-2vi) shows alignments of nucleotide sequences for the NP genomic region on S segment of selected LCMV strains/isolates.

FIG. 3 (i.e., FIG. 3i-3vi) shows alignments of nucleotide sequences for the GP (i.e. GPC, encompassing GP1 and GP2) genomic region on S segment of selected LCMV strains/isolates.

FIG. 4 shows alignments of nucleotide sequences for the ZP genomic region on L segment of selected LCMV strains/isolates.

FIG. 5 (i.e., FIGS. 5i-5ii) shows alignment of amino acid sequences for NP antigens of selected LCMV strains/isolates.

FIG. 6 (i.e., FIGS. 6i-6ii) shows alignment of amino acid sequences for GP antigens of selected LCMV strains/isolates.

FIG. 7 shows alignment of amino acid sequences for ZP antigens of selected LCMV strains/isolates.

FIG. 14 is an image showing immunohistochemical detection of viral NP in kidney tumor (A) and a negative control (B).

DETAILED DESCRIPTION

Figures 8A, 8B, 8C, 8D:
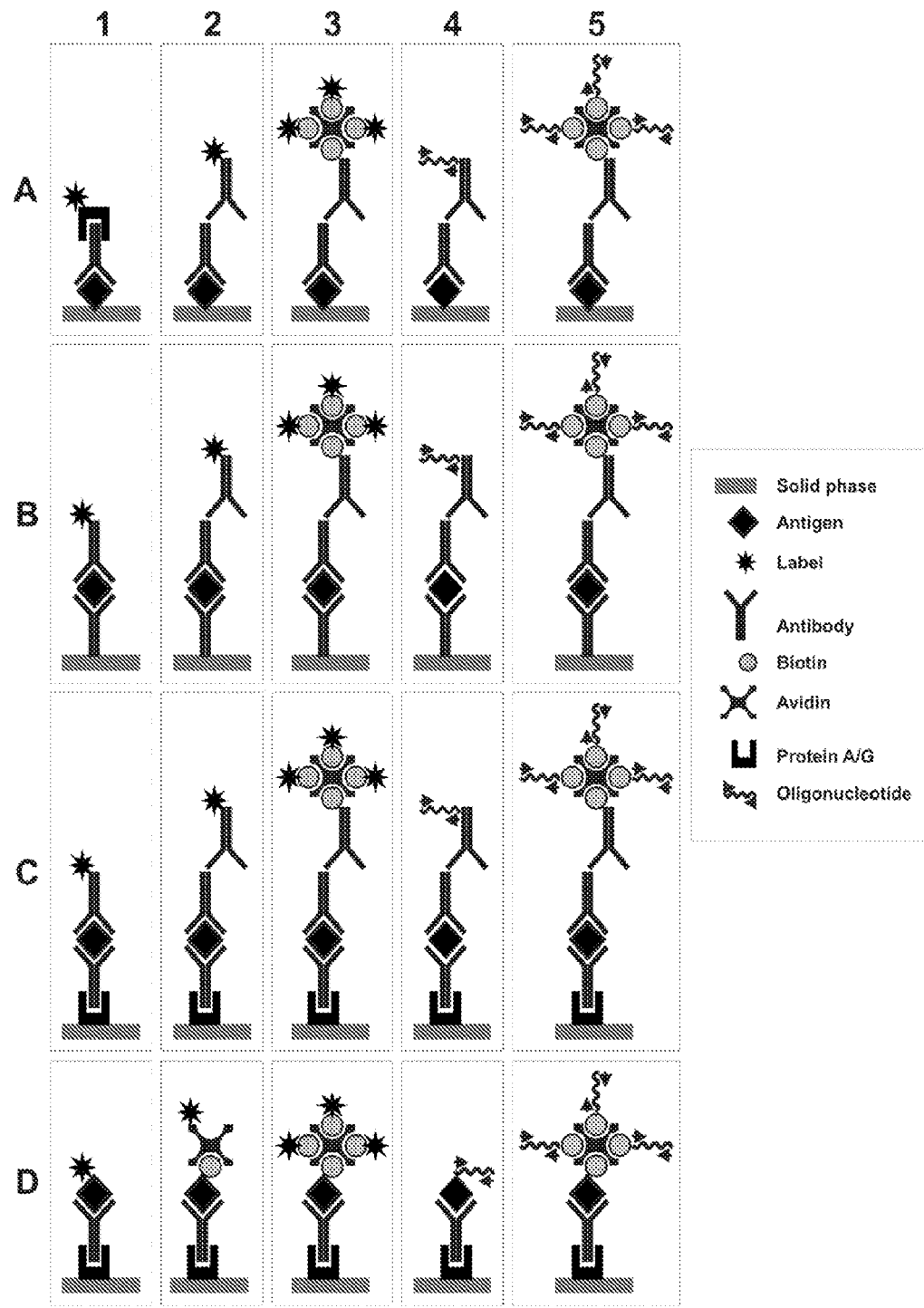
FIGS. 8A-8D are illustrations showing exemplary antibody based assays for use in the methods disclosed herein.

The present disclosure is based, inter alia, on the surprising discovery LCMV in persistence can be reactivated by hypoxia. Such viral reactivation can manifest clinically, e.g., in vulnerable subjects that include, but are not limited to, e.g., pregnant subjects, immunocompromised subjects, transplant recipients, and subjects at risk for developing or with cancer. Accordingly, the present disclosure provides compositions and methods for reliably detecting LCMV, e.g., reactivated LCMV.

Figures 1A, 1B:
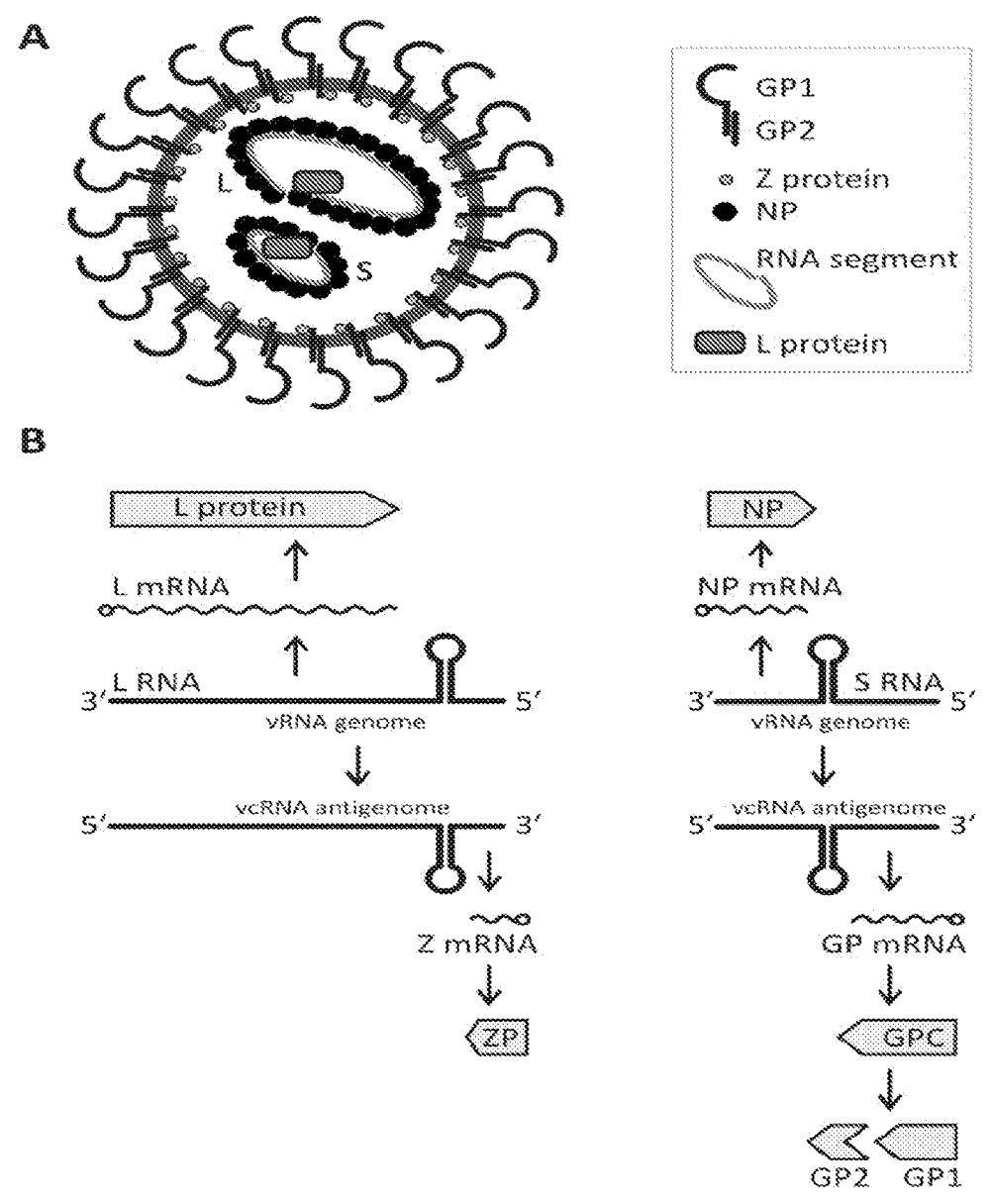

Lymphocytic choriomeningitis virus (LCMV) is a prototypic member of Arenaviridae family with enveloped virion and bisegmented single-stranded RNA genome (see FIG. 1). Both segments (small [S] and large [L]) contain two open reading frames in mutually opposite orientations and utilize an ambisense coding strategy (Meyer et al, 2002). The S RNA encodes a major viral protein nucleoprotein (NP) and a glycoprotein precursor (GP-C), which is co-translationally cleaved into peripheral glycoprotein 1 (GP1) and transmembrane glycoprotein 2 (GP2) (Southern et al, Virology, 157(1): 145-55 (1987)). The L RNA segment encodes an RNA-dependent RNA polymerase (L) and a regulatory ring finger Z protein (ZP) (Buchmeier Curr Top Microbiol Immunol. 262: 159-73 (2002); Salvato, Virology 173, 1-10 (1989)).

Virus replication starts with the L polymerase-driven transcription of the 3' RNA genome arms of negative polarity and produces mRNAs that are subsequently translated to NP and L polymerase. These viral proteins assist in the transcription of the RNA genome to virus cRNA, serving as a template for the synthesis of the new genomic RNA molecules as well as for the subgenomic mRNAs translated to GPC and ZP. This two-stage replication strategy facilitates establishment of virus persistence, which can be sustained by the virus ribonucleoprotein composed of NP, the RNA genome, and L polymerase in the absence of mature virion production caused by absent or limited expression of glycoproteins (van der Zeijst et al, J Virol 48:249-61 (1983); Buchmeier, 2003).

LCMV can easily set up persistent infection in a wide variety of cell types derived from various species, where it does not perturb vital cell functions but modulates nonessential phenotypic features (Oldstone, Curr Top Microbiol Immunol. 263:83-117 (2002); Peters et al, Supra).

LCMV is distributed worldwide due to its association with rodents of the species *Mus musculus*. Humans are generally infected through the respiratory tract after direct or indirect contact with infected rodents or pets (via inhalation of virus-contaminated aerosols of animal saliva, urine, and feces). In immunocompetent individuals, LCMV causes illnesses varying from mild flu-like symptoms to rare severe encephalitis (Jahrling and Peters, 1992, Buchmeier et al, 2007). Infection with this virus during pregnancy has been linked to spontaneous abortions and malformations (Jamieson et al, 2006, Meritet et al, 2009). More strikingly, fatal cases of LCMV infections transmitted via transplanted organs from infected donors to immunosuppressed recipients were recently reported and call for more attention to this seemingly innocent virus (Fischer et al, 2006, Amman et al, 2007).

Acute infections involve production of mature GP1 and GP2, whereas chronic/persistent infection exhibits production of immature GPC, but mature forms of glycoproteins are missing or reduced, NP is produced both in acute and chronic/persistent situations, similarly ZP is produced both in acute and chronic/persistent situations, but its expression increases upon reactivation by hypoxia (Buchmeier, 2003, Tomaskova et al, unpublished data). This fact was overlooked in previous attempts to detect LCMV, but was recalled recently by our research data showing relative increase of GP, NP and ZP production and formation of infectious virions in response to hypoxia, which is associated with many physiological and pathological situations, including embryonic development, heart and brain ischemia, cancer etc. Moreover, LCMV "reactivation" is known to occur due to immunosuppression (for transplantation purposes, due to chemotherapy and in other situations) and is also likely to be associated with increased expression of viral GP, NP and ZP.

So far, no reliable method for LCMV detection, screening and diagnosis of LCMV acute and/or chronic infection is available for routine use in clinical laboratories, no target (risk) populations to be screened/diagnosed have been determined, since comprehensive epidemiological data is missing. Existing assays (including, for example, immunofluorescence, ELISA, complement-fixation, and RT PCR assays) do not show sufficient sensitivity and reproducibility, do not discriminate between acute and chronic/persistent infection, and are applied only occasionally in outbreak situations or when other viruses cannot be detected. Furthermore, existing assays generally do not combine NP, GP, ZP (or alternatively GCP and GP1) and ZP-derived oligonucleotides or polypeptides to detect virus and/or virus-specific antibodies and thus most probably fail to detect many cases of LCMV infections even when the infection is proven otherwise. Therefore, availability of an accurate, sensitive and reproducible routine assay is highly desirable.

Compositions for Detecting LCMV

Compositions encompassed by the present disclosure include biological and synthetic materials that can specifically detect one or more markers of LCMV in a biological sample.

Figure 3I:
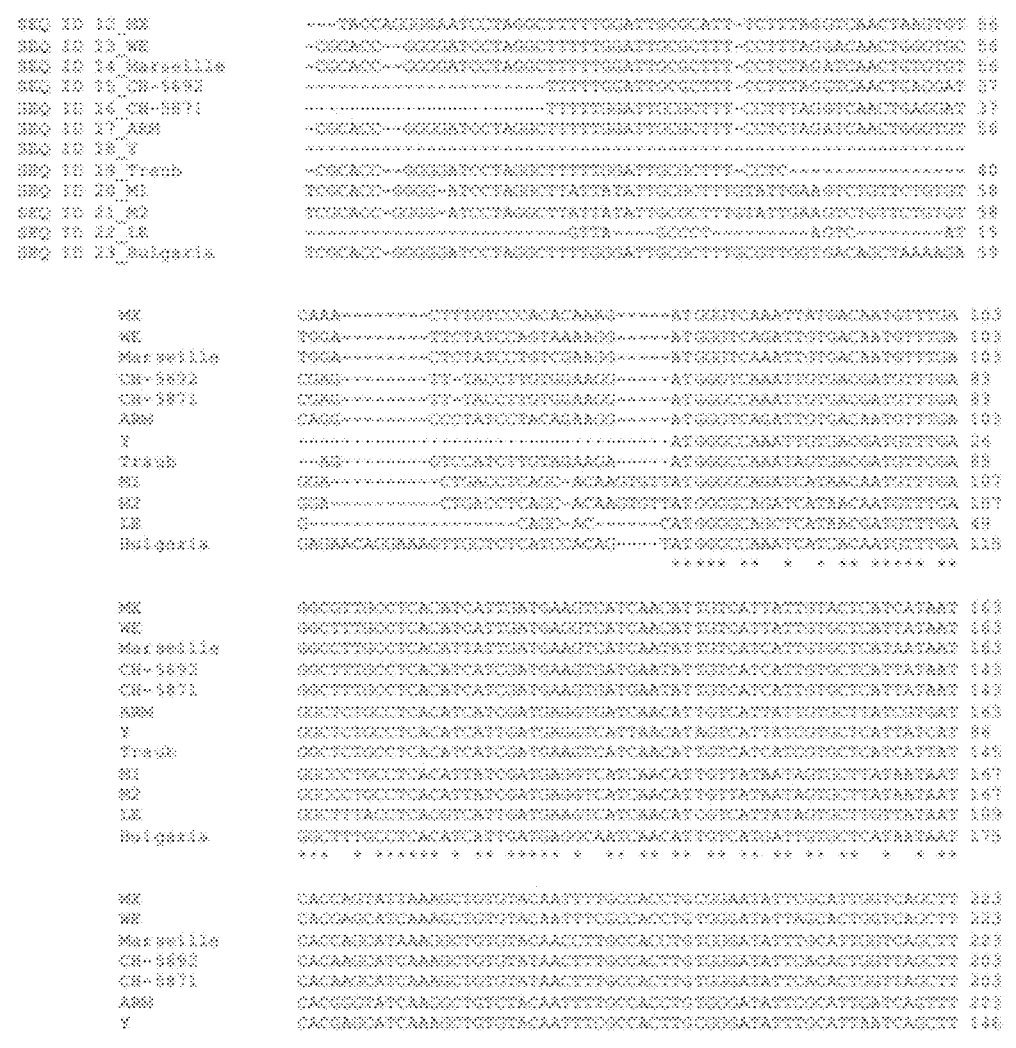
Figure 3:
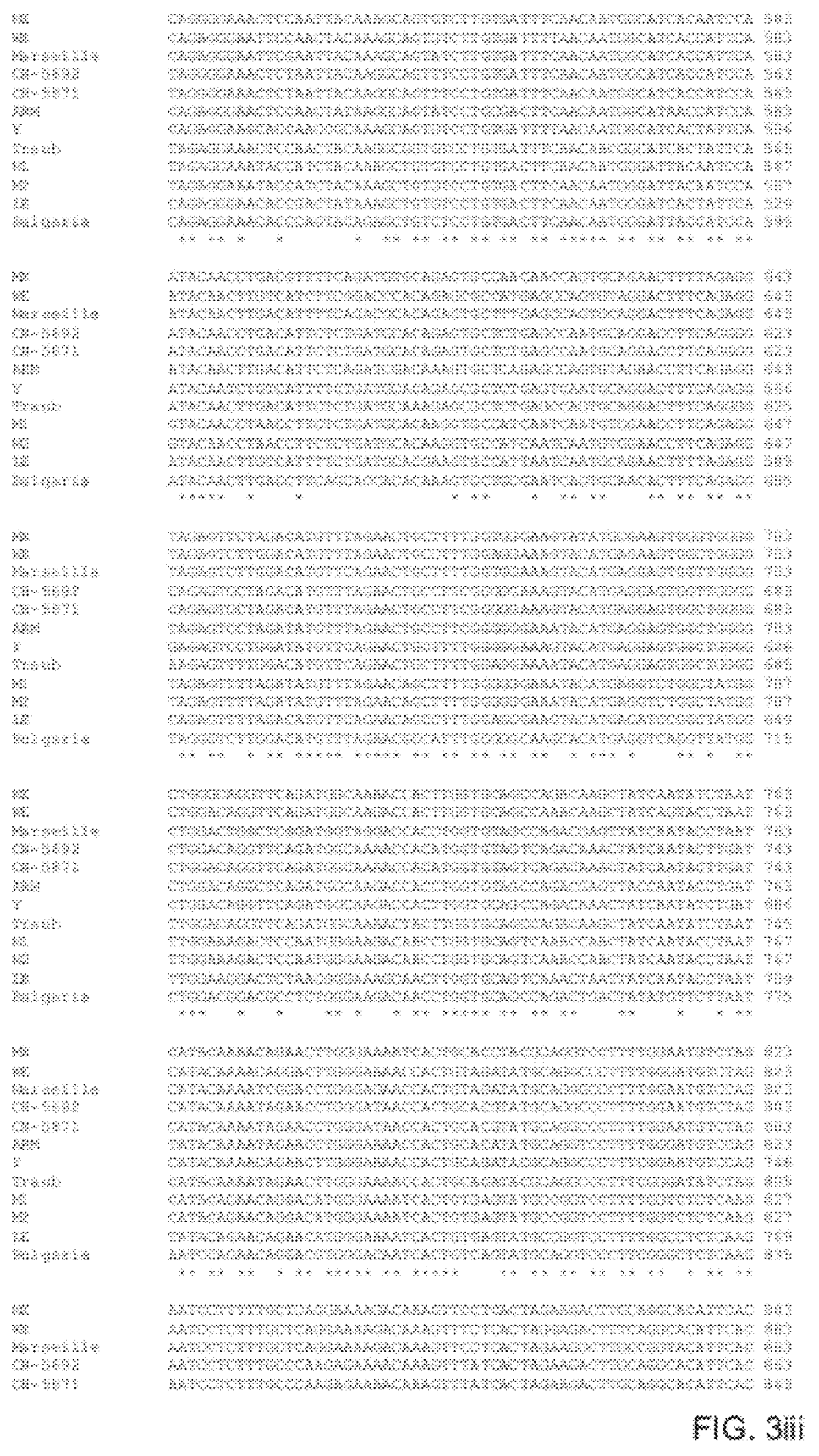
Figure 3V:
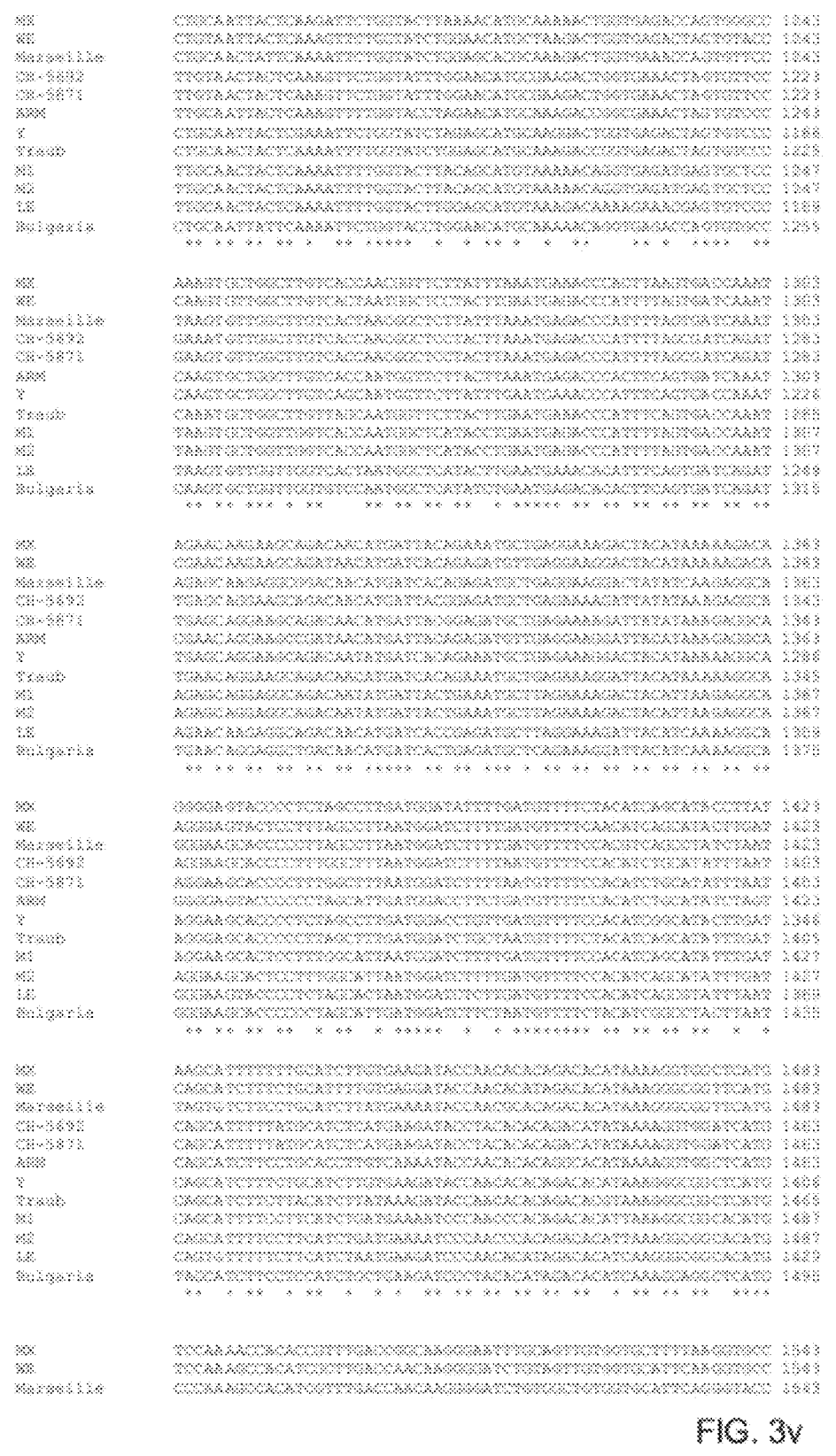
Figure 4:
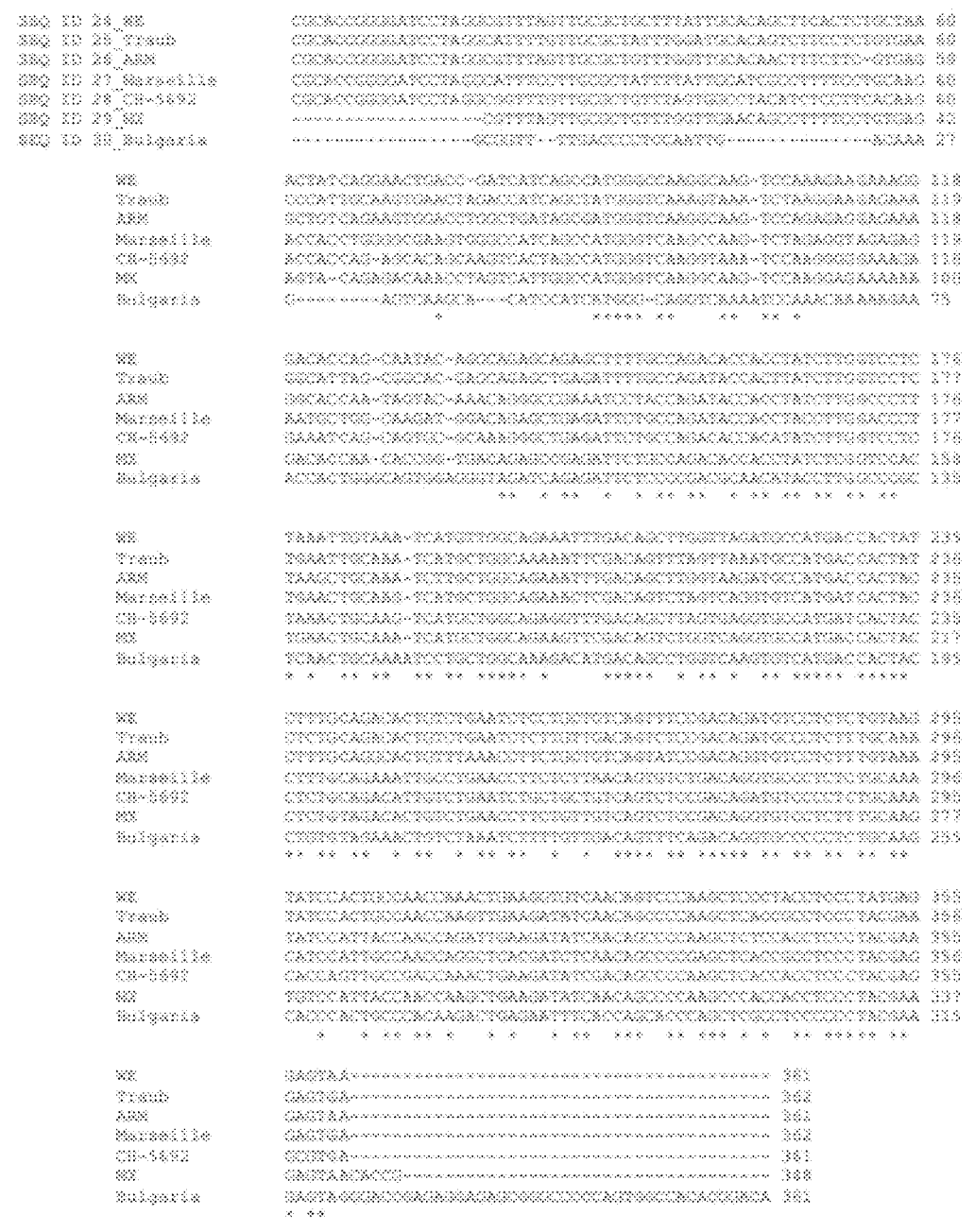

Markers of LCMV can include, for example, one or more or at least one (e.g., 1, 2, 3, 4, 5 or more, including combinations of 2, 3, 4, or 5) LCMV nucleic acids (e.g., LCMV mRNA and/or LCMV genomic DNA/RNA such as LCMV encoding one or more LCMV peptides (e.g., LCMV GP (1 and/or 2), Z protein, NP, and/or L protein)) and/or LCMV proteins or peptides (e.g., e.g., 1, 2, 3, 4, 5 or more, including combinations of 2, 3, 4, or 5 of LCMV GP (1 and/or 2), Z protein, NP, and/or L protein). For example, in some instances, markers of LCMV can include LCMV GP and/or LCMP NP nucleic acid and/or protein. In some instances, markers of LCMV can include or can be detected by targeting a portion of the maker. In some instances, portions of LCMV markers can include, for example, regions of nucleic acids that are conserved between one or more LCMV strains or isolates. For example, suitable portions for detection can include those regions identified as being conserved in FIGS. 2-4 (e.g., in one or more of SEQ ID NOs:1-57). Alternatively or in addition, suitable portions can include a region within a LCMV nucleic acid that has at least 50% identity (e.g., 50%, 60%, 70%, 80%, 85%, 90%, 95%, 98%, 99%, or 100% identity) to a region in one or more distinct LCMV strains (e.g., in one or more of SEQ ID NOs:1-57). In some instances, suitable portions can include a region within a LCMV protein that has at least 50% identity (e.g., 50%, 60%, 70%, 80%, 85%, 90%, 95%, 98%, 99%, or 100% identity) to a region in a protein encoded by one or more of SEQ ID NOs:1-51. In some instances, suitable portions can include a region within a LCMV protein that has at least 50% identity (e.g., 50%, 60%, 70%, 80%, 85%, 90%, 95%, 98%, 99%, or 100% identity) to a region in one or more of SEQ ID NOs:52-57.

Compositions suitable for specifically detecting such one or more or at least one LCMV nucleic acids or portions thereof can include, but are not limited to nucleic acid probes or primers. Methods for designing and synthesizing suitable probes or primers are known in the art. In some instances, nucleic acid probes or primers that can be used to detect one or more or at least one marker of LCMV can include nucleic acid probes or primers containing, for example, 10 or more nucleic acids (e.g., 10, 11, 12, 13, 14, 15, 16, 17, 18, 19, 20, 21, 22, 23, 24, 25, 26, 27, 28, 29, 30, 35, 40, 45, 50, 55, 60, 70, 75, 80, 85, 90, 95, 100, 200, 300, 400, 500, 600, 700, 800, 900, 1000, or more than 1000 nucleic acids), e.g., wherein the 10 or more nucleic acids has at least at least 50% identity (e.g., 50%, 60%, 70%, 80%, 85%, 90%, 95%, 98%, 99%, or 100% identity) to a target region within one or more LCMV markers (e.g., within one or more of SEQ ID NOs:1-51), such that the nucleic acid probe or primer binds specifically to the target region (e.g., within one or more of SEQ ID NOs:1-51). In some instances, the probe or primer can bind (e.g., bind specifically) to the target region under stringent binding conditions (e.g., low stringency, medium stringency, or high stringency). Hybridization conditions that qualify as low, medium, and high stringency hybridization conditions are known in the art. It is understood in the art that a complementary nucleic acid sequence need not be 100% complementary to that of its target nucleic acid to be specifically hybridizable. A complementary nucleic acid sequence of the invention is specifically hybridizable when binding of the sequence or a portion thereof, to the target sequence occurs such that amplification or the target portion can occur. In some instances, the multiple probes or primers can be used to detect the same LCMV nucleic acid in a sample (the term "sample" or "biological sample" refers to a sample of tissue or body fluid obtained from a subject (human or animal), including but not limited to blood, serum, plasma, tissue biopsies and surgical specimens, saliva, urine, cerebrospinal fluid etc. Biological sample also includes in vitro cultured cells and culture media. The samples may be treated prior to analysis by heating, centrifugation, precipitation etc.). In such instances, the probes can detect overlapping portions of the same LCMV nucleic acid or they can detect non-overlapping portions of the same LCMV nucleic acid. Alternatively or in addition, the multiple probes or primers can be used to detect distinct LCMV nucleic acids in a sample. In some instances, nucleic acid probes or primers that can be used to detect one or more or at least one marker of LCMV can include, for example, one or more or at least one of SEQ ID NO:58, SEQ ID NO:59 (e.g., a combination of SEQ ID NO:58 and 59, which detect LCMV NP), SEQ ID NO:60, SEQ ID NO:61 (e.g., a combination of SEQ ID NO:60-61, which detect LCMV GP), SEQ ID NO:62, SEQ ID NO:63 (e.g., a combination of SEQ ID NO:62-63, which detect LCMV ZP), SEQ ID NO:66, SEQ ID NO:67 (e.g., a combination of SEQ ID NO:66-67, which detect LCMV NP), SEQ ID NO:68, SEQ ID NO:69 (e.g., a combination of SEQ ID NO:68-69, which detect LCMV GP), SEQ ID NO:70, SEQ ID NO:71 (e.g., a combination of SEQ ID NO:70-71, which detect LCMV L), SEQ ID NO:72, SEQ ID NO:73 (e.g., a combination of SEQ ID NO:72-73, which detect LCMV Z). In some instances, nucleic acid probes or primers that can be used to detect one or more or at least one marker of LCMV can include nucleic acid probes or primers with at least 50% (e.g., 50%, 60%, 70%, 80%, 85%, 90%, 95%, 96%, 97%, 98%, 99%, and 100%) sequence homology or identity to one or more of SEQ ID NO:58, SEQ ID NO:59 (e.g., a combination of SEQ ID NO:58 and 59, which detect LCMV NP), SEQ ID NO:60, SEQ ID NO:61 (e.g., a combination of SEQ ID NO:60-61, which detect LCMV GP), SEQ ID NO:62, SEQ ID NO:63 (e.g., a combination of SEQ ID NO:62-63, which detect LCMV ZP), SEQ ID NO:66, SEQ ID NO:67 (e.g., a combination of SEQ ID NO:66-67, which detect LCMV NP), SEQ ID NO:68, SEQ ID NO:69 (e.g., a combination of SEQ ID NO:68-69, which detect LCMV GP), SEQ ID NO:70, SEQ ID NO:71 (e.g., a combination of SEQ ID NO:70-71, which detect LCMV L), SEQ ID NO:72, SEQ ID NO:73 (e.g., a combination of SEQ ID NO:72-73, which detect LCMV Z). In some instances, nucleic acid probes or primers that can be used to detect one or more or at least one marker of LCMV can include one or more of the probes or primers described in Example 21 herein.

In some instances, methods suitable for detecting one or more or at least one LCMV nucleic acids or portions thereof can include, for example, RT-PCR and/or RLM-RACE (e.g., as described in Example 2 herein).

Alternatively or in addition, markers of LCMV can include one or more LCMV peptides (e.g., including polypeptides or proteins), e.g., and methods for detecting LCMV can include, for example, detection of one or more LCMV peptides.

The terms "polypeptide", and "protein" refer to a polymer or oligomer of amino acid residues, including full-length proteins, fragments, peptides, oligopeptides, multimers and the like. The term also includes posttranslational modifications (glycosylation, phosphorylation, acetylation etc.), as well as deletions, additions, substitutions, mutations to the native sequence (natural mutations and variations), e.g., as long as the product maintains the desired activity), e.g., one or more LCMV peptides disclosed herein.

Figure 6I:
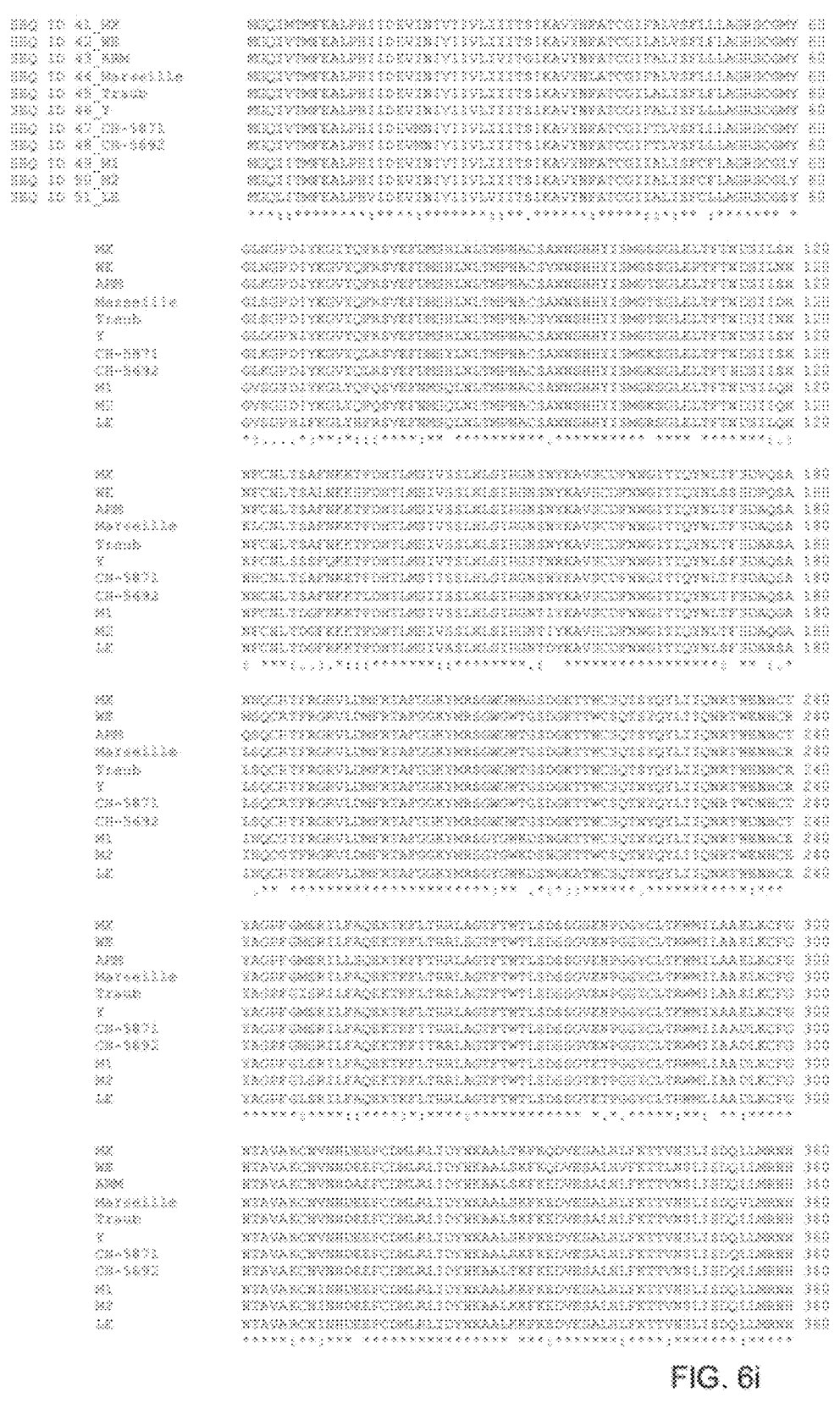
Figure 7:
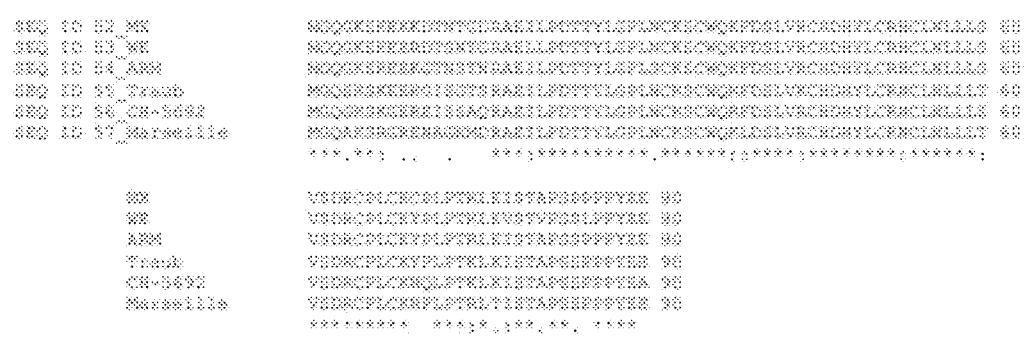

In some instances, the LCMV peptides can be a full length LCMV peptide or a fragment of a LCMV peptide, e.g., a fragment of a LCMV peptide disclosed herein (see, e.g., peptides or peptide fragments encoded by one or more of SEQ ID NOs:1-51 and/or one or more of SEQ ID NOs:52-58 or fragments/portions of one or more of SEQ ID NOs:52-58). Suitable fragments can include regions of amino acids that are conserved between one or more LCMV strains or isolates. For example, suitable fragments can include those regions identified as being conserved in FIGS. 5-7 or SEQ ID NOs: 1-58 (including for example, peptides encoded by one or more of SEQ ID NOs:1-51). Alternatively or in addition, suitable fragments can include a region within an LCMV amino acid that has at least 50% identity (e.g., 50%, 60%, 70%, 80%, 85%, 90%, 95%, 98%, 99%, or 100% identity) to a region in one or more distinct LCMV strains. In some instances, suitable fragments can include at least 3 amino acids (e.g., 3-10 amino acids). Alternatively or in addition, suitable fragments can include 3, 4, 5, 6, 7, 8, 9, 10, 11, 12, 13, 14, 15, 16, 17, 18, 19, 20, 25, 30, 40, 50, 60, 70, 80, 90, 100, or more amino acids. In some instances, suitable fragments can include an antigen or epitope. The term "antigen" refers to various LCMV polypeptides and their fragments (native, recombinant or synthetic), which contain one or more epitopes that bind LCMV antibodies and are derived from any of the isolates/strains of LCMV. Furthermore, the antigen may be a fusion protein between the reference LCMV antigen molecule (full-length or fragment thereof) and another antigen/protein/peptide that does not disrupt the reactivity of LCMV antigen. The antigen may be a component of an immunogenic composition, which refers to a sample (including but not limited to infected cell, whole cell lysate, protein extract), that may not or may be substantially purified (comprising more than 50% of sample in which in resides), or may be isolated (in separated and discrete form).

Figure 2I:
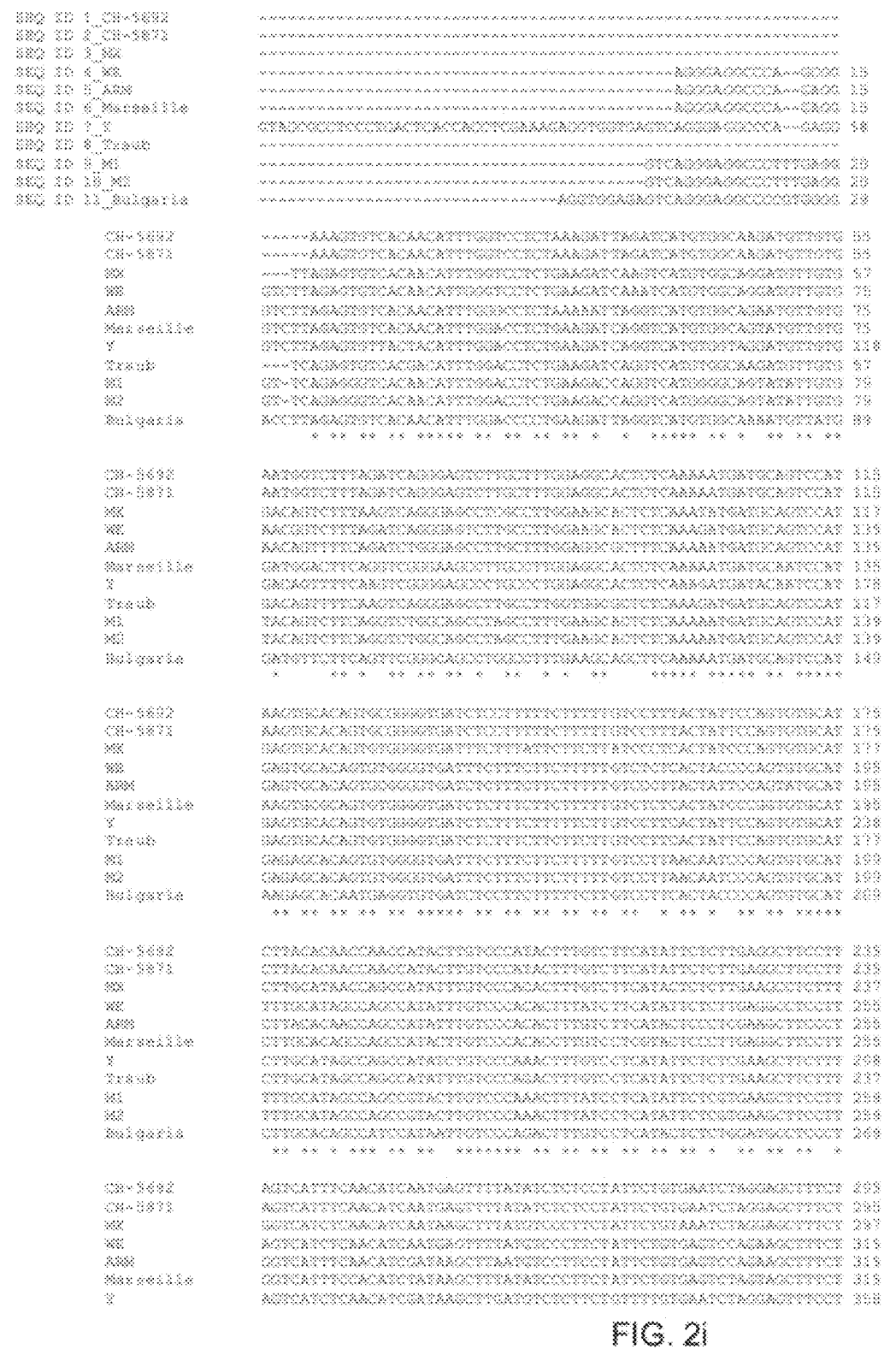
Figure 2:
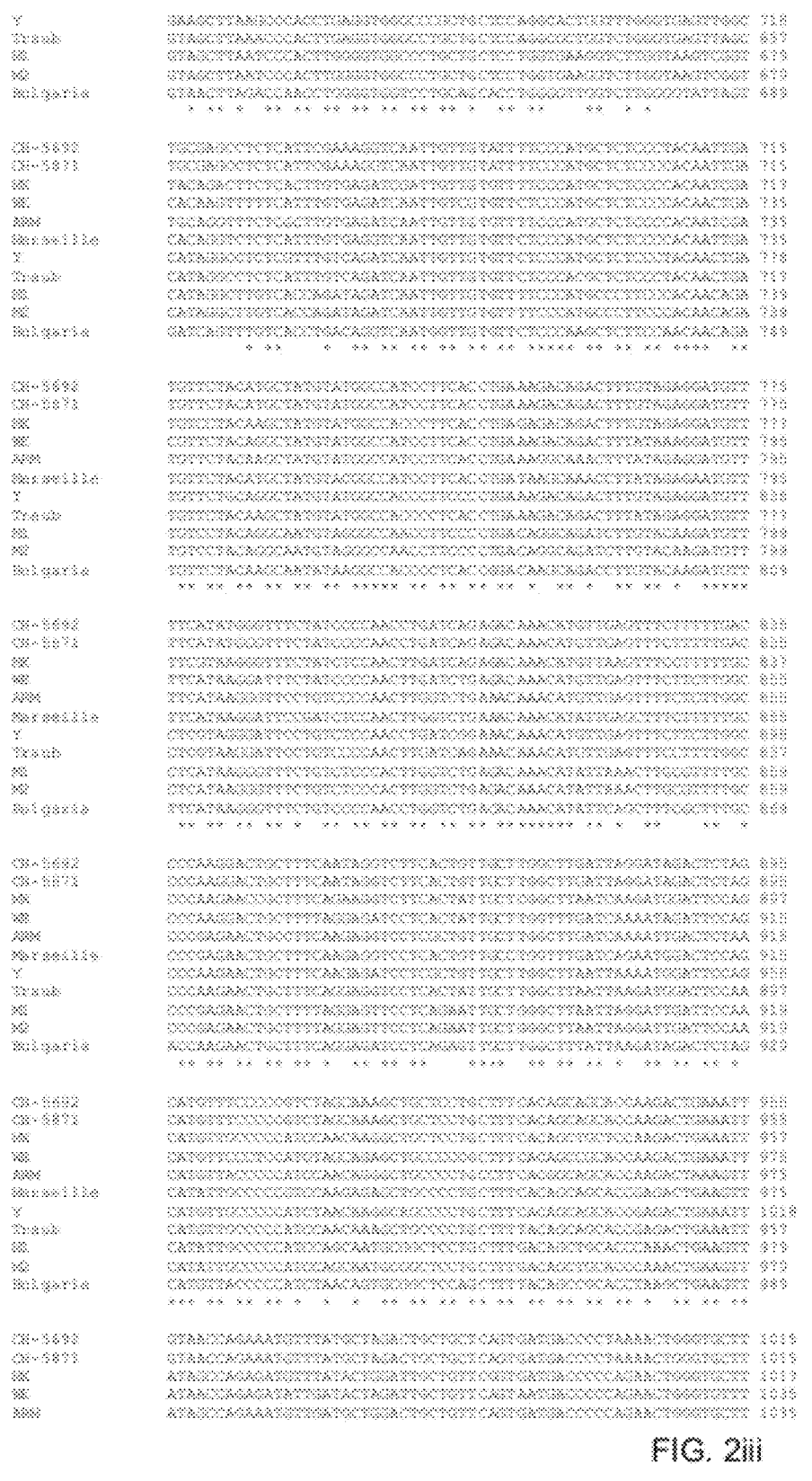
Figure 2V:
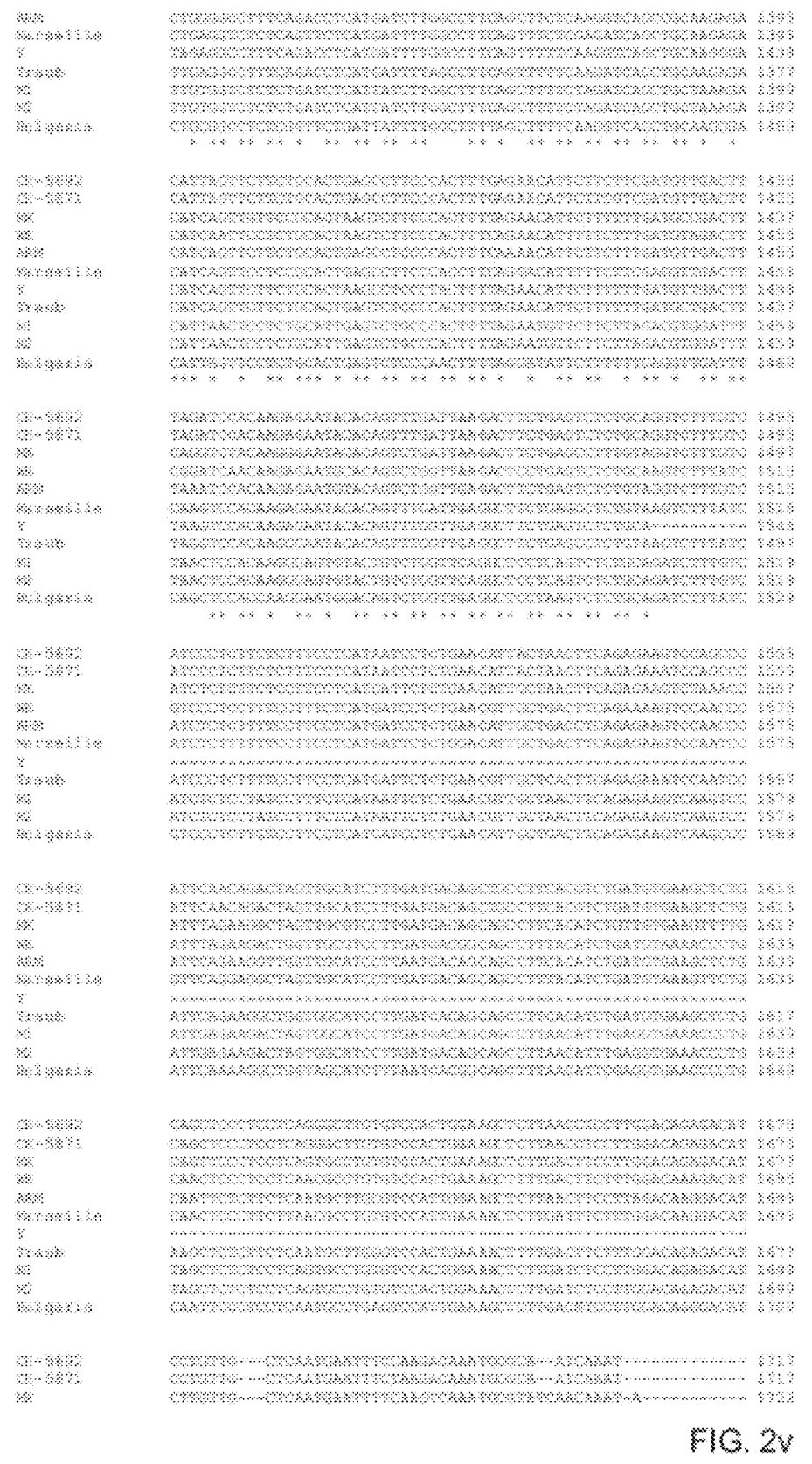

The term NP antigen refers to an antigen derived from the nucleocapsid protein of LCMV (e.g., including any LCMV strain and isolate). The nucleotide and corresponding amino acid sequences for various NP antigens of LCMV are known (FIGS. 2 and 5, SEQ ID NOS: 1-11 and 31-40). Additional sequences have been deposited with Genbank as specified in Prior publications (see below). A representative immunoreactive NP antigen useful in the present assays is a fusion protein derived from MX strain of LCMV. It includes several epitopes, and antibodies binding this antigen are cross-reactive with NP antigen from Armstrong strain.

The term ribonucleoprotein or RNP refers to a complex of virus genomic RNA segments (S and/or L) covered by NP antigen. Such RNPs are formed during the LCMV infection within the infected cells and can be also released to extracellular space.

The term GP antigen refers to an antigen derived from the glycoprotein of LCMV (including any LCMV strain and isolate). The nucleotide and corresponding amino acid sequences for various GP antigens of LCMV are known (see, e.g., FIGS. 3 and 6, SEQ ID NOS: 12-23 and 41-51). Additional sequences have been deposited with Genbank as specified in Prior publications (see below). A representative immunoreactive GP antigen useful in the present assays is a fusion protein derived from MX strain of LCMV. It includes several epitopes, and antibodies binding this antigen are cross-reactive with GP antigen from Armstrong strain.

The term GPC antigen is a precursor, immature form of a GP antigen and is typical for persistent or aberrant infection. It includes the epitope spanning the region (fragment) of GPC cleavage to GP1 and GP2, which is relevant for specific recognition of GPC only. The sequences for various GPC antigens of LCMV are known (see FIGS. 3 and 6, SEQ ID NOS: 12-23 and 41-51).

The term GP1 antigen means a mature external subunit of envelope antigen that is typical for acute infection. It includes the epitope of the C-terminal region (fragment) of GP1, which is not exposed in GPC. The amino acid sequences for various GP1 antigens of LCMV are known.

The term ZP antigen refers to an antigen derived from the Z protein of LCMV. The nucleotide and corresponding amino acid sequences for various ZP antigens of LCMV are known. (see FIGS. 4 and 7, SEQ ID NOS: 24-30 and 52-57). Additional sequences have been deposited with Genbank as specified in Prior publications (see below). A representative immunoreactive ZP antigen useful in the present assays is a fusion protein derived from MX strain of LCMV. It includes several epitopes, and antibodies binding this antigen are cross-reactive with ZP antigen from Armstrong strain.

The term epitope means a site on an antigen, to which specific B cells and/or T cells respond, and which reacts with LCMV antibodies present in a biological sample and which stimulates antibody production. The term is used interchangeably with "antigenic determinant orantigenic site. An epitope can comprise 3 to 10 or more amino acids orchestrated in a unique conformational or linear manner.

The term immunogenic composition refers to at least one immunogenic polypeptide (e.g. NP, GP, ZP and/or ribonucleoprotein (RNP)).

In some embodiments, peptide markers of LCMV can be used as diagnostics, e.g., to detect antibodies directed against LCMV in a biological sample.

The antigens may be also used to produce polyclonal and monoclonal antibodies for use in diagnostics. Polyclonal antibodies can be produced by administering the LCMV antigens, either isolated, or substantially purified, or as part of immunogenic compositions (i.e. in the form of infected cells) to a mammal, such as a mouse, rat, rabbit, goat, sheep, lama, horse etc. Serum from the immunized antigen can be collected and the antibodies can be further purified. Techniques for producing and processing polyclonal antibodies are known in the art.

The term antibody is used in the broadest sense and specifically covers, for example, single monoclonal antibodies (including agonist, antagonist, and neutralizing antibodies, de-immunized, murine, chimeric or humanized antibodies), antibody compositions with polyepitopic specificity, single-chain antibodies, diabodies, triabodies, immuno-conjugates and antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

An "antibody fragment" or "antigen binding fragment" comprises a portion of an intact antibody, preferably comprising the antigen-binding or variable region thereof. Examples of antibody fragments include less than full length antibodies, Fab, Fab', F(ab')2, and Fv fragments; diabodies; linear antibodies; single-chain antibody molecules; single-chain antibodies, single domain antibody molecules, fusion proteins, recombinant proteins and multispecific antibodies formed from antibody fragment(s).

An antibody "which binds" an antigen of interest, e.g. an LCMV antigen or marker, is one capable of binding that antigen with sufficient affinity such that the antibody is useful as a therapeutic or diagnostic agent in targeting a cell expressing the antigen. Where the antibody is one which binds an LCMV antigen or marker, it will usually preferentially bind the LCMV antigen or marker as opposed to other antigens, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

"Humanized" and/or "chimeric" forms of non-human (e.g. murine) immunoglobulins refer to antibodies which contain specific chimeric immunoglobulins, immunoglobulin chains or fragments thereof (such as Fv, Fab, Fab', F(ab')2 or other antigen-binding subsequences of antibodies) which results in the decrease of a human anti-mouse antibody (HAMA), human anti-chimeric antibody (HACA) or a human anti-human antibody (HAHA) response, compared to the original antibody, and contain the requisite portions (e.g. CDR(s), antigen binding region(s), variable domain(s) and so on) derived from said non-human immunoglobulin, necessary to reproduce the desired effect, while simultaneously retaining binding characteristics which are comparable to said non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin. In some instances, antibodies disclosed herein can be humanized.

Throughout the application, hybridoma cell lines, as well as the monoclonal antibodies which are produced therefrom, are referred to by their internal designation, e.g., M59, M87, M166, and MJ3 or their Depository Designation, LMBP 9216CB (M166) and LMBP 9217CB (MJ3).

As used herein, an "immuno-conjugate" means any molecule, such as an antibody or antibody fragment, chemically or biologically linked to reporter moieties. The antibody may be linked to the reporter moiety at any location along the molecule so long as it is able to bind its target.

Monoclonal antibodies can be generated following immunization with the LCMV antigens or their fragments as described above. Spleen of immunized animal containing normal B cells can be fused to myeloma cells essentially by a procedure developed by Kohler and Milstein (1975) and generated hybridomas can be screened for production of specific antibodies using various immunodetection methods. Specific monoclonal antibodies can be obtained in the form of hybridoma medium or purified by affinity chromatography on Protein A/G Sepharose. Antibody molecule fragments, e.g. F(ab)$_2$, Fv and sFv molecules can be produced using known techniques. Alternatively, a phage-display system can be used to identify and expand monoclonal antibody molecule populations in vitro and/or improve the immunological properties of the antibodies.

Compositions suitable for specifically detecting one or more LCMV peptides or LCMV peptide fragments can include, but are not limited to antibodies and/or antibody fragments. In some instances, the term "antibody" refers to a molecule, its fragments (Fab'2, Fab, Fv, sFv, minibodies and any other functional fragments), its hybrid (chimeric) or bispecific variants, which specifically bind to an antigen and/or epitope of interest. The term includes antibodies obtained both from polyclonal and monoclonal preparations. In some instances, the antibody or antibody fragment can be humanized.

In some instances, compositions for detecting one or more LCMV peptides or fragments can include (e.g., can consist, consist essentially of, or can comprise), for example, the heavy and/or light chain variable regions, or portions thereof, of one or more antibodies disclosed herein, e.g., one or more of M87, M59, M166, and/or MJ3. For example, compositions can include the heavy and light chain variable regions, or portions thereof, of M87, M59, M166, and MJ3. Alternatively, compositions can include the heavy chain variable region, or a portion thereof, of M87, M59, M166, or MJ3 and the light chain variable region, or a portion thereof, of M87, M59, M166, or MJ3, wherein the heavy chain variable region and the light chain variable are not derived from the same antibody. In some instances, compositions can include one or more complementarity determining regions (CDRs) of one or more of M87, M59, M166, and/or MJ3 (e.g., one or more of CDR1, CDR2, and or CDR3). For example, CDRs from different antibodies can be combined.

In some instances, compositions for detecting one or more LCMV peptides or fragments can include (e.g., can consist, consist essentially of, or can comprise), for example, the heavy chain variable region of antibody M87 (i.e., SEQ ID NO:74) or an amino acid sequence with at least 50% identity (e.g., 50%, 60%, 70%, 80%, 85%, 90%, 95%, 98%, 99%, or 100% identity) to SEQ ID NO:74. In some instances, compositions for detecting one or more LCMV peptides or fragments can include (e.g., can consist, consist essentially of, or can comprise), for example, the heavy chain variable region of antibody M87 (i.e., SEQ ID NO:74) containing at least one (e.g., 1, 2, 3, 4, 5, 6, 7, 8, 9, 10, 11, 12, 13, 14, 15, 16, 17, 18, 19, 20, 21, 22, 23, 24, 25, less than 30, less than 40, less than 50, or less than 100) conservative amino acid substitutions, as described below. For example, in some instances, compositions for detecting one or more LCMV peptides or fragments can include (e.g., can consist, consist essentially of, or can comprise), for example, the heavy chain variable region of antibody M87 (i.e., SEQ ID NO:74) wherein regions corresponding to CDR1, CDR2, and/or CDR3 can contain at least one (e.g., 1, 2, 3, 4, 5, 6, 7, 8, 9, 10, 11, 12, 13, 14, 15, 16, 17, 18, 19, 20, 21, 22, 23, 24, 25, less than 30, less than 40, less than 50, or less than 100) conservative amino acid substitution, and regions outside those corresponding to CDR1, CDR2, and/or CDR3 (e.g., the framework regions (i.e., FR1, FR2, and/or FR3)) have at least 50% identity (e.g., 50%, 60%, 70%, 80%, 85%, 90%, 95%, 98%, 99%, or 100% identity) to the corresponding regions in SEQ ID NO:74. In some instances, compositions for detecting one or more LCMV peptides or fragments can include (e.g., can consist, consist essentially of, or can comprise): CDR3 of the heavy chain variable region of M87 (e.g., SEQ ID NO:78), and/or CDR2 of the heavy chain variable region of M87 (e.g., SEQ ID NO:77), and/or CDR1 of the heavy chain variable region of M87 (e.g., SEQ ID NO:76), wherein any of CDR3, 2, and 1 can optionally include at least one (e.g., 1, 2, 3, 4, 5, 6, 7, 8, 9, 10, 11, 12, 13, 14, 15, 16, 17, 18, 19, 20, 21, 22, 23, 24, 25, less than 30, less than 40, less than 50, or less than 100) conservative amino acid substitutions.

In some instances, compositions for detecting one or more LCMV peptides or fragments can include (e.g., can consist, consist essentially of, or can comprise) LMBP 9216CB (M166) and/or LMBP 9217CB (MJ3).

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

Other compositions suitable for specifically detecting one or more LCMV peptides or LCMV peptide fragments can include antigen binding peptides. Such peptides bind specifically to one or more LCMV peptides or LCMV peptide fragments. In some instances, such peptides can include a complementarity determining region (CDR) of an antibody disclosed herein (e.g., one or more of CDR1, CDR2, CDR3).

In some instances, the one or more of the antibodies or antigen binding fragments thereof can be modified by insertion of one or more conservative amino acid substitutions.

A "non-essential" amino acid residue is a residue that can be altered from the wild-type sequence of a polypeptide (without abolishing or substantially altering its activity. An "essential" amino acid residue is a residue that, when altered from the wild-type sequence of the polypeptide, results in abolishing or substantially abolishing the polypeptide activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, the term "essential" amino acid residue as used herein, includes conservative substitutions of the essential amino acid. Generally, the "essential" amino acid residues are found at the interacting face of the alpha helix.

The "interacting face" of the alpha helix includes those amino acid residues which interact with other amino acid residues. In this case, the interacting face includes those amino acids that interact with LCMV. Methods for identifying the interactive face of a peptide are known in the art (see, e.g., Broglia et al., Protein sci., 14(10):2668-81, 2005; Hammond et al., J. Pharm. Sci., 98(1):4589-603, 2009; Ng and Yang, J. Phys. Chem. B., 111(50):13886-93, 2007; and Bird et al., PNAS USA, 197:14093, 2010). In some embodiments, the amino acid sequence of any peptide disclosed herein can be varied as long as the residues of the interacting face are identical to those of SAH-p53-8 or are conservative substitutions thereof.

In some embodiments, compositions suitable for specifically detecting one or more LCMV peptides or LCMV peptide fragments can be modified to include, for example, amino and/or carboxyl terminal labels or moieties (e.g., detectable moieties). Exemplary moieties can include, but are not limited to, fluorescent moieties (e.g., a fluorescent probe (e.g. fluorescein or rhodamine)), a metal chelating group, a radioisotope, or moieties that can chelate a radioisotope (e.g., mercaptoacetyltriglycine or 1,4,7,10-tetraazacyclododecane-N,N',N'',N'''-tetraacetic acid (DOTA)) chelated to a radioactive isotope of Re, In or Y), a targeting moiety, a biotin moiety, a tat protein, an affinity label, a fatty acid-derived acyl group, and any other detectable moiety that is not otherwise present in the peptide and/or in any other peptide present (e.g., a naturally occurring peptide) or to be used in the methods disclosed herein (e.g., a LCMV peptide or fragment thereof or a peptide for detection of an LCMV peptide or fragment thereof). Methods for preparing peptides with amino and/or carboxyl terminal moieties are routine and are known in the art. The term "label" refers to a molecule capable of detection, such as radioisotope, fluorescent dyes, chemiluminescent dyes, chromophores, metal ions, metal salts, enzymes, enzyme substrates, enzyme cofactors, enzyme inhibitors, adaptors (biotin, avidin, streptavidin, digoxigenin) etc.

Those of skill in the art readily understand how to determine the identity of two nucleic acids or amino acids. For example, identity can be calculated after aligning the two sequences so that the identity is at its highest level. For example, nucleic acid identity can be determined using the algorithms disclosed in Zuker, Science 244:48-52 (1989); Jaeger et al., Proc. Natl. Acad. Sci. USA 86:7706-10 (1989); and Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if the required level of identity is found with at least one of these methods, the sequences would be said to have the stated identity and to be disclosed herein.

The peptides of this invention can be made by chemical synthesis methods, which are well known to the ordinarily skilled artisan. See, for example, Fields et al., Chapter 3 in Synthetic Peptides: A User's Guide, ed. Grant, W.H. Freeman & Co., New York, N.Y., 1992, p. 77. Hence, peptides can be synthesized using the automated Merrifield techniques of solid phase synthesis with the $\alpha$-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptides can also be expressed (e.g., recombinantly expressed) in a wide variety of systems and host cells, including insect, mammalian, bacterial, viral and yeast expression systems and cells, all of which are well known in the art.

A number of appropriate host cells for use with the above systems are also known. For example, mammalian cell lines include immortalized cell lines available from cell culture collections, such as, but not limited to CHO, HeLa, COS, MDCK, etc.

Following preparation, the peptides can be assayed, e.g., to confirm their sequence, binding affinities, and stability (in vitro and in vivo) using routine methods.

In some embodiments, one or more of the compositions disclosed herein can be mounted onto a solid support. The term "solid support" refers to a solid surface to which a macromolecule, e.g. protein, polypeptide, peptide, polynucleotide can be attached, including but not limited to microplate well, sepharose/agarose matrix, magnetic beads, glass slide, nylon, polyacrylamide, nitrocellulose membrane, silica plate, etc. Furthermore, solid support can be represented by infected cells in culture or in tissue specimens that contain LCMV antigens either exposed on cell surface or present within the cytoplasm.

The term "immune complex" refers to the molecular composite formed via binding of antibody to an antigen in the assay settings. It also refers to naturally occurring multimolecular composite containing viral ribonucleoprotein and immunoglobulins in biological samples.

Diagnostic Methods

The present disclosure also features methods for detecting LCMV in a sample, e.g., using one or more of the compositions for detecting LCMV disclosed herein (e.g., one or more probes or primers and/or one or more LCMV peptides or LCMV peptide fragments and/or one or more compositions for detecting one or more LCMV peptides or LCMV peptide fragments (e.g., one or more antibodies or antibody fragments).

Antibodies against LCMV antigens/epitopes may be used for detection of the presence of LCMV proteins or ribonucleoproteins in a biological sample using, for example, different immunoassays or immunoassays combined with molecular methods. Immunoassays may use one or more antibodies and protocols may have different formats, including direct reaction, sandwich, competition, immunoprecipitation, immunoblotting etc. They can be also combined with amplification procedures in immuno-PCR formats, where amplification templates are represented either by virus RNA or by oligonucleotides linked to antibody/antibodies or detectors. Such procedures are known in the art.

Diagnostic assays may detect either virus antigens or anti-virus antibodies. The assays may include immunoprecipitation (IP), immunoblotting (IB), IP combined with IB, enzyme-labeled immunoassays, biotin/avidin type assays, PCR, immuno-PCR and the like. The detection generally includes revealing labels such as fluorescent, chemiluminescent, radioactive, enzymatic label or dye molecules, or oligonucleotides for amplification to generate labeled product.

The assays generally involve separation of unbound antibody or antigen in a liquid phase from a solid support (either without or with capture) to which antigen-antibody complexes are bound. Then the antigen-antibody complexes are detected with detector interacting or conjugated with label.

Typically, a solid support is first reacted with capture. Then any non-immobilized components are removed by washing, and the solid support-bound component is then contacted with a biological sample under suitable conditions. After washing to remove any unbound material, a secondary binder moiety, i.e. detector, can be added after suitable binding conditions. The presence of the detector can then be detected using techniques well known in the art. Alternatively, detector can be added simultaneously with the labeled competitor molecule and extent of competition can reveal the amount of the detector present in the sample.

Figure 9:
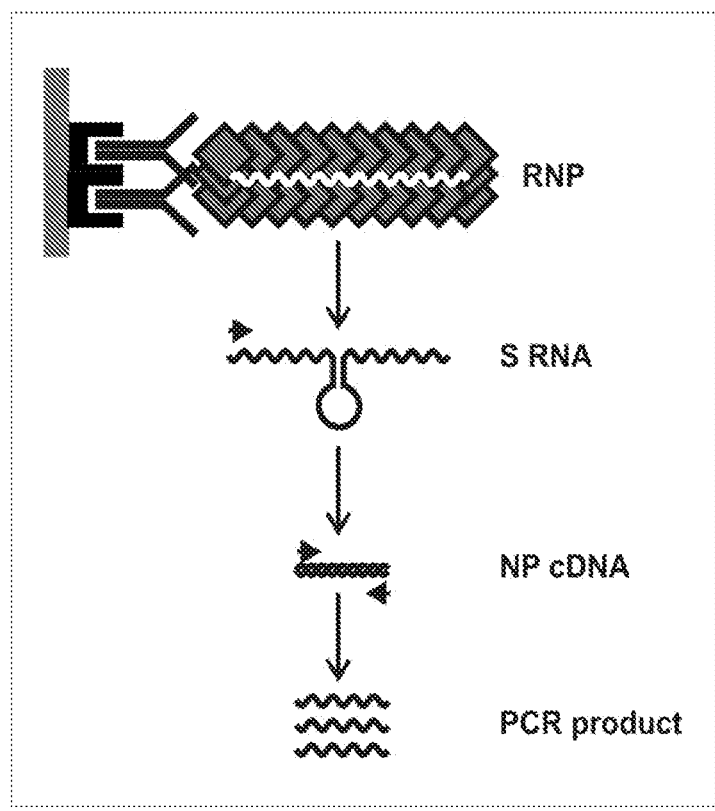
FIG. 9 is an illustration showing an exemplary RNA based assay for use in the methods disclosed herein.

Several different variations of the assay can be performed as illustrated on FIGS. 8 and 9. FIG. 8 shows compositions of exemplary immunodetection tests that employ either LCMV antigens or antibodies.

In A series of the assays, individual virus antigens or their mixtures serve as capture to which anti/LCMV antibodies from biological sample are bound and then detected with various detectors or their combinations. In A1 variant, detector is represented by Protein A/G directly conjugated with label. In A2 variant, detector is represented by secondary anti-human (or anti-mouse or other animal species-specific) IgG or IgM directly conjugated with label. In A3 variant, detector antibody is conjugated with biotin, which is further bound with avidin/streptavidin and then revealed with label-conjugated biotin. In A4 variant, secondary antibody is linked with oligonucleotide, which can be amplified by corresponding primers in presence of labeled trinucleotides. In A5 variant, secondary antibody is conjugated with biotin, which is then reacted with avidin/stretavidin and with biotin linked with oligonucleotide, which can be amplified by corresponding primers in presence of labeled trinucleotides.

In B series of the assays, antibodies specific for NP, GP (e.g. GPC, GP1) and/or ZP are attached to solid phase and serve as capture to which LCMV antigens from biological sample are bound and then detected with non-competing antibody or antibody/associated detectors. In B1 variant, detector is represented by LCMV antigen-specific antibody directly conjugated with label. In B2 variant, detector is represented by anti-human (or anti-mouse or other animal species-specific) IgG or IgM directly conjugated with label. In B3 variant, detector antibody is conjugated with biotin, which is further bound with avidin/streptavidin and then revealed with label-conjugated biotin. In B4 variant, secondary antibody is linked with oligonucleotide, which can be amplified by corresponding primers in presence of labeled trinucleotides. In B5 variant, secondary antibody is conjugated with biotin, which is then reacted with avidin/stretavidin and the with biotin linked with oligonucleotide, which can be amplified by corresponding primers in presence of labeled trinucleotides.

In some embodiments, the methods include selecting a subject (the term "subject" is used throughout the specification to describe an animal, human or non-human. Both human and veterinary applications are contemplated. The term can include, for example, mammals, e.g., humans, other primates, pigs, rodents such as mice and rats, rabbits, guinea pigs, hamsters, cows, horses, cats, dogs, sheep and goats). For example, subjects at risk for LCMV infection or subjects suspected of having LCMV can be selected. Alternatively or in addition, subjects with a condition or disease that renders the subject more susceptible to damage caused by LCMV can be selected. Such subjects can include subjects that are planning to become pregnant or that are pregnant, immunocompromised subjects, transplant recipients, and subjects at risk for developing or having cancer. In some embodiments, a subject is selected if the subject has a condition known to manifest hypoxia in the subject.

In some embodiments, following selection, a sample can be obtained from the subject. The sample can then be contacted with one or more of the compositions for detecting LCMV disclosed herein (e.g., one or more probes or primers and/or one or more LCMV peptides or LCMV peptide fragments and/or one or more compositions for detecting one or more LCMV peptides or LCMV peptide fragments (e.g., one or more antibodies or antibody fragments). In some instances, the methods can include treating or recommending the subject for treatment for LCMV infection if LCMV is detected in the subject.

The methods can also include monitoring or evaluating the subject during and after treatment to determine the efficacy of the treatment, and, if necessary, adjusting treatment to improve efficacy of the treatment.

Kits

The present disclosure also features kits comprising one or more of the compositions for detecting LCMV disclosed herein. The kits can also include informational material relevant to the compositions and methods of using the compositions. The informational material can be descriptive, instructional, marketing or other material that relates to the compositions and methods described herein.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

In addition to the compound, the composition of the kit can include other ingredients, such as a solvent or buffer, a stabilizer, a preservative, and/or a second agent for treating a condition or disorder described herein. Alternatively, the other ingredients can be included in the kit, but in different compositions or containers than the compound. In such embodiments, the kit can include instructions for admixing the agent and the other ingredients, or for using one or more compounds together with the other ingredients.

The sequences disclosed herein are publicly available, e.g., online at the National Center for Biotechnology Information (NCBI) website (see ncbi.nlm.nih.gov) and in the literature, as follows:

LCMV strain MX GPC gene, NCBI Accession no. EU195888 (EU195888.1) and Tomaskova, J et al., Virus Genes, 37:31-38 (2008);

LCMV strain MX NP gene, NCBI Accession no. Y16308 (Y16308.1) and Reiserova, L. et al., Virology 257:73-83 (1999);

LCMV strain MX Z gene, NCBI accession no. AJ131281 (AJ131281.1) and Gibadulinova, A. et al., Acta Virol., 42:369-374 (1998);

LCMV strain Armstrong 53b—S segment, NCBI accession no. M20869 (M20869.1) and Salvato, M. et al., Virology, 164:517-522 (1988);

LCMV strain Armstrong 53b—LS segment, NCBI accession no. AY847351 (AY847351.1) and Grande-Perez, A. et al., J. Virol., 79:10451-10459 (2005);

LCMV strain CH-5692—S segment, NCBI accession no. AF325214 (AF325214.1);

LCMV strain CH-5692—L segment, NCBI accession no. DQ868484 (DQ868484.1);

LCMV strain CH-5871—S segment, NCBI accession no. AF325215 (AF325215.1) and Asper, M. et al., Virology, 284:203-213 (2001);

LCMV strain Traub—S segment, NCBI accession no. DQ868487 (DQ868487.1);

LCMV strain Traub—L segment, NCBI accession no. DQ868488 (DQ868488.1) and Emonet, S. et al., Genetic comparisons and evolution of 6 LCMV strains;

LCMV strain LE GPC gene, NCBI accession no. EF164923 (EF164923.1) and Meritet, J. F. et al., Human Fetal Lymphocytic Choriomeningitis Virus Infection with a New Genomic Variant;

LCMV strain M1—S segment, NCBI accession no. AB261991 (AB261991.1);

LCMV strain M2—S segment, NCBI accession no. AB261990 (AB261990.1) and Ike, F. et al., Comp. Med. 57:272-281 (2007);

LCMV isolate Marseille #12—S segment, NCBI accession no. DQ286931 (DQ286931.1);

LCMV isolate Marseille #12—L segment, NCBI accession no. DQ286932 (DQ286932.1) and Emonet, S. et al., Emerging Infect. Dis., 13:472-475 (2007);

LCMV strain WE—S segment, NCBI accession no. M22138 (M22138.1) and Romanowski, V. et al., Virus Res., 3:101-114 (1985);

LCMV strain WE—S segment, NCBI accession no. AF004519 (AF004519.1) and Djavani, M. et al., Virus Genes, 17:151-155 (1998);

LCMV strain Bulgaria—S segment, NCBI accession no. GQ862982 (GQ862982.1);

LCMV strain Bulgaria—S segment, NCBI accession no. GQ862981 (GQ862981.1) and Palacios, G. et al., Genetic diversity of Lymphocytic choriomeningitis viruses;

LCMV strain Y—S segment, NCBI accession no. DQ118959 (DQ118959.1) and Compton, S. R., Lymphocytic choriomeningitis virus strain Y; and NCBI accession nos. FJ607019-FJ607038, 13-JUL-2010, Albarino, C. G. et al., Emerging Infect. Dis., 16:1093-1100 (2010).

EXAMPLES

The invention is further described in the following examples, which do not limit the scope of the invention described in the claims.

Example 1

Regions of Sequence Conservation Exist Between Diverse Strains/Isolates of LCMV

Recent genomic analysis of 29 LCMV strains collected from a variety of geographic and temporal sources showed that these viruses are diverse. Several distinct lineages exist, but there is little correlation with time or place of isolation (Albarino et al, 2010). The S and L segment sequences of all known LCMV isolates were distributed in 3 (L segment) or 4 (S segment) different genetic groups or lineages. Up to 25% nucleotide divergence was observed between the S segment lineages, and 28% divergence between the L segment lineages. This nucleotide divergence translates to 18%, 13%, 10%, and 6% divergence in the amino acid sequences of the Z, L, GPC, and NP proteins, respectively (Albarino et al, 2010). However, regions of considerable sequence identity exist among different strains/isolates (see FIGS. 2-7) and derived antigens show cross-reactivity with LCMV-specific antibodies.

These observations support that multiple LCMV strains and/or isolates could be detected using suitable molecular and immunodetection approaches.

Example 2

Hypoxia Reactivates LCMV from Persistent Infection

HeLa cells persistently infected with LCMV MX strain (HeLa-MX) were incubated at normoxic (21% O2) or hypoxic (2% O2) conditions for 48 h. A separate population of HeLa-MX cells were also treated with 1 mM of DMOG (a hypoxia mimicking agent) for 24 hours under normoxic conditions.

RT-PCR

Total cellular RNA was extracted with InstaPure reagent according to the manufacturer's instructions. Reverse transcription was performed with M-MuLV reverse transcriptase using random heptameric primers. Levels of viral gene expression were analyzed by quantitative real-time PCR on a StepOne™ Real-Time PCR System (Applied Biosystems, Foster City, Calif., USA.) using POWER SYBR® Green PCR Master Mix and the following gene-specific primers:

```
NP (246 base pair (bp) PCR product):
                                      (SEQ ID NO: 58)
Forward:  5'- GATCAGAAACAGTTCAAACAGGACT-3'

(SEQ ID NO: 59)
Reverse:  5'- GTCCCACACTTTGTCTTCATACTCT-3'

GP (251 bp PCR product):
                                      (SEQ ID NO: 60)
Forward:  5'- AACCAGTGCAGAACTTTTAGAGGTA-3'

(SEQ ID NO: 61)
Reverse:  5'- GCAAGTCTTCTAGTGAGGAACTTTG-3'

ZP (272 bp PCR product):
                                      (SEQ ID NO: 62)
Forward:  5'- CCTGTGAGAGTACAGAGACAAACCT-3'

(SEQ ID NO: 63)
Reverse:  5'- GATATCTTCAGCTTGGTTGGTAATG-3'

β-actin (236 bp PCR product):
                                      (SEQ ID NO: 64)
Forward:  5'- CCAACCGCGAGAAGATGA-3'

(SEQ ID NO: 65)
Reverse:  5'- GATCTTCATGAGGTAGTCAGT-3'
```

For each gene, fold induction was determined in comparison with value from normoxic control using β-actin as an endogenous control.

Figure 10A:
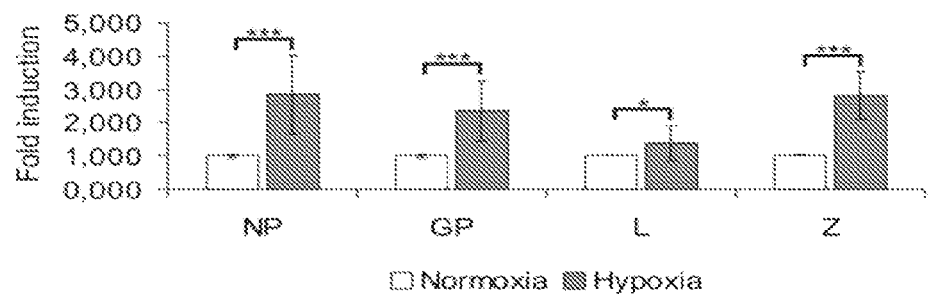
FIG. 10A is a histogram showing that hypoxia up-regulates LCMV gene expression. Fold induction was determined in comparison with the normoxic control. Values represent means of three separate experiments done in quadruplicates. Error bars denote the standard deviations. *$P<0.02$, ***$P<0.001$ (hypoxic (HY) vs. normoxic (NO)).
Figure 10B:
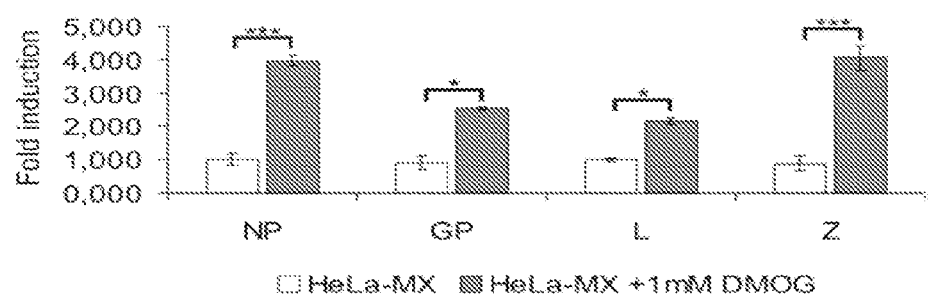
FIG. 10B is a histogram showing that DMOG treatment up-regulates LCMV gene expression. Values represent means of triplicate determinations in one representative experiment out of two, with error bars denoting standard deviations. *$P<0.05$, ***$P<0.001$ (DMOG vs. no DMOG).

As shown in FIGS. 10A and 10B, hypoxia and DMOG similarly increased expression of mRNA encoding all LCMV proteins tested (i.e., NP, ZP, and GP) relative to normoxia, as assessed by RT-PCR. No change was observed for the control (β-actin).

In order to prove that hypoxia influences virus genes at the transcriptional level, RNA ligase-mediated rapid amplification of 5' cDNA ends (RLM-RACE) was performed using the GeneRacer method, which allows for selective amplification of the 5' capped transcripts and eliminates non-capped genomic/antigenomic LCMV RNA templates.

Selective amplification of 5' capped transcripts of MX LCMV was carried out using the GeneRacer™ kit according to instructions of the manufacturer (Invitrogen, Life Technologies). LCMV-MX gene-specific primers employed in RLM-RACE on RNA isolated from normoxic and hypoxic HeLa-MX cells are listed below:

```
NP gene
5' RACE reverse primer:
CAAGGTCGGCAGCGAGAGACATCA        (SEQ ID NO: 66)

5' RACE nested reverse primer:
AGAAGGCTAGTTGCGTCCTTGATG        (SEQ ID NO: 67)

GP gene
5' RACE reverse primer:
GGCTGAACATGCATTGGGCATTGT        (SEQ ID NO: 68)

5' RACE nested reverse primer:
TAGGAGAAGGAAGCTGACCAATGC        (SEQ ID NO: 69)

L gene
5' RACE reverse primer:
TCCTGGACACACAACTCCGGACTCTA      (SEQ ID NO: 70)

5' RACE nested reverse primer:
ACAGCCACTTTTGTCTGCACTGTC        (SEQ ID NO: 71)

Z gene
5' RACE reverse primer:
CTTCGTAGGGAGGTGGTGGGCTTG        (SEQ ID NO: 72)

5' RACE nested reverse primer:
AGTTCAGTGGACCGAGATAGGTGGT       (SEQ ID NO: 73)
```

β-actin was employed as internal standard and control of RLM quality using the primers included in the kit. Resulting PCR fragments were run on 1.5% agarose gels and their specificity was verified by sequencing and by reamplification with independent gene-specific primers. The intensity of bands corresponding to individual PCR products was evaluated with GeneTools Software from Syngene. Amount of gene-specific PCR products was semi-quantitatively expressed as the ratio of the intensity of each LCMV-specific band to the intensity of the corresponding β-actin internal standard. Commercial HeLa total RNA included in the kit was used for β-actin amplification as a control for activity of CIP and TAP enzymes.

Figure 10C:
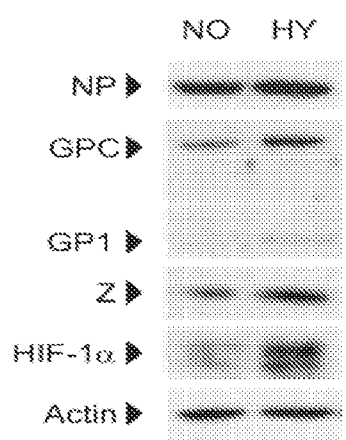
FIG. 10C is an image of an immunoblot showing that hypoxia up-regulates LCMV protein expression. Actin is shown as a control for loading and transfer efficiency. Detection of HIF-1alpha served as a control for the induction of cellular response to hypoxia. One representative of at least three independent experiments with similar results is shown.
Figure 10D:
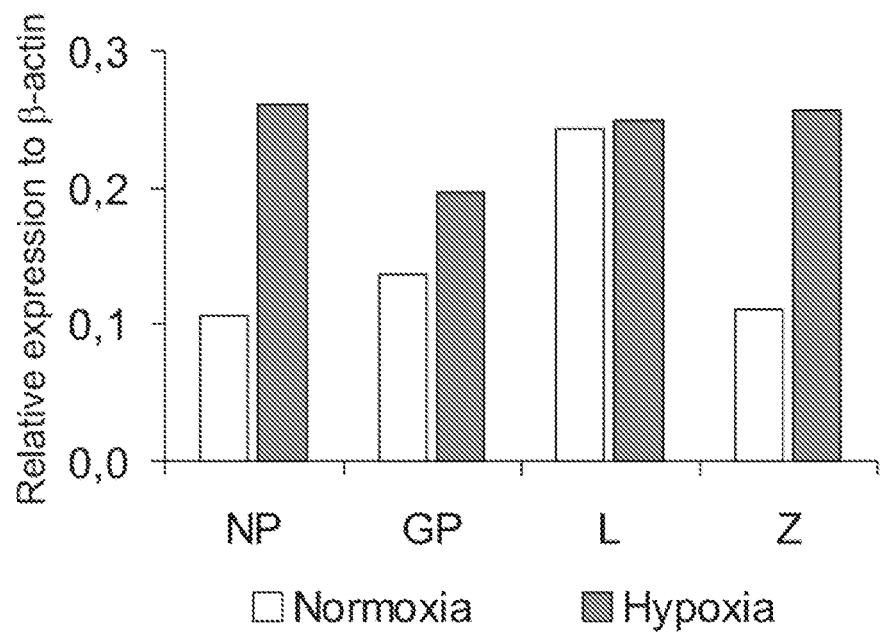
FIG. 10D is a bar graph showing relative expression levels of various LCMV genes under normoxic and hypoxic conditions as assessed by RLM-RACE.

As shown in FIG. 10D, the semi-quantitatively evaluated results of the RLM-RACE carried out on total RNA isolated from hypoxic (2% O2) versus normoxic HeLa-MX cells were consistent with the above described RT PCR data (see FIG. 10A) suggesting that hypoxia affects the virus transcription.

Immunoblotting

One million HeLa-MX were plated into Petri dishes, left to attach overnight and then incubated for 48 h under normoxic or hypoxic conditions. Cells were disrupted in lysis buffer (50 mM Tris, pH 7.5, 150 mM NaCl, 1% Triton X-100, 0.1% sodium deoxycholate and 1× Complete protease inhibitor cocktail [Roche, Mannheim, Germany] in PBS) and total protein concentrations were determined by BCA assay (Pierce, Rockford, Ill., USA) according to manufacturer's instructions. Total protein extracts (100 µg/lane) were separated by SDS/PAGE under reducing conditions, blotted onto PVDF membrane (Immobilon™, Millipore, Billerica, Mass., USA), and detected by using specific antibodies against NP (mouse monoclonal antibody M59), Z protein (mouse monoclonal antibody MJ3), GP1 (anti-peptide polyclonal antibody), HIF-1alpha or alpha-actin followed by appropriate secondary antibody conjugated with horseradish peroxidase. All immunoblots were developed with the ECL detection system.

As shown in FIG. 10C, hypoxia increased expression levels of all LCMV proteins tested (i.e., NP, ZP, and GP) relative to normoxia. No change was observed for the control (actin).

Example 3

LCMV Reactivated by Hypoxia are Infectious

Filtered medium from HeLa-MX cultured under normoxia or hypoxia for 48 h was used to infect non-infected HeLa cells. These cells were then cultivated in normoxic conditions, passaged, and then assessed for viral replication.

Figures 11A, 11B, 11C:
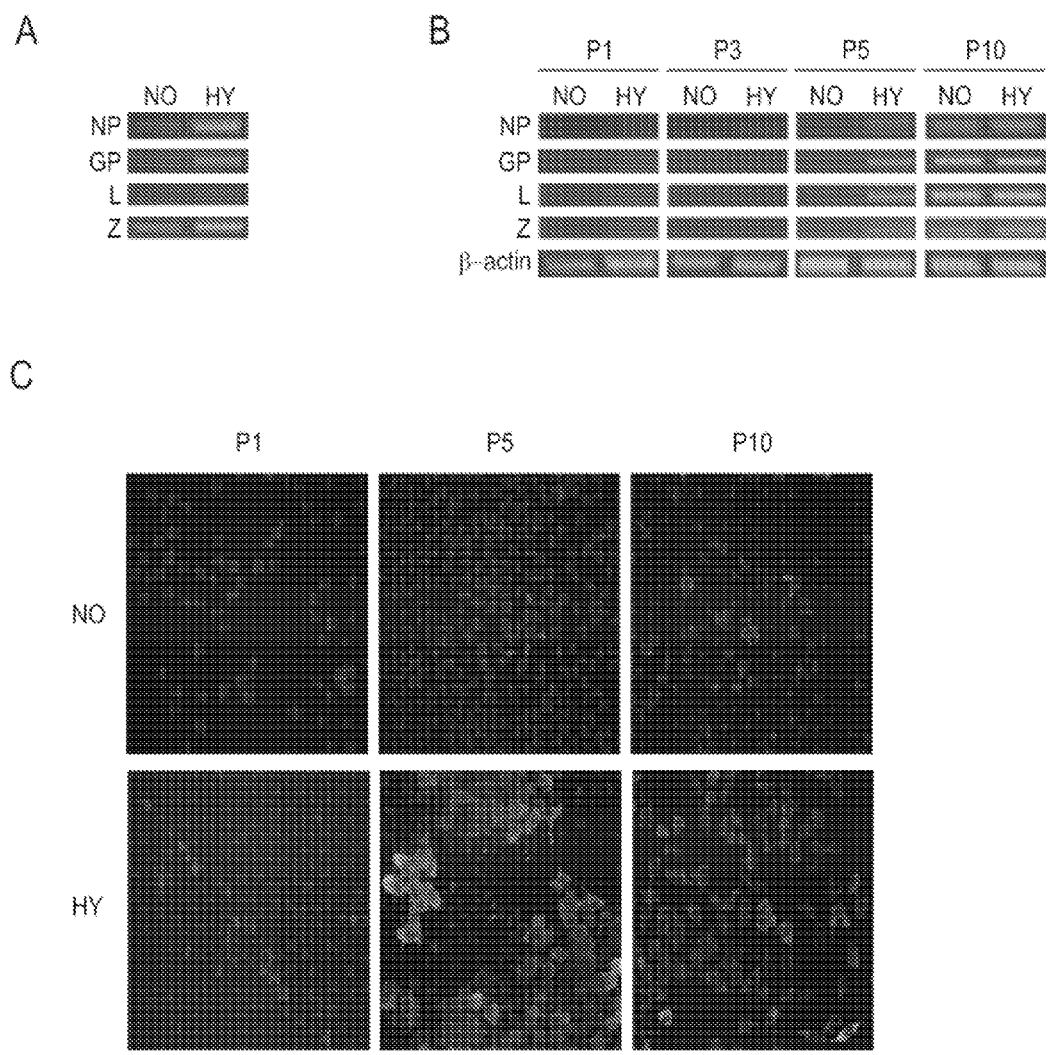
FIG. 11A is an image of gel confirming the presence of LCMV genome in the medium from HeLa-MX cells cultured under normoxia (NO) and in the medium from cells cultured under hypoxia (HY) as detected by RT-PCR.
FIG. 11B is an image of a gel showing LCMV gene expression in cells infected using the medium from HeLa-MX cells at passage (P)1, P3, P5, and P10, as assessed by RT-PCR.
FIG. 11C is an image of cells infected using the medium from HeLa-MX cells. Cells were stained for LCMV. A nuclear stain was also used. Cells were stained at P1, P3, and P10. 20-times magnification was used. Data is representative of two independent experiments.

The presence of LCMV genome in the medium from HeLa-MX cells cultured under normoxia (NO) and under hypoxia (HY) was confirmed by RT-PCR method (see FIG. 11A). In addition, the spread of infection in the HeLa populations infected with indicated medium was followed by RT-PCR analysis in the first 5 passages and then in tenth passage (see FIG. 11B). The progress of infection was monitored also by immunofluorescence detection of viral nucleoprotein in recipient cells under 20× magnification (see FIG. 11C). The experiment was repeated twice, each time showing similar results. As shown in FIGS. 11A-11C, hypoxia increases the infectivity of LCMV.

The data shown in Examples 2 and 3 demonstrate that hypoxia can increase expression of viral NP, Z and GP (including appearance of GP1) genes and proteins in culture (Example 1) and can trigger formation of infectious virus particles (Example 2).

These data support a rationale for diagnostic detection of LCMV in subjects at risk for hypoxia with hypoxia virus genes, antigens of antibodies against these antigens and their combinations Example 4

Generation of Antibodies that Bind Specifically to LCMV NP

Mouse monoclonal antibody M59, M166 and M87 are specific for the LCMV NP. These antibodies were prepared using the hybridoma technique (Kohler and Milstein 1975).

BALB/c mice were immunized with three doses of 5×10⁶ HeLa-MX cells and their splenocytes were fused with NS-0 myeloma cells. Hybridomas were selected in DMEM-HAT medium containing hypoxanthine, aminopterin and thymidine, and screened for the specific reactivity towards NP by differential ELISA using cell extract of HeLa and HeLa/MX cells as an antigen. Positive hybridoma cultures were cloned by limiting dilution, expanded and used for MAbs production.

All of M59, M166, and M87 bound NP from LCMV MX and cross-reacted with NPs of other LCMV strains.

Example 4A

Deposit of M166

The hybridoma cell line expressing mouse monoclonal antibody M166 was deposited with the Belgian Coordinated Collections of Microorganisms (BCCM) at Ghent University, Belgium (Universiteit Gent, Vakgroep Moleculaire Biolgie-Plasmidicollectie (BCCM™/LMBP), under accession number LMBP 9216CB.

Example 4B

Characterization of M87 Variable Region Sequence

Figure 12A:
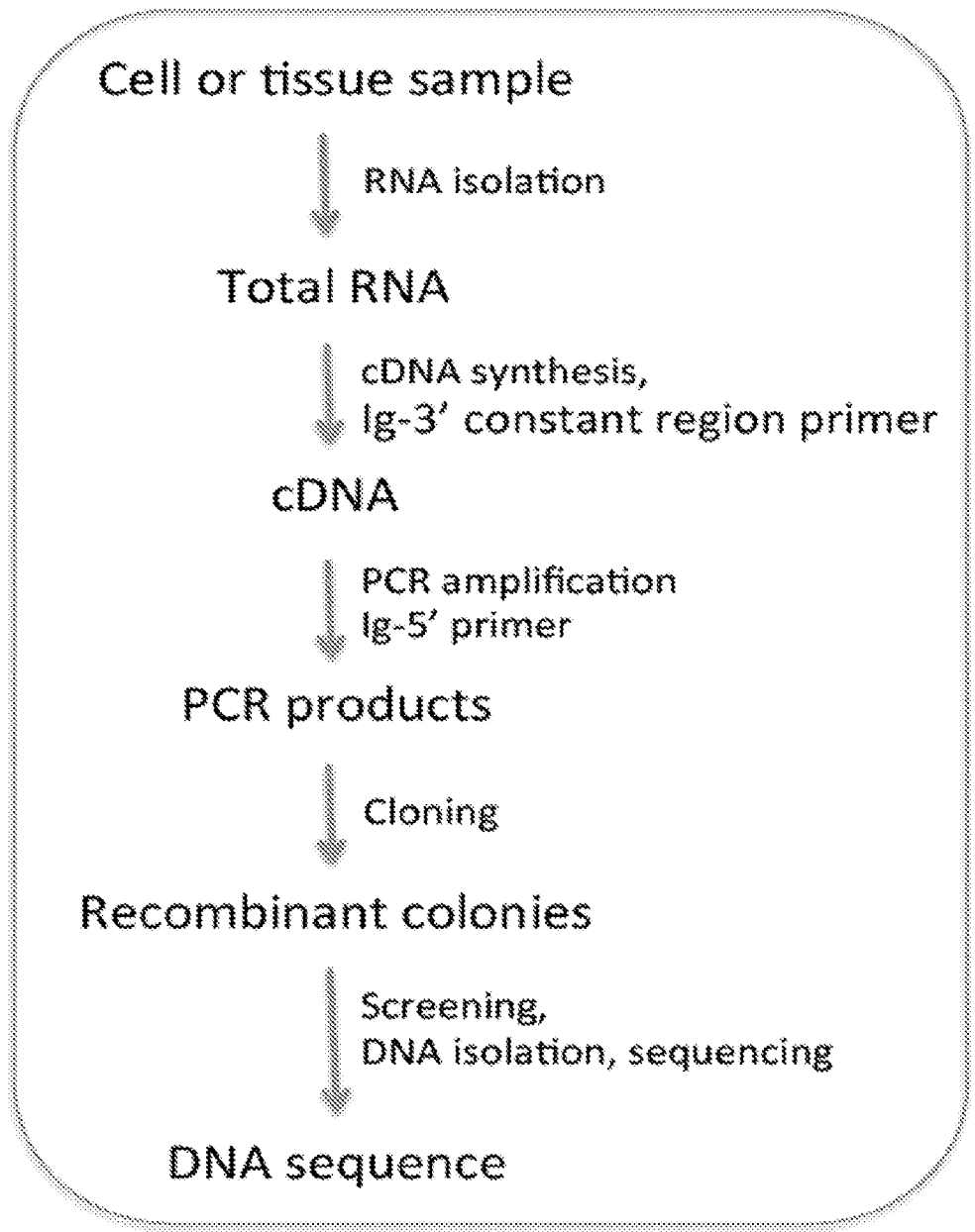
FIG. 12 A is a diagram illustrating a protocol used to characterize the sequence of the variable regions of antibody heavy chains.
FIG. 12B shows the amino acid sequence (SEQ ID NO: 90) of the variable region of the heavy chain of MAb M87. Yellow shading indicates a signal peptide sequence. Green shading indicates hypervariable regions.
FIG. 12C illustrates structure of the heavy chain of MAb M87.
Figures 12B, 12C:
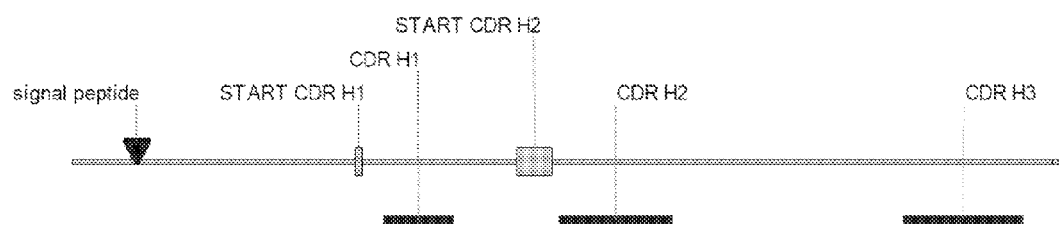
Figure 13:
FIG. 13 is an image of an immunoblot confirming the presence of anti-NP antibodies in sera of women who had spontaneous abortion. Anti-NP antibodies in human sera were detected by immunoprecipitation.
Figures 14A, 14B, 14C:
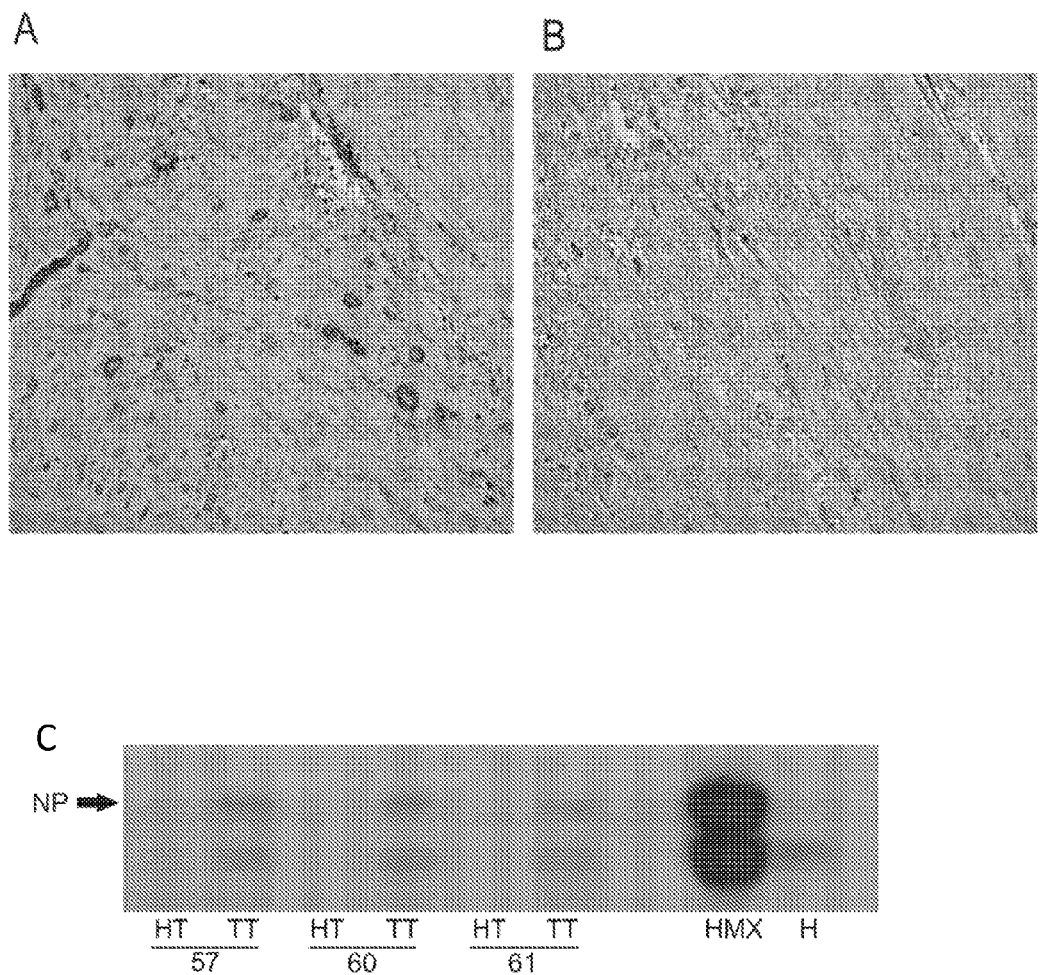
FIG. 14C is an image of an immunoblot showing immunodetection of LCMV NP in tissue from human RCC subjects by immunoprecipitation and subsequent immunoblotting with NP-specific monoclonal antibody. HT=healthy tissue, TT=tumor tissue, HMX=HeLa/MX (positive control), H=HeLa (negative control).

The amino acid sequence of the M87 heavy chain was determined, as follows and as depicted in FIG. 12A. RNA was isolated from 1 million M87 hybridoma cells and subjected to reverse transcription using random hexameric primers. The heavy chain variable region was amplified from the resulting cDNA using a degenerated forward primer designed to be complementary to the signal peptide/leader sequence (see FIG. 12) and a reverse primer complementary to the CH1 region of the constant domain (see FIG. 12). Amplification was done using a high fidelity polymerase and PCR product of the expected size (cca 400 bp) was separated by electrophoresis and isolated from the gel. A linear PCR amplicon was ligated into pJet1.2 vector, which was then transformed competent *Escherica coli*. Resulting transformed cells were screened and selected colonies were verified by restriction enzyme cleavage and sequencing. The sequence of the M87 heavy chain variable region was determined to be:

mdsrinlvflylilkgvqcd-vqlvesggglvqpggsrklscaasgfif-ssfgmhwvrqapekglewvayissgss tlhyadtvkgrftisrdnp-kntlflqmklpslcygllgsrnlshrllsqndtpirlsigpwklgi (SEQ ID NO: 74)

Within the M87 heavy chain variable region (SEQ ID NO: 74), mdsrinlvflylilkgvqc (SEQ ID NO:75) is a signal peptide sequence; gftfssfgmhwv (SEQ ID NO:76) is CDR1; issgsstl-hyadtvkgrft (SEQ ID NO:77) is CDR2; and hrllsqndtpirlsigp (SEQ ID NO:78) is CDR3. Annotated versions of SEQ ID NO:74) are provided in FIGS. 12B-12C.

Example 5

Generation of Antibodies that Bind Specifically to LCMV GP1

Polyclonal antibody against LCMV MX GP1 were raised, as follows. Potential B-cell epitopes were identified using the complete sequence of the GPC LCMV MX using several available programs. Peptide RSGWGWAGSDGKTT (aa 205-218 of SEQ ID NO: 41) (SEQ ID NO:89) mapping within a region of the GP1 was chosen for production of GP1-specific polyclonal antibodies. Affinity purified rabbit polyclonal antibody was tested by immunoprecipitation and Western blotting.

Example 6

Generation of Antibodies that Bind Specifically to LCMV ZP

Mouse monoclonal antibody MJ3 binds specifically to LCMV ZP. Antibodies were generated using the hybridoma technique (Kohler and Milstein, supra). Briefly, BALB/c mice were immunized with two doses of 5×10⁶ HeLa-MX cells and boosted with 100 µg GST-Z protein bound to Glutathione Sepharose 4B. Fusion of spleen cells with Sp2/0 myeloma cells was carried out 3 days later. Hybridomas were selected in DMEM-HAT medium and monoclonal antibodies produced by the hybridomas were screened for the specific reactivity towards Z protein in GST-Z vs GST and HeLa-MX vs. noninfected HeLa cells by ELISA and immunoblotting. The hybridoma culture (MJ3) was subcloned by limiting dilution, expanded and used for the MAb production.

MAb MJ3 was shown to react with Z protein using different immunodetection methods.

Example 6A

Deposit of MJ3

The hybridoma cell line expressing mouse monoclonal antibody MJ3 was deposited with the Belgian Coordinated Collections of Microorganisms (BCCM) at Ghent University, Belgium (Universiteit Gent, Vakgroep Moleculaire Biolgie-Plasmidicollectie (BCCM™/LMBP), under accession number LMBP 9217CB.

Example 7

Detection of Anti-LCMV NP Antibody in Human Subjects

Serum samples were obtained from (i) women with spontaneous abortions without diagnosed cause; (ii) women with full-term gravidity; and (iii) oncology patients with renal cell carcinoma (RCC) tumors. Anti-LCMV antibodies in human sera were analyzed by immunoprecipitation and subsequent immunoblotting with NP-specific monoclonal antibody.

The approach employed in this example is very sensitive and enables detection of NP-specific antibodies produced during both acute and chronic/persistent infections. Briefly, protein G-Sepharose (50% slurry) was washed with PBS and mixed with whole cell lysate from HeLa-MX cells to preclear non-specifically binding proteins. 10 μl of human serum in 190 μl PBS containing 10% FCS was added to 100 μl precleared cell extract. Immunocomplexes were then allowed to form at 4° C. overnight. The resulting immunocomplexes were precipitated by adding 30 μl of washed Protein G-Sepharose slurry for one hour at 4° C. Beads were then washed five times in PBS, subjected to SDS-PAGE, and transferred onto a polyvinylidene difluoride membrane. Membranes were probed with purified MAb conjugated with horseradish peroxidase. After an additional washing step, immunoblots were visualized using the ECL detection system.

As shown in Tables 1A-1B, seroprevalence of NP antibodies in women with abortions was by 19.4% higher compared to control.

TABLE 1A

Detection of Anti-LCMV NP Antibodies in Human Female Subjects that Experienced Spontaneous Abortion

| | Women with abortion | | women without abortion | |
|---|---|---|---|---|
| | number | % | number | % |
| positive sera | 34 | 75.6 | 18 | 56.2 |
| negative sera | 11 | 24.4 | 14 | 43.8 |
| total | 45 | 100 | 32 | 100 |

Detected antibodies are also shown as immunoblot in FIG. 13.

As shown in Table 4, very high seroprevalence of NP antibodies was also observed for patients with RCC tumors.

TABLE 1B

Detection of Anti-LCMV NP Antibodies in Subjects with RCC Tumors

| | Oncology patients | |
|---|---|---|
| | number | % |
| Positive sera | 25 | 89.3 |
| negative sera | 3 | 10.7 |
| Total | 28 | 100 |

Example 7B

Detection of NP-Specific Antibodies in Human Sera by Tandem Mass Spectrometry One human serum shown to be positive for NP by immunoprecipitation and subsequent immunoblotting with NP-specific monoclonal antibody was immunoprecipitated as described in Example 7. After washing, immunocomplexes were eluted with citrate buffer (pH 3). The final pH of eluate was adjusted by adding of 1M Tris pH 8.5. Subsequently, eluates containing immunocomplexes were subjected to tandem mass spectrometry. Briefly, samples were reduced (10 mM dithiothreitol), alkylated (55 mM iodoacetamide) and digested by 20 μg/ml trypsin (Promega, Madison, Wis.) in 50 mM ammonium bicarbonate overnight at 37° C. Resulting peptides were transferred to microplate and dried by lyophilization. The extracted peptide mixture was dissolved in 20 μl of 2% acetonitrile in water with addition of 0.1% of formic acid and separated by a nanoAcquity HPLC system (Waters, Milford, Mass.) as described previously (Henrychová et al., 2008). The data acquisition was performed in data-dependent manner for the time of the separation collecting up to 3 MS/MS events at the same time. Data were processed by ProteinLynx Global Server v. 2.4 (Waters) that provided background subtraction (polynomial order 5 and threshold 35%), smoothing (Savitzky Golay, twice, over three channels) and centroiding (top, 80%, minimal peak width at half height 4). Resulting data were searched against UniProt_LCMV database under the following criteria: fixed carbamidomethylation of Cys, variable Met oxidation, tryptic fragments with 1 miss cleavage, peptide mass tolerance 50 ppm, and fragment mass tolerance 0.05 Da. Results were validated by the identification of three or more consecutive fragment ions from the same series. The protein assignments with at least two matching peptides to the theoretical sequences were considered as positive identification.

As shown in Table 2, in analyzed samples was identified LCMV NP.

TABLE 2

| Identification of NP in Immunocomplexes by UPLC-MS | | | | | | |
|---|---|---|---|---|---|---|
| Sample | Accession | Description | mW (Da) | pI (pH) | PLGS Score | Peptides |
| MSE3 | C3VVN3 | Nucleoprotein OS Lymphocytic choriomeningitis virus | 62399 | 8.6614 | 65.510 | 4 |
| 2. processing | Q9YPM1 | Glycoprotein 1 Fragment OS Lymphocytic choriomeningitis virus strain WE | 15535 | 8.4294 | 282.26 | 1 |
| | C3VVN3 | Nucleoprotein OS Lymphocytic choriomeningitis virus | 62399 | 8.6614 | 66.551 | 3 |
| MSE5 | Q86867 | S RNA product protein Fragment OS Lymphocytic choriomeningitis virus | 1596 | 6.2774 | 250.47 | 1 |

This result clearly proved that tested human serum contains NP-specific antibodies.

Example 8

Immunodetection of LCMV Antigens in Tissue from Human RCC Subjects

LCMV antigens were detected in RCC specimens by immunochemistry. Briefly, dissected tissues were fixed in 4% neutral buffered formalin and embedded in paraffin according to the standard histological procedures. Four-μm sections were placed on polylysine-coated slides, de-waxed and rehydrated. The slides were first subjected to tissue pretreatment procedure at 125° C. for 5 min in target retrieval solution (Pascal pressure chamber, DakoCytomation, Carpinteria, Calif.). The rest of the immunostaining procedure was performed using the Dako Cytomation EnVision®+System-HRP (DAB) according to the manufacturer's instructions: a) peroxidase and protein block (10 min each); b) incubation for 1 h with primary antibody M59 specific for the NP (undiluted hybridoma medium) or PBS (negative control); c) incubation for 30 min with peroxidase-conjugated goat anti-mouse antibody diluted 1:1000 in antibody diluent (DakoCytomation). Staining was visualized with DAB solution for 1 min with 3,3'-diaminobenzidine as a chromogenic substrate. The slides were washed in PBS with 0.1% Tween-20 for 10 min after the step a, 2 times for 10 min after steps b and c, and three times in distilled water after visualisation with DAB. All incubations and washings were carried out at room temperature. Finally, the sections were counterstained with Mayer's hematoxylin, washed for 5 min and mounted in DePeX (Serva, Heidelberg, Germany). The stained sections were examined with Leica DM4500B microscope and photographed with Leica DFC480 camera.

As shown in FIG. 14A-B, LCMV antigens were detected in tissue from RCC subjects.

In addition, LCMV antigens were detected in RCC specimens by immunoprecipitation and subsequent immunoblotting with NP-specific antibody M87. Briefly, 100 mg of frozen tissue specimens were homogenized in ice-cold lysis buffer (1% Triton X-100; 150 mM NaCl; 50 mM Tris, pH 7.5; 0.5% Nonidet P-40; 50 mM NaF) containing inhibitors of proteases (Roche Applied Science, Mannheim, Germany). The insoluble material was removed by centrifugation for 15 min at 12,000 g at 4° C. MAb M87 (1.5 ml cultivated medium) was bound to 30 μl 50% suspension of protein G-Sepharose in PBS for 2 hrs at RT. Tissue protein extract (200 μl) was pre-cleared with 20 μl of 50% suspension protein G-Sepharose and added to bound MAb. Immunocomplexes were then allowed to form at 4° C. overnight. Beads were then washed six times in PBS, subjected to SDS-PAGE, and transferred onto a polyvinylidene difluoride membrane. Membranes were probed with purified MAb M87 conjugated with horseradish peroxidase. After an additional washing step, immunoblots were visualized using the ECL detection system.

As shown in FIG. 14C, LCMV NP was detected in tissue from RCC subjects using MAb M87.

Example 9

Analysis of NP-Specific Monoclonal Antibodies

Mouse monoclonal antibodies M59, M166, and M87, specific for the NP LCMV were prepared by the hybridoma technique (Kohler and Milstein 1975). Briefly, BALB/c mice were immunized with three doses of $5\cdot10^6$ HeLa-MX cells and their splenocytes were fused with NS-0 myeloma cells. Hybridomas were selected in DMEM-HAT medium containing hypoxanthine, aminopterin and thymidine, and screened for the specific reactivity towards NP by differential ELISA using cell extract of HeLa and HeLa/MX cells as an antigen. Positive hybridoma cultures were cloned by limiting dilution, expanded and used for MAbs production. Each of MAbs M59, M166, and M87 were shown to cross-react with NPs of other LCMV strains.

MAb isotypes were determined by ELISA using affinity purified rabbit anti-mouse IgG1, IgG2a, IgG2b, IgG3, IgM and IgA antibodies (Mouse Monoclonal Antibody Isotyping Reagents, Sigma) according to the instructions of the manufacturer. M59 and M166 MAbs were found to be of IgG2a isotype and M87 MAb was of IgG1 isotype.

The antibodies were further tested in different immunodetection methods. M59 was found to react with NP in ELISA, immunoprecipitation, and immunohistochemistry; M166 was found to react with NP in ELISA, IFA, and immunoprecipitation; and M87 was found to bind to NP in ELISA, immunoprecipitation, IFA, and immunoblotting. These data suggest that the antibodies recognize different epitopes of NP molecule, with M59 and M166 being directed to a conformational epitope and M87 binding to linear epitope. Differential epitope specificity of these antibodies was proven by competitive binding assay.

Briefly, MAb was first purified by affinity chromatography on Protein A/G speharose and labeled with NHS-LC-Biotin (Pierce) according to the instructions of the manufacturer. Extract from HeLa-MX cells was adsorbed on microplate wells at a concentration corresponding to 50% of maximal binding of labelled MAbs. Coated plates were washed and saturated with 10% FCS in PBS. Serial fivefold dilutions of purified MAbs in 30 μl and a constant amount of biotinylated MAb in 30 µl were added and incubated overnight at 4° C. The plates were washed and peroxidase-labelled streptavidin (Pierce) was used as a detector.

Figure 15A:
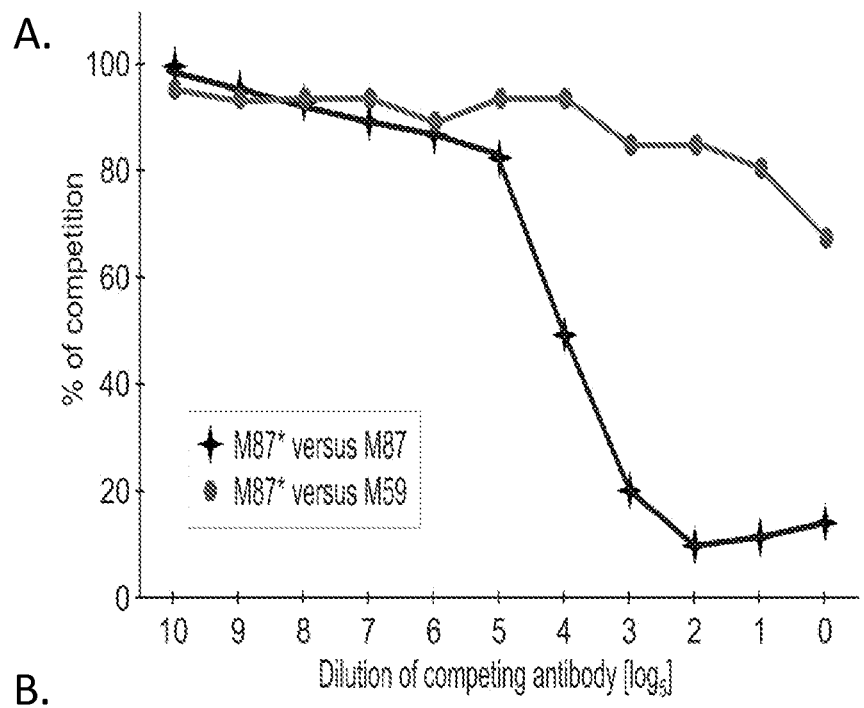
FIGS. 15A and 15B are graphs illustrating the results of competitive binding studies between M87 and M59 antibodies.
Figure 15B:
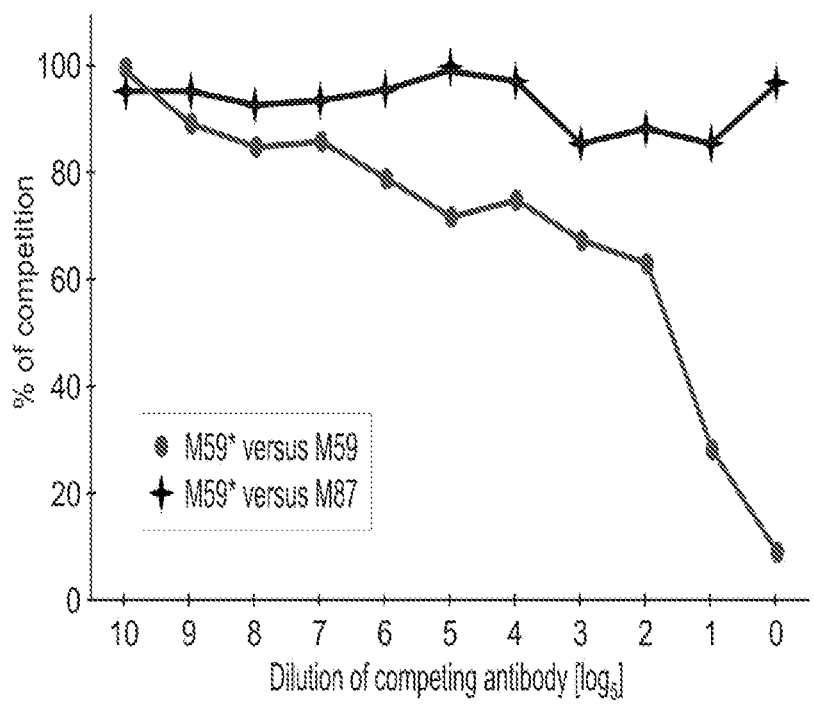
Figure 16:
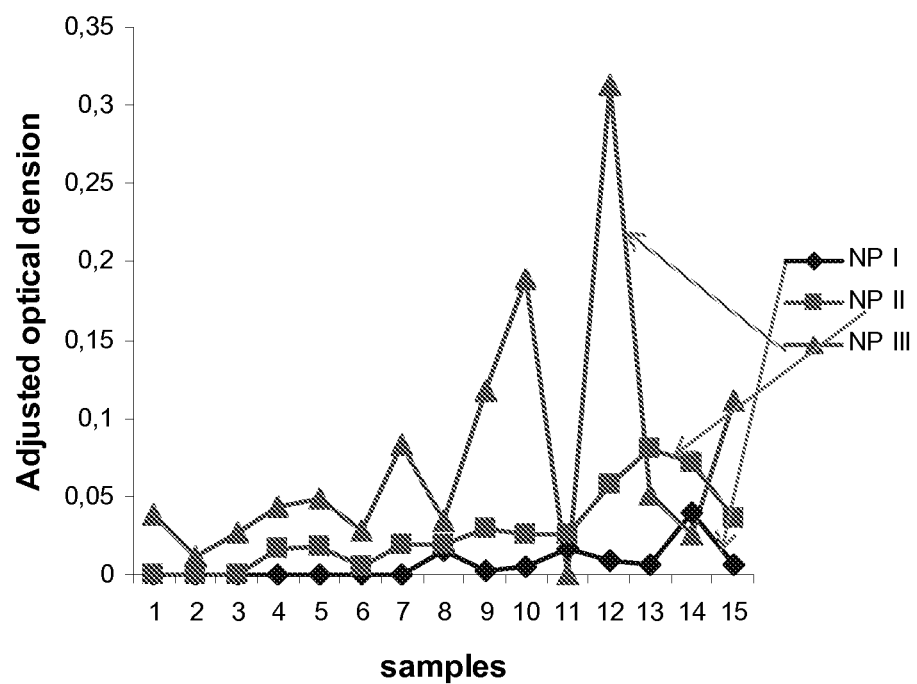
FIG. 16 is a line graph showing epitope binding of NP-specific antibodies to NP fragments.

Results are illustrated in FIGS. 15A and 15B. These are graphs illustrating an examination of the competitive binding between M87 and M59 MAbs. Biotin-labelled purified antibodies (*) were allowed to bind in the presence of increasing amounts of non-labelled competitive antibodies. The extent of binding of the labelled antibody in the presence of the non-labelled competitor was expressed as percentage of binding in the absence of the competitor. Dilution 0 corresponds to 10 µg/well of non-labeled competing antibody. The results show only homologous competition, but no heterologous hindrance of binding of the labeled competitor was observed, suggesting that the MAb bind to non-overlapping epitopes.

Example 10

Virus Response to Hypoxia: LCMV Arenavirus as a Paradigm

Physiological context of the virus-infected cells can markedly affect multiplication and spread of the virus progeny. Mainly during persistent infection, when the virus strongly depends on host cell and usually does not disturb its vital functions, microenvironmental stresses such as hypoxia can uncouple the intimate virus-host relation and escalate the virus pathogenesis. Accumulating evidence suggests that hypoxia-induced molecular responses governed by HIF transcription factor modulate gene expression of viruses that pass through a DNA stage, contain HRE in their promoters and replicate in the nucleus. We could show for the first time, that hypoxia can also influence the outcome of persistent cytoplasmic RNA virus infection. As a model, we used lymphocytic choriomeningitis virus (LCMV) which can persist in different cell types without perturbing their integrity and causes mostly inaparent infections. It is therefore considered innocent, although LCMV-associated abortions and fatal LCMV infections in transplant recipients warn that it can be dangerous. MX strain of LCMV replicates in a persistent mode in human HeLa cells and spreads in a cell-to-cell manner in absence of extracellular infectious virions. Exposure of MX-infected HeLa cells to chronic hypoxia led to increased virus RNA transcription and higher levels of the viral proteins via a HIF-1α-dependent mechanism. Hypoxia also enhanced formation of infectious virions capable to transmit LCMV infection via cell-free medium. This hypoxia-induced LCMV "reactivation" might have health-compromising consequences, e.g. for developing fetus or receiver of transplant from asymptomatic donor.

Example 11

Cloning and Expression of Recombinant LCMV-NP-Fragments

Three overlapping fragments of LCMV (MX)-NP cDNA were cloned by PCR using the plasmid pBluescript-NP as a template, numbers in parentheses show positions with respect to published NP sequence of MX strain (GenBank accession number Y16308, Reiserova et al. 2001).

Fragment I containing amino acids 1-205 was amplified using the primers designated NPMXF1S 5'-CC GAATTCATGTCTCTGTCCAAGGAAGTCA-3' (46-67) (SEQ ID NO:79) and NPMXF1A 5'-GG CTCGAGGTAAAGCAGACCAAGGTCTGTG-3' (660-639) (SEQ ID NO:80);

Fragment II with amino acids 198-391 was amplified with the primers NPMXF2S 5'-GG GAATTCCTCACAGACCTTGGTCTGCTTT-3' (637-658) (SEQ ID NO:81) and NPMXF2A 5'-CC CTCGAGCACTGGATCATTGAACCTACCC-3' (1218-1197) (SEQ ID NO:82); and Fragment III containing the amino acids 384-558 was obtained by amplification with the primers NPMXF3S 5'-CC GAATTCGAGGGTAGGTTCAATGATCCAG-3' (1195-1226) (SEQ ID NO:83) and NPMXF3A 5'-C CTCGAGTTAGAGTGTCACAACATTTGGTC-3' (1722-1700) (SEQ ID NO:84). All the primers were designed with EcoRI and Xho I restriction sites (underlined), respectively. PCR reactions were performed using the primers listed above and EXT DNA polymerase (Finnzymes, Oy, Finland). Following an initial denaturation at 94° C. for 3 min, the amplification program was set as follows: denaturation at 94° C. for 30 s, annealing at 60° C. for 40 s, and extension at 72° C. during 1 min 20 s for a total of 35 cycles, and finally 7 min at 72° C. PCR products were purified on a 1.2% agarose gel using the Wizard® SV Gel & PCR clean-Up System (Promega, USA) and subcloned into either pBluescript SK(+) (Stratagene, USA) linearised with EcoRV and tailed with dT for T-A cloning or into pGEM®-T vector (Promega, USA). Next, all three fragments were cloned in-frame with glutathione S-transferase into pGEX-4T-1 (Amersham Pharmacia Biotech AB, Sweden) using EcoRI and XhoI restriction enzymes. To produce GST-fusion proteins, verified plasmid constructs (designated pGEX-4T1-NPI, pGEX-4T1-NPII, pGEX-4T1-NPIII) were transformed into E. coli BL21-CodonPlus (DE3)-RIPL (Stratagene, USA) competent cells, and induced with 0.2 mM IPTG (Sigma-Aldrich, USA, USA) for 3 hours.

Example 12

Purification of GST-Tagged Fusion Proteins

Induced cultures of E. coli were pelleted by centrifugation, resuspended in ice-cold lysis buffer STE (10 mM NaCl, 10 mM Tris-HCl, 1 mM EDTA in 1×PBS), pH 8 and incubated on ice for 15 min with lysozyme (Serva, Germany) in the final concentration of 0.4 mg/ml. Before sonication of bacterial cells (2×30 s) 10% Sarcosyl (Sigma-Aldrich, USA, USA) in STE to final concentration of 1.5% and 1M DTT (Sigma-Aldrich, USA, USA) to final concentration of 5 mM was added to cell suspension. The insoluble material was removed by centrifugation for 15 min at 12,000 g at 4° C. The appropriate volume of the 50% slurry of Glutathione Sepharose 4B (Amersham Pharmacia Biotech) equilibrated with STE, pH 8 was added to bacterial lysate and incubated overnight with gentle agitation at 4° C. Next day, the fusion proteins bound on Glutathione Sepharose 4B were extensively washed with ice-cold STE, pH 8 and eluted with 15 mM reduced glutathione (Merck) in 50 mM Tris-HCl, pH 8.0 at room temperature. The yield of fusion proteins in purified samples was determined by SDS-PAGE and visual comparison to defined concentration of BSA.

Example 13

NP-IgG ELISA-1

Microplate wells were coated overnight at 37° C. with the purified fusion proteins GST-NPI, GST-NPII, GST-NPIII and GST (50 ng/well) diluted in 0.05M sodium carbonate-bicarbonate buffer (pH 9.6). After blocking with 10% skimmed milk in PBS+0.1% Tween 20, the coated wells were incubated with serum samples (50 ml aliquots), which were diluted in two-fold steps starting with 1:20 in blocking solution and incubated 1 hours at room temperature. Plates were washed four times with PBS-0.1% Tween 20 and incubated with peroxidase-conjugated goat anti-human IgG (Sigma) diluted 1:35000 in blocking solution for 45 minutes at room temperature. After washing, substrate solution (10 ml of Mc Ilweine buffer pH 5.5 (100 mM Na2HPO4, 40 mM citric acid), 10 mg o-phenylenediamine (Sigma), 10 µl of 30% H2O2) was added into each well and incubating for 5-10 min in a dark place. Reaction was stopped by adding of 2M H2SO4 and optical density was measured for absorbance at 492 nm. The adjusted OD was calculated by subtracting the OD of the negative antigen-coated wells from that of corresponding wells.

Example 14

Epitope Mapping on Recombinantly Expressed GST-, NPI, GST-NPII, and GST-NPIII by Positive Human Sera To determine epitopes present on NP recognized by NP-specific serum antibodies, ELISA according to the protocol described in Example 13 was performed. 15 serum samples that were verified to be positive by immunoprecipitation method were used.

As shown in FIG. 16, anti-NP serum antibodies preferentially recognized epitopes located on the fragment III of NP (containing the amino acids 384-558), while small fraction of antibodies reacted also with epitope located on the fragment II (amino acids 198-391).

Example 15

NP-IgG ELISA-2

Detection of nucleoprotein (NP)-specific serum Abs was carried out by following method. 96-well polystyrene plates were coated with NP-specific monoclonal antibody M87 at concentration 6 μg/ml diluted in a 0.05M sodium carbonate-bicarbonate buffer (pH 9.6) at 4° C. overnight. Plates were blocked for 1.5 h with 10% milk (200 μl per well) in PBS with 0.1% Tween 20 (PBS-T) and afterward were incubated for 1 h with the cell lysate (HeLa cells persistently infected with LCMV MX and uninfected HeLa cells) diluted 1:300 in blocking solution. On a parallel plate human serum samples were diluted 1:20 and 1:60 in blocking solution. A total of 50 μl per well of diluted serum samples was transferred to NP-saturated plates, followed by incubation for 1 hour. Finally, the plates were incubated for 45 min with HRP conjugated goat anti-human IgG (Fc-specific) Ab (SIGMA) diluted 1:35000 in blocking solution. HRP was detected by OPD color reaction, which was stopped by adding 50 μl of 2M H2504. Optical density was measured for absorbance at 492 nm. All steps were carried out at room temperature. Between each step the plates were washed four times with PBS-T. The adjusted OD was calculated by subtracting the OD of the negative antigen-coated wells from that of corresponding wells.

Alternatively, was as antigen used purified recombinant LCMV NP at concentration 4 μg/ml.

To find suitable internal positive and negative controls, human sera were analyzed by immunoprecipitation and subsequent immunoblotting with NP-specific monoclonal antibody (see Example 7). Later, one of the sera was chosen as a negative control and another as was selected as a positive control for subsequent testing. 25 sera which have been proved negative with the immunoprecipitation test, were subsequently analyzed in NP ELISA and the adjusted OD values obtained were then expressed as percent positivity (PP) of the internal positive control by finding the average adjusted OD value of two replicates divided by the median value of the adjusted OD values of the four replicates of the positive control multiplied by 100. The ELISA cut-off value, which would serve as a threshold between the positive and negative sera samples was determined as the mean PP value obtained with this 25 samples plus two standard deviations.

The cut-off value was determined to be 4.2% using this method and was used for subsequent calculation.

Example 16

Detection of Anti-LCMV NP Antibody in Human Samples by NP-IgG ELISA-2

Serum samples were obtained from (i) women with spontaneous abortions without diagnosed cause; (ii) women with full-term gravidity; and (iii) oncology patients with renal cell carcinoma (RCC) tumors. Anti-LCMV antibodies in human sera were tested under the conditions described in Example 15 and PP values were determined and are shown in Table 3.

TABLE 3

Detection of Anti-LCMV NP Antibodies in Human Female Subjects that Experienced Spontaneous Abortion

| | Women with abortion | | Women without abortion | |
|---|---|---|---|---|
| | number | % | number | % |
| positive sera | 11 | 23.9 | 13 | 11.8 |
| negative sera | 35 | 76.1 | 97 | 88.2 |
| total | 46 | 100 | 110 | 100 |

As shown in Table 3, seroprevalence of NP antibodies in women with abortions was by 12.1% higher compared to control. As shown in Table 4, very high seroprevalence of NP antibodies was also observed for patients with RCC tumors.

TABLE 4

Detection of Anti-LCMV NP Antibodies in Subjects with RCC Tumors

| | Oncology patients | |
|---|---|---|
| | number | % |
| positive sera | 23 | 37 |
| negative sera | 39 | 63 |
| total | 62 | 100 |

Example 17

Generation of Recombinant Baculovirus that Expressed His-LCMV-NP

The recombinant baculovirus that expressed His-LCMV-NP was generated by using Bac-to-Bac® Baculovirus Expression System (Invitrogen). In order to construct the recombinant donor vector, a cDNA from HeLa/MX cells was used. A complete NP gene with the initiation and stop codons was amplified by PCR using the primers NPMXF1S 5'-CC GAATTCATGTCTCTGTCCAAGGAAGTCA-3' (46-67) (SEQ ID NO:85) and NPMXF3A 5'-CCTCGAGTTAGAGTGTCACAACATTTGGTC-3' (1722-1700) (SEQ ID NO:86). The primers were designed with EcoRI and Xho I restriction sites (underlined), respectively. Numbers in parentheses show positions with respect to published NP sequence of MX strain (GenBank accession number Y16308, Reiserova et al. 2001).

The PCR reaction was performed with Phusion High Fidelity PCR Master MIX (Thermo Scientific) using gene-specific primers. The PCR protocol consisted of 98° C. for 2 min followed by 35 cycles of: denaturation at 98° C. for 30 sec, annealing at 58° C. for 40 sec, and extension at 72° C. for 2 min, followed by final extension at 72° C. for 7 min. The amplification product was digested with EcoRI and XhoI and cloned into pFastBAc HT A vector. The inserted LCMV-NP DNA was sequenced and confirmed to be in proper orientation downstream the promoter and identical to the original sequence. Verified recombinant donor plasmid (pFastBAc HT-LCMV-NP) was transformed to E. coli DH10Bac competent cells. Successful transposition to the recombinant bacmid DNA was verified by PCR using a combination of the pUC/M13 and gene-specific primers. Recombinant bacmid DNA containing the gene of the interest was used for transfection of SF9 insect cells. Finally, recombinant baculovirus clones overexpressing His-LCMV-NP were obtained after three successive plaque purifications.

Example 18

Expression and Purification of His-LCMV-NP

Figure 17:
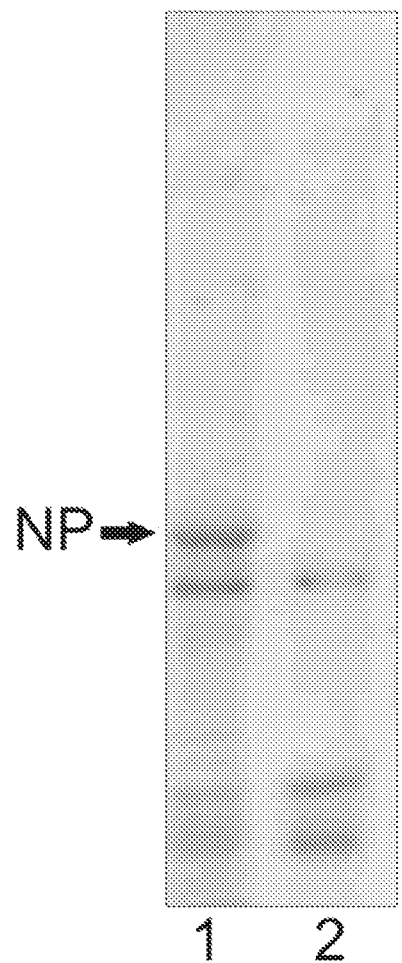
FIG. 17 is an image of a gel showing SDS-PAGE analysis of purified recombinant proteins. Lane 1, purified LCMV-NP antigen; lane 2, purified negative control antigen. A protein band of LCMV-NP antigen, approximately 62 kDa (lane 1) was detected.

SF9 cells infected with the recombinant baculovirus expressing His-LCMV-NP were incubated at 26° C. for 96 h. The cells were then harvested and washed three time with PBS. The cells were resuspended in 1% NP40 in PBS, allowed to stand on ice for 15 min, and centrifuged at 10,000 rpm for 10 min. The pellet was serially treated with urea solutions at different concentrations. First, the pellet was suspended in 1 M urea in 1% NP40 in PBS, sonicated, and centrifuged at 8,000 rpm for 5 min. Then, the pellet was washed in PBS and suspended in 2 M urea in PBS. After the suspension was sonicated and centrifuged, the pellet was washed in PBS and suspended in 8 M urea in PBS. The suspension was sonicated and centrifuged, and the supernatant was used as LCMV-NP antigen. The control antigen was produced from SF9 cells infected with baculovirus that do not contain LCMV-NP gene. The protein concentration of antigens was determined by using a Bradford protein assay (Bio-Rad Laboratories). The expression and purification efficiency of His-LCMV-NP was analyzed on 10% SDS-PAGE gel after staining with Coomassie blue (see FIG. 17).

Example 19

Cloning and Expression of Recombinant LCMV-GP1

A sequence corresponding to the GP1 sequence (amino acids 1 to 265) according to published GPC sequence of MX strain (GenBank accession number EU195888, Tomaskova et al. 2008) was amplified by PCR using the primers GPS-BamHI 5'-TTGGATCCTGTCAAACTTTGTCCCACACAAAG-3' (54-77) (SEQ ID NO:87) and GP1AEcoRI 5'-AGAATTCTCATCATCTAGTGAGGAACTTTGTCTTT TC-3' (863-840) (SEQ ID NO:88). In this way, BamHI and EcoRI restriction sites (underlined) were introduced. PCR reactions were performed using the primers listed above and GoTaq® Flexi DNA Polymerase (Promega, Madison, Wis., USA). Following an initial denaturation at 95° C. for 2 min, the amplification program was set as follows: denaturation at 95° C. for 30 s, annealing at 60° C. for 30 s, and extension at 72° C. during 45 s for a total of 35 cycles, and finally 7 min at 72° C. The PCR product was purified on a 1% agarose gel using NucleoSpin Extract II kit (Macherey-Nagel) and cloned in-frame with glutathione S-transferase into pGEX-4T-1 using BamHI and EcoRI restriction enzymes. To produce GST-fusion protein, verified plasmid construct (designated pGEX-4T1-GP1) was transformed into E. coli DH5α competent cells and induced with 0.75 mM IPTG (Sigma-Aldrich, USA, USA) for 3 hours in 37° C. Induced cultures of E. coli were pelleted by centrifugation, resuspended in ice-cold lysis buffer STE (10 mM NaCl, 10 mM Tris-HCl, 1 mM EDTA in 1×PBS), pH 8 and incubated on ice for 15 minutes with lysosyme (Serva, Germany) in the final concentration of 0.4 mg/ml. Before sonication of bacterial cells (5×15 s) 10% Sarcosyl (Sigma-Aldrich, USA) in STE to final concentration of 1.7% and 1 M DTT (Sigma-Aldrich, USA) to final concentration of 0.5 mM was added to cell suspension. After sonication 10% Triton X-100 (AppliChem) in STE was added to final concentration 2.5% and incubated on ice for 15 minutes. Then the insoluble material was removed by centrifugation for 15 minutes at 10 000 rpm at 4° C. The yield of fusion protein in induced samples was determined by SDS-PAGE and visual comparison to defined concentration of BSA.

Example 20

GP1-IgG ELISA 96-well polystyrene plates were coated overnight at 37° C. with lysate containing approximately 4 μg of recombinant GST-GP1 and/or GST/ml. Thereafter, plates were blocked for 1.5 h with 10% milk (200 ul per well) in PBS with 0.1% Tween 20 (PBS-T). On a parallel plate serum samples were prediluted 1:20 in blocking solution and a twofold dilution series was performed. A total of 50 μl per well of diluted serum samples was transferred to GP1- and GST-saturated, plates, followed by incubation for 1 hour. Finally, plates were incubated for 45 min with HRP conjugated goat anti-human IgG (Fc-specific) Ab (SIGMA) diluted 1:35000 in blocking solution. HRP was detected by OPD color reaction, which was stopped by adding 50 μl of 2M H2SO4. Optical density was measured for absorbance at 492 nm. All steps were carried out at room temperature. Between each step the plates were washed four times with PBS-T. The adjusted OD was calculated by subtracting the OD of the negative antigen-coated wells from that of corresponding wells.

Example 21

Assays for LCMV Detection

Figures 18A, 18B:
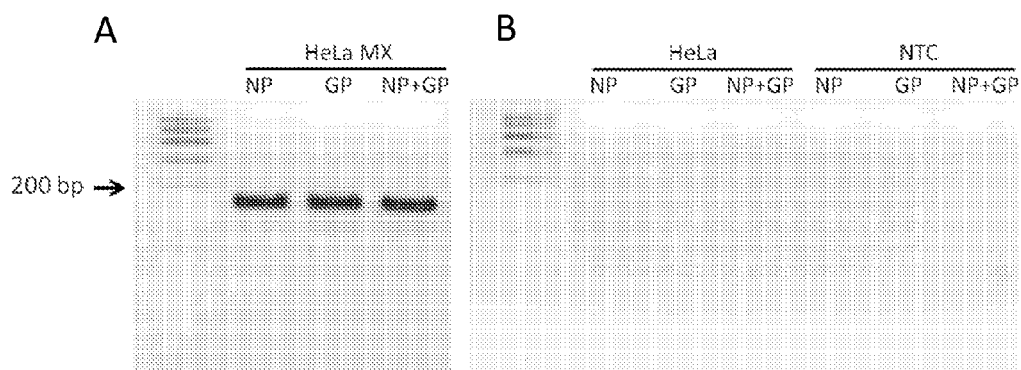
FIGS. 18A-18B are images of agarose gels showing electrophoresis of LCMV PCR products.

The following assays were performed to demonstrate detection of LCMV.
LCMV Detection Using MX Strain
For LCMV detection real-time PCR was used with dual labeled oligonucleotide probe (TaqMan) based on fluorescent detection system. Two specific regions of the LCMV genome were amplified: a fragment of the nucleoprotein encoding gene (NP) and a fragment of the glycoprotein encoding gene (GP). Amplifications were carried out both in singleplex formats (NP or GP) and in a duplex format (NP+GP). cDNA reverse transcribed from RNA of uninfected HeLa cells and molecular grade water were included as negative controls. For each target, the presence of only one PCR product on 1% agarose gels was confirmed (see FIG. 18).

Figures 19A, 19B:
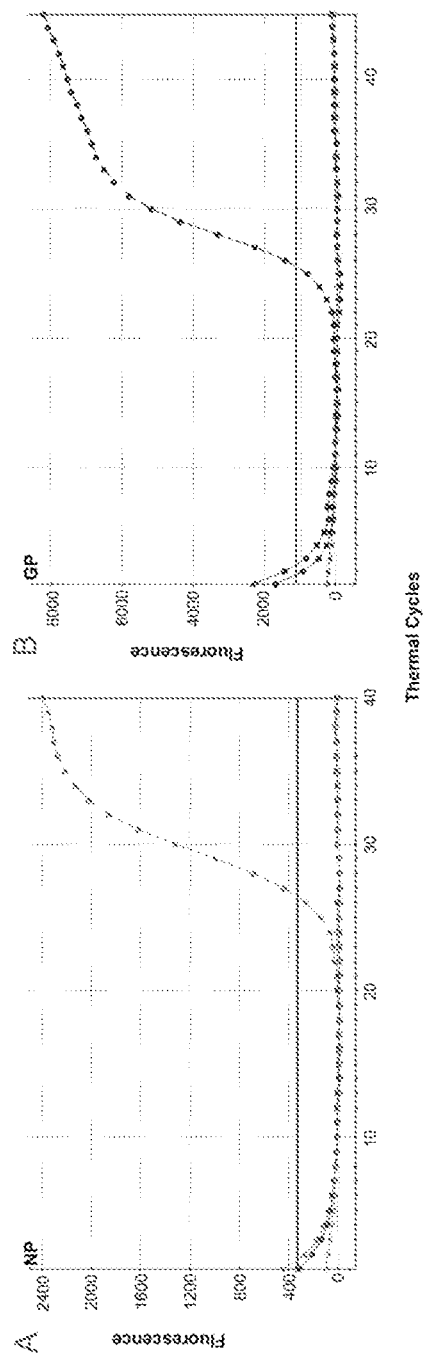
FIGS. 19A-19B are line graphs showing real-time detection of LCMV MX NP and GP genes in singleplex format.
Figure 20:
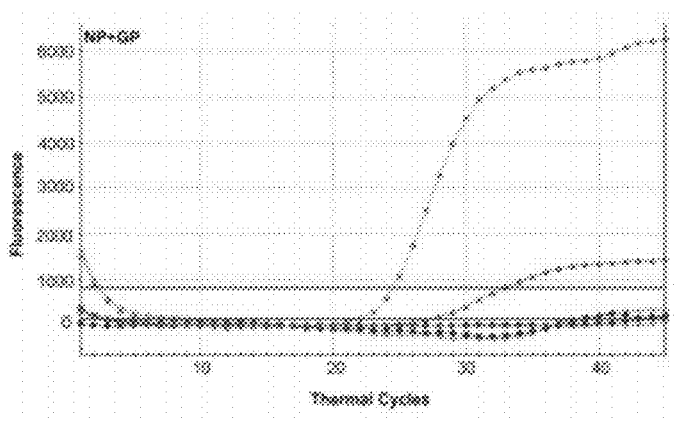
FIG. 20 is a line graph showing real-time detection of LCMV MX NP and GP genes in duplex format.

As shown in FIGS. 19A-19B, LCMV was detected via singleplex format. As demonstrated in FIG. 20, LCMV was also detected via the duplex format. Each reaction contained two sets of PCR primers for unique NP and GP nucleotide sequences and two TaqMan probes, each specific for one of the two amplification products and labeled with a differently colored fluorophore. Fluorescent signals from the HEX-labeled TaqMan (NP specific), and from the FAM-labeled TaqMan, are plotted in green, and grey, respectively.

LCMV Detection Using ARM Strain

Figures 21A, 21B:
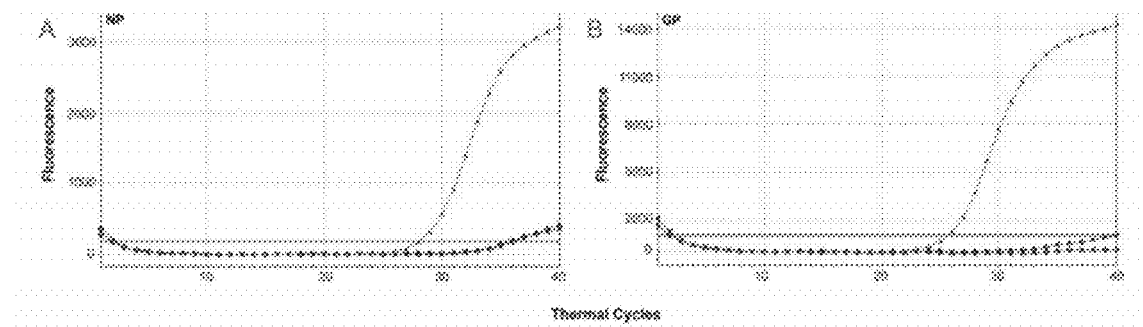
FIGS. 21A-21B are line graphs showing real-time detection of LCMV ARM NP and GP genes in singleplex format.
Figure 22:
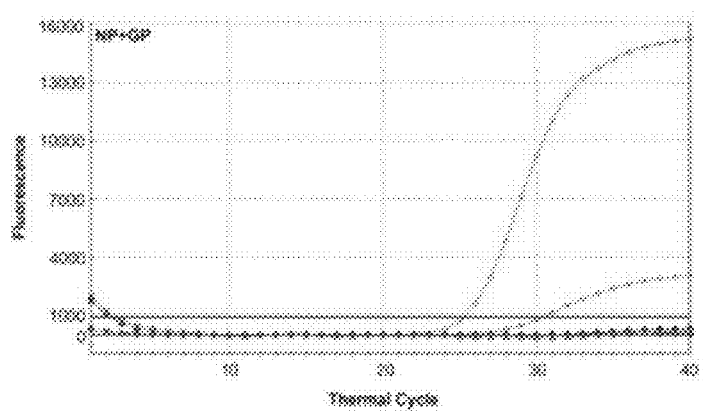
FIG. 22 is a line graph showing real-time detection of LCMV ARM NP and GP genes in duplex format.
Figures 23A, 23B, 23C, 23D:
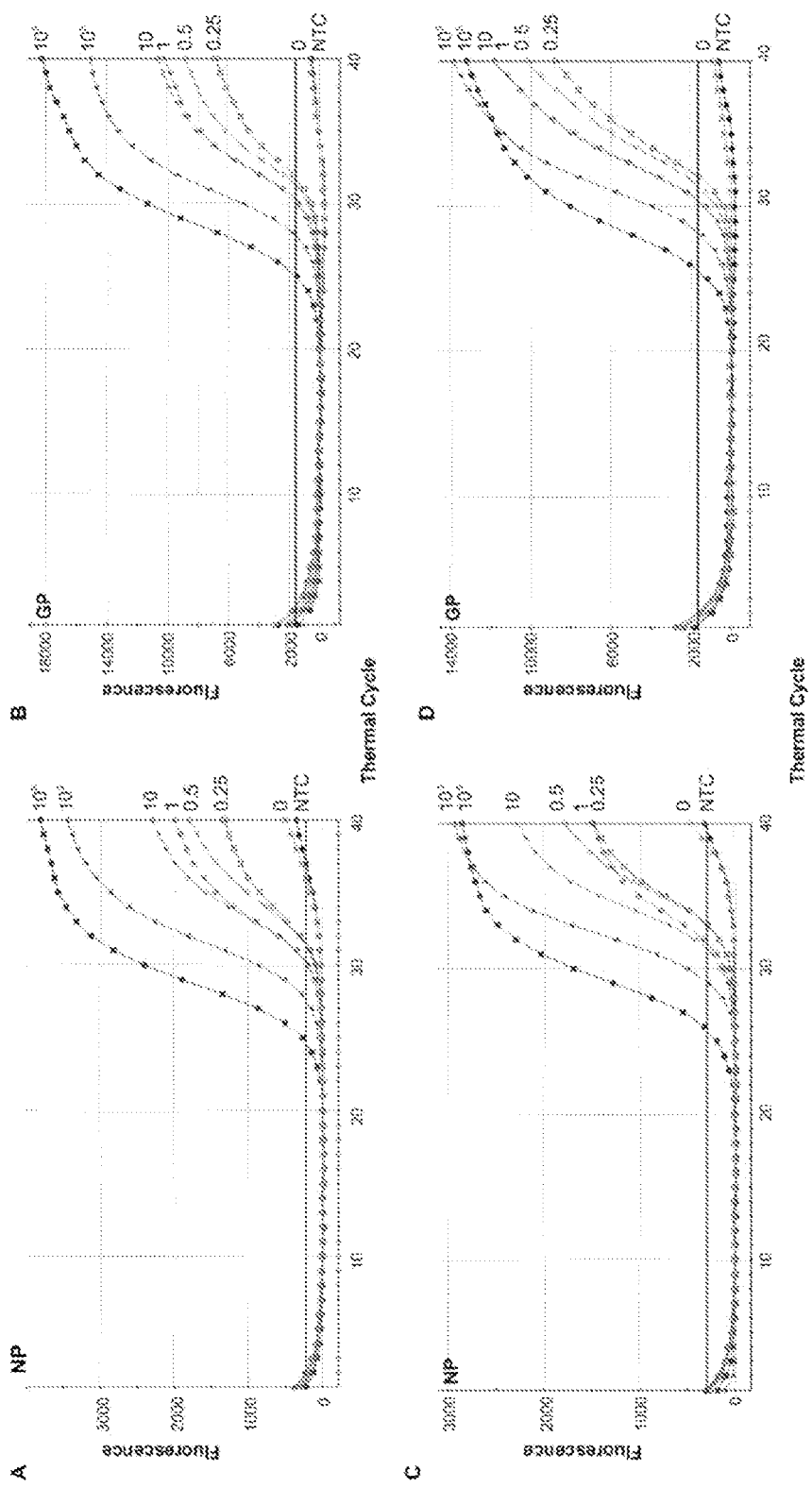
FIGS. 23A-23D are line graphs showing sensitivity of the LCMV real-time PCR assay. Blood samples spiked with serial dilutions of LCMV infected cells were tested by real-time PCR assay in singleplex (A, B), and duplex format (C, D).

The feasibility of the assay for detection of different LCMV strains was tested using the LCMV ARM strain. As shown in FIGS. 21 and 22, amplification products were successfully detected with both TaqMan probes in both singleplex (NP or GP) and duplex formats (NP+GP). The robustness of the assay was confirmed as the same TaqMan probes were suitable for amplicon detection even in the presence of mismatched oligonucleotides under the regions covered by the used probes. The primer and probe sequences were designed to perfectly match the sequence of the MX strain. Sequence differences between the MX and ARM strains resulted in 4 mismatched oligonucleotides in the NP probe/target region and in 2 mismatched nucleotides in the GP probe/target region. Despite this fact efficient amplification signal was generated by both TaqMan probe. cDNA reverse transcribed from RNA of uninfected HeLa cells and molecular grade water were included as negative controls.

Example 22

Sensitivity of Assays for LCMV Detection

The analytical sensitivity of qPCR was assessed by testing of serial dilution of the standard virus strain MX. Blood from healthy individual was spiked with serial dilution of LCMV infected cells (105, 103, 10, 1, 0.5, 0.25 infected cell) to standardize RNA extraction and to detect the analytical sensitivity of the PCR. Serial dilutions were prepared in a Dulbecco modified Eagle growth medium. Healthy blood samples were spiked with each of these dilutions. Blood from healthy individuals and molecular grade water were included as negative controls.

Dilution assays showed a reproducible detection limit of 0.25 LCMV infected cell (see FIG. 23A-23D).

Example 23

Hypoxia-Induced Upregulation of Expression LCMV MX NP and GP Genes

Using real-time PCR hypoxia-induced changes in the expression of LCMV NP and GP genes were measured. Total RNAs were prepared from cells incubated in normoxic or hypoxic conditions (2% O2) for 24 h for reverse transcription. Expression of LCMV genes was determined by quantitative real-time PCR. Differences in gene expression, expressed as fold-change, were calculated using the 2Ct method using ACTB (β-actin) as internal control. For each gene, the fold induction was determined in comparison with the normoxic control.

Figure 24:
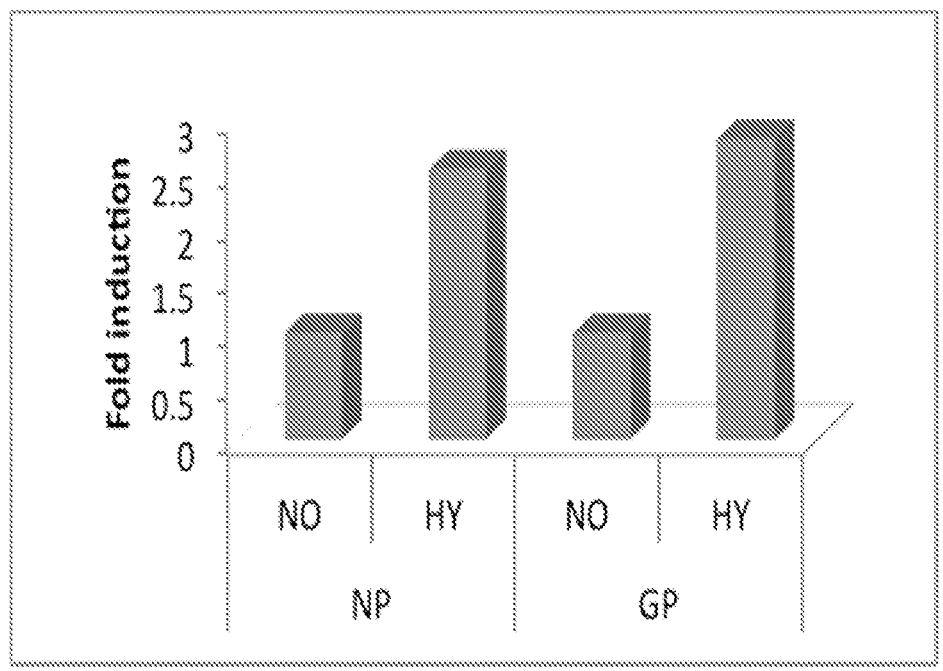
FIG. 24 is a bar graph showing LCMV MX NP and GP gene expression under hypoxic and normoxic conditions as assessed by real-time PCR.

As shown in FIG. 24, hypoxia significantly increased an expression of NP and GP genes in hypoxic HeLa-MX cells compared to the normoxic controls of the same strain (see FIGS. 21-22).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of assessing lymphocytic choriomeningitis virus (LCMV) infection status or activity in a subject, the method comprising:
   selecting a subject for assessment, wherein the subject has been exposed to LCMV and/or is at risk of increased LCMV activity;
   obtaining a sample from the subject;
   contacting the sample with a composition for detecting LCMV, wherein the composition comprises at least one isolated monoclonal antibody or antibody fragment thereof, comprising a heavy chain variable region ($V_H$) of monoclonal antibody M87 comprising the amino acid sequence of SEQ ID NO: 74, wherein the $V_H$ region comprises a $V_H$ CDR1 comprising SEQ ID NO: 76; a $V_H$ CDR2 comprising SEQ ID NO: 77; and a $V_H$ CDR3 comprising SEQ ID NO: 78, and wherein the antibody or fragment binds specifically to LCMV NP; and
   determining whether the composition for detecting LCMV is associated with a marker of LCMV from the sample, wherein detection of an association indicates that the subject is infected with and/or has active LCMV.

2. The method of claim 1, wherein determining comprises reporting that a subject is infected with and/or has active LCMV to the subject and/or a medical practitioner associated with the subject.

3. The method of claim 1, wherein determining further comprises detecting the level and/or activity of LCMV in a subject that is infected with and/or has active LCMV.

4. The method of claim 3, further comprising reporting the level and/or activity of LCMV detected to the subject and/or a medical practitioner associated with the subject.

5. The method of claim 1, wherein a subject at risk of increased LCMV activity is at risk of a condition associated with hypoxia.

6. The method of claim 5, wherein the subject is pregnant, immunocompromised, a transplant recipient, at risk for developing cancer, or has cancer.

7. A method of assessing lymphocytic choriomeningitis virus (LCMV) infection status or activity in a subject, the method comprising:
   selecting a subject for assessment, wherein the subject has been exposed to LCMV and/or is at risk of increased LCMV activity;
   obtaining a sample from the subject;
   contacting the sample with a composition for detecting LCMV, wherein the composition comprises an antibody or antibody fragment thereof produced by hybridoma MJ3, LMBP accession number 9217CB, deposited with the Belgian Coordinated Collections of Microorganisms (BCCM) at Ghent University, Belgium, and wherein the antibody or fragment binds specifically to LCMV ZP; and
   determining whether the at least one composition for detecting LCMV is associated with a marker of LCMV from the sample, wherein detection of an association indicates that that the subject is infected with and/or has active LCMV.

8. A method of assessing lymphocytic choriomeningitis virus (LCMV) infection status or activity in a subject, the method comprising:
   selecting a subject for assessment, wherein the subject has been exposed to LCMV and/or is at risk of increased LCMV activity;
   obtaining a sample from the subject;
   contacting the sample with a composition for detecting LCMV, wherein the composition comprises an antibody or antibody fragment thereof produced by hybridoma M166, LMBP accession number 9216CB, deposited with the Belgian Coordinated Collections of Microorganisms (BCCM) at Ghent University, Belgium, and wherein the antibody or fragment binds specifically to LCMV NP; and determining whether the at least one composition for detecting LCMV is associated with a marker of LCMV from the sample, wherein detection of an association indicates that that the subject is infected with and/or has active LCMV.

* * * * *

UNITED STATES PATENT AND TRADEMARK OFFICE
CERTIFICATE OF CORRECTION

PATENT NO. : 8,883,429 B2  
APPLICATION NO. : 13/345334  
DATED : November 11, 2014  
INVENTOR(S) : Jana Tomaskova et al.

Page 1 of 1

It is certified that error appears in the above-identified patent and that said Letters Patent is hereby corrected as shown below:

On the title page, item (56), column 2 (Other Publications), line 14, delete "transplantio-" and insert -- transplantation --, On the title page, item (57), column 2 (Abstract), line 9, delete "that that" and insert -- that --, In the Claims In Column 162, line 56, Claim 7, delete "that that" and insert -- that --, In Column 163, line 9, Claim 8, delete "that that" and insert -- that --.

Signed and Sealed this  
Seventeenth Day of March, 2015

Michelle K. Lee  
*Director of the United States Patent and Trademark Office*

SEQUENCE LISTING

```
<160> NUMBER OF SEQ ID NOS: 90

<210> SEQ ID NO 1
<211> LENGTH: 1717
<212> TYPE: DNA
<213> ORGANISM: Lymphocytic choriomeningitis virus

<400> SEQUENCE: 1
aaagtgtcac aacatttggt cctctaaaga ttagatcatg tggcaagatg ttgtgaatgg      60
tctttagatc agggagtctt gctttggagg cactctcaaa aatgatgcag tccataagtg     120
cacagtgcgg ggtgatctcc tttttctttt tgtcctttac tattccagtg tgcatcttac     180
acaaccaacc atacttgtcc catactttgt cttcatattc tcttgaggct tccttagtca     240
tttcaacatc aatgagtttt atatctctcc tattctgtga atctaggagc tttctgatgt     300
catcggagcc ttgacaactc aaaaccatcc cctgtgggag agcacctata actgaagagg     360
tcagtccagg ttgtgcgttg aaaaggtcag taaggtccat tccatgtgag tatttagagt     420
cctgcttaaa ctgcttttga tcagtgggct ctctgtaaaa atgtatgaac tgcccatttt     480
gtggttggaa aattgctatt tccaccggat cattgaatct gccctctata tcaatccatg     540 tggggggcgtt agggtcgatc cctcccataa ggtctttcag gagcattgtc tggctgtagc     600
```

-continued

```
tcagacccac ttgaggtgga cctgctgacc caggcactgg cctgggtgag ctggttgcga    660
gcctctcatt cgaaaggtca attgttgtat tttcccatgc tctccctaca attgatgttc    720
tacatgctat gtatggccat ccttcacctg aaagacagac tttgtagagg atgttttcat    780
atgggtttct atcccaacc tgatcagaga caaacatgtt gagtttcttt ttgaccccaa     840
ggactgcttt caataggtct tcactgttgc ttggcttgat taggatagac tctagcatgt    900
ttcccccgtc tagcaaagct gctcctgctt cacagcagc accaagactg aaattgtaac     960
cagaaatgtt tatgctagac tgctgctcag tgatgacccc taaaactggg tgcttgtctt   1020
ttagcttttc aaggtcactg agatttgggt actttactgt gtaaagtaag ccaagatctg   1080
tgagtgcttg cacaacgtca ttgagtgggg tctgtgactg tttggccatg caagccattg   1140
tcaggcttgg catggtgcca aattgattgt ttaaaagtga tgaatctttc acatcccaca   1200
ctctcaccac accagtagca ccttgttgag gcctcctcat cccaaccatg tgcaggatct   1260
gtgatctttg gtcaagctgc tgtgcagtca agtttcccat atagactcca gaagcttgag   1320
gcctttcaga cctataatt ttagccttta atttttcaag gtcggctgca agagacatta    1380
gttcttctgc actgagcctt cccactttga gaacattctt cttcgatgtt gactttagat   1440
ccacaagaga atacacagtt tgattaagac ttctgagtct ctgcaggtct tgtcatccc    1500
tcttctcttt cctcataatc ctctgaacat tactaacttc agagaagtcc agcccattca   1560
acagactagt tgcatctttg atgacagctg ccttcacgtc tgatgtgaag ctctgcagct   1620
ccctcctcag ggcttgtgtc cactggaagc tcttaacctc cttggacaga gacatcctgt   1680
tgctcaatga atttccaaga caaatgcgca atcaaat                            1717
```

<210> SEQ ID NO 2
<211> LENGTH: 1717
<212> TYPE: DNA
<213> ORGANISM: Lymphocytic choriomeningitis virus

<400> SEQUENCE: 2

```
aaagtgtcac aacatttggt cctctaaaga ttagatcatg tggcaagatg ttgtgaatgg     60
tctttagatc agggagtctt gctttggagg cactctcaaa aatgatgcag tccataagtg    120
cacagtgcgg ggtgatctcc ttttctttt tgtcctttac tattccagtg tgcatcttac    180
acaaccaacc atacttgtcc catactttgt cttcatattc tcttgaggct tccttagtca    240
tttcaacatc aatgagtttt atatctctcc tattctgtga atctaggagc tttctgatgt    300
catcggagcc ttgacaactc aaaaccatcc cctgtgggag agcacctata actgaagagg    360
tcagtccagg ttgtgcgttg aaaaggtcag taaggtccat tcatgtgag tatttagagt     420
cctgcttaaa ctgcttttga tcagtgggct ctctgtaaaa atgtatgaac tgcccatttt    480
gtggttggaa aattgctatt tccaccggat cattgaatct gccctctata tcaatccatg    540
tgggggcgtt agggtcgatc cctcccataa ggtctttcag gagcattgtc tggctgtagc    600
tcagacccac ttgaggtgga cctgctgacc caggcactgg cctgggtgag ctggttgcga    660
gcctctcatt cgaaaggtca attgttgtat tttcccatgc tctccccaca attgatgttc    720
tacatgctat gtatggccat ccttcacctg aaagacagac tttgtagagg atgttttcat    780
atgggtttct atcccaacc tgatcagaga caaacatgtt gagtttcttt ttgaccccaa     840
ggactgcttt caataggtct tcactgttgc ttggcttgat taggatagac tctagcatgt    900
ttcccccgtc tagcaaagct gctcctgctt cacagcagc accaagactg aaattgtaac     960
```

| | |
|---|---|
| cagaaatgtt tatgctagac tgctgctcag tgatgacccc taaaactggg tgcttgtctt | 1020 |
| ttagcttttc aaggtcactg agatttgggt actttactgt gtaaagtaag ccaagatctg | 1080 |
| tgagtgcttg cacaacgtca ttgagtgggg tctgtgactg tttggccatg caagccattg | 1140 |
| tcaggcttgg catagtgcca aattgattgt ttaaaagtga tgaatctttc acatcccaca | 1200 |
| ctctcaccac accagtagca ccttgttgag gcctcctcat cccaaccatg tgcaggatct | 1260 |
| gtgatctttg gtcaagctgc tgtgcagtca agtttcccat atagactcca gaagcttgag | 1320 |
| gcctttcaga ccttataatt ttagtctttta attttttcaag gtcggctgca agagacatta | 1380 |
| gttcttctgc actgagcctt cccactttga gaacattctt cgtcgatgtt gactttagat | 1440 |
| ccacaagaga atacacagtt tgattaagac ttctgagtct ctgcaggtct ttgtcatccc | 1500 |
| tcttctcttt cctcataatc ctctgaacat tactaacttc agagaaatcc agcccattca | 1560 |
| acagactagt tgcatctttg atgacagctg ccttcacgtc tgatgtgaag ctctgcagct | 1620 |
| ccctcctcag ggcttgtgtc cactggaagc tcttaacctc cttggacaga gacatcctgt | 1680 |
| tgctcaatga atttctaaga caaatgcgca atcaaat | 1717 |

<210> SEQ ID NO 3
<211> LENGTH: 1722
<212> TYPE: DNA
<213> ORGANISM: Lymphocytic choriomeningitis virus

<400> SEQUENCE: 3

| | |
|---|---|
| ttagagtgtc acaacatttg gtcctctgaa gatcaagtca tgtggcagga tgttgtggac | 60 |
| agtctttaag tcagggagcc tcgccttgga agcactctca aatatgatgc agtccatgag | 120 |
| tgcacagtgt ggggtgattt ctttattctt cttatccctc actatcccag tgtgcatctt | 180 |
| gcataaccag ccatatttgt cccacacttt gtcttcatac tctcttgaag cctctttggt | 240 |
| catctcaaca tcaataagct ttatgtccct tctattctgt aaatctagga gctttctgat | 300 |
| gtcatcagag ccttgacagc ttaagaccat tccttgtgga agagcaccta tgactgatga | 360 |
| ggtcagtcca ggttgtgcat tgaagagatc agtaagatcc atgccgtgtg agtacttgga | 420 |
| gtcctgtttg aactgtttct gatcggtagg ttctctgtaa aaatgtataa attgcccatt | 480 |
| ttgtggttgg aatattgcta tttccactgg atcattgaac ctaccctcaa tgtcaatcca | 540 |
| tgtgggagca ttaggatcga tccctcccat gaggtccttc agcagcattg cttggccata | 600 |
| gctcaagcct acctgaggcg gacctgctgc tccaggcact ggcctgggtg agttggttac | 660 |
| agacttctca cttgtgagat cgattgttgt gttttcccat gctctcccca caatcgatgt | 720 |
| cctacaagct atgtatggcc acccttcacc tgagagacag actttgtaga ggatgttttc | 780 |
| gtaagggttt ctatctccaa cttgatcaga gacaaacatg ttaagtttcc tttttgcccc | 840 |
| aagaaccgct ttcagaaggt cttcactatt gctcggctta atcaagatgg attccagcat | 900 |
| gttgccccca tccaacaagg ctgctcctgc tttcacagct gctccaagac tgaaattata | 960 |
| gccagagatg tttatactgg attgctgttc ggtgatgacc cccagaactg ggtgcttgtc | 1020 |
| ttttagcttt tcaaggtcat tgagatttgg gtatttaact gtgtaaagca gaccaaggtc | 1080 |
| tgtgagtgct tgcacaacat cattcagtgg agtctgtgat tgtttggcca tgcaagccat | 1140 |
| tgtcagactt ggcattgtgc caaattgatt gttcagtagt gatgaatcct tcacatccca | 1200 |
| gactctcacc acaccatttg caccttgctg aggcctcctc atcccaacca tttgcaaaat | 1260 |
| ttgagatctt tgatcaagct gttgtgttgt caagctcccc atatagactc cagaagtttg | 1320 |
| aggtctttca gacctcataa ttttgccctt taacttctca aggtcggcag cgagagacat | 1380 |

```
cagttgttcc gcactaagtc ttcccacttt tagaacattc ttttttgatg ccgacttcag   1440
gtctacaagg gaatacacag tctgattaag acttctgagc ctttgtaggt ctttgtcatc   1500
tctcttctcc ttcctcatga ttctctgaac attgctaact tcagagaagt ctaaaccatt   1560
tagaaggcta gttgcgtcct tgatgacagc agccttcaca tctgttgtga agttttgcag   1620
ttccctcctc agtgcctgtg tccactgaaa gctcttgact tccttggaca gagacatctt   1680
gttgctcaat gaattttcaa gtcaaatgcg tatcaacaaa ta                      1722
```

<210> SEQ ID NO 4
<211> LENGTH: 1755
<212> TYPE: DNA
<213> ORGANISM: Lymphocytic choriomeningitis virus

<400> SEQUENCE: 4

```
agggaggccc agcgggtctt agagtgtcac aacattgggt cctctgaaga tcaaatcatg     60
tggcaggatg ttgtgaacgg tctttagatc agggagtctt gccttggaag cactctcaaa    120
gatgatgcag tccatgagtg cacagtgtgg ggtgatttct ttcttctttt tgtctctcac    180
taccccagtg tgcattttgc atagccagcc atatttgtcc cacactttat cttcatattc    240
tcttgaggcc tccttagtca tctcaacatc aatgagtttt atgtcccttc tattctgtga    300
gtccagaagc tttctgatgt catcagaacc ttgacagctc aagaccatcc cttgtgggag    360
agcacctata actgatgagg tcagcccagc ctgtgcattg aagaggtcag caagatccat    420
gccgtgtgaa tacttggagt cctgcttgaa ttgcttctgg tccgtaggtt ctctgtaaaa    480
atgtatgaat tgcccatttt gtggttgaaa tattgctatc tccactggat cattgaacct    540
gccttcaatg tcaatccatg tgggagcatt gggatcaatc cctcccatca agtctttcaa    600
cagcattgtt tgactgtaac tcaagcccac ctgaggtggg cctgctgctc caggcactgg    660
cctagatgag ttggccacaa gtttttcatt tgtgagatca attgtcgtgt tctcccatgc    720
tctccccaca actgacgttc tacaggctat gtatggccat ccttcacctg aaagacagac    780
tttataaagg atgttttcat aaggatttct atccccaact tgatctgaga caaacatgtt    840
gagtttcttc ttggccccaa ggactgcttt taggagatcc tcactattgc ttggtttgat    900
caaaatagat tccagcatgt tccctccatg tagcagagct gcccccgctt tcacagccgc    960
accaagactg aaattataac cagagatatt gatactagat tgctgttcag taatgacccc   1020
cagaactggg tgtttatctt ttagcctttc taggtcactg agattcgggt atttgactgt   1080
gtaaagtaag ccaaggtctg tgagtgcctg cacaacatca ttgagtgggg tctgtgactg   1140
ttttgccatg caagccattg tcaggcttgg cattgtgccg aactgattgt tcagaagtga   1200
tgagtccttc acatcccaaa cccttactac accacttgca ccctgctgag gtcttctcat   1260
cccaaccatt tgcagtattt gggatctctg atcaagttgt tgtgctgtca aatttcccat   1320
gtagactcca gaagcttgag gcctctcagt tctcataatt ttggccttca gcttctcaag   1380
atcagctgca agggtcatca attcctctgc actaagtctt cccactttca gaacattttt   1440
ctttgatgta gacttcggat caacaagaga atgcacagtc tggttaagac tcctgagtct   1500
ctgcaagtct ttatcgtccc tcctttcctt tctcatgatc ctctgaacgt tgctgacttc   1560
agaaaagtcc aacccattta gaagactggt tgcgtccttg atgacggcag cctttacatc   1620
tgatgtaaaa ccctgcaact ccctcctcaa cgcctgtgtc cactgaaagc ttttgacttc   1680
tttggacaaa gacattttgt cacacaatga atttccaaat aaaagcgcaa tcaaatgcct   1740
```
aggatccact gtgcg                                                      1755

<210> SEQ ID NO 5
<211> LENGTH: 1756
<212> TYPE: DNA
<213> ORGANISM: Lymphocytic choriomeningitis virus

<400> SEQUENCE: 5
agggaggccc agagggtctt agagtgtcac aacatttggg cctctaaaaa ttaggtcatg      60
tggcagaatg ttgtgaacag ttttcagatc tgggagcctt gctttggagg cgctttcaaa    120
aatgatgcag tccatgagtg cacagtgcgg ggtgatctct tcttcttttt tgtcccttac    180
tattccagta tgcatcttac acaaccagcc atatttgtcc cacactttgt cttcatactc    240
cctcgaagct tccctggtca tttcaacatc gataagctta atgtccttcc tattctgtga    300
gtccagaagc tttctgatgt catcggagcc ttgacagctt agaaccatcc cctgcggaag    360
agcacctata actgacgagg tcaacccggg ttgcgcattg aagaggtcgg caagatccat    420
gccgtgtgag tacttggaat cttgcttgaa ttgttttga tcaacgggtt ccctgtaaaa    480
gtgtatgaac tgcccgttct gtggttggaa aattgctatt ccactggat cattaaatct     540
accctcaatg tcaatccatg taggagcgtt ggggtcaatt cctcccatga ggtcttttaa    600
aagcattgtc tggctgtagc ttaagcccac ctgaggtgga cctgctgctc caggcgctgg    660
cctgggtgaa ttgactgcag gtttctcgct tgtgagatca attgttgtgt tttcccatgc    720
tctccccaca atcgatgttc tacaagctat gtatggccat ccttcacctg aaaggcaaac    780
tttatagagg atgttttcat aagggttcct gtccccaact tggtctgaaa caaacatgtt    840
gagttttctc ttggccccga aactgccctt caagaggtcc tcgctgttgc ttggcttgat    900
caaaattgac tctaacatgt tacccccatc aacagggct gccctgcct tcacggcagc      960
accaagacta agttatagc cagaaatgtt gatgctggac tgctgttcag tgatgacccc    1020
cagaactggg tgcttgtctt tcagccttc aagatcatta agatttggat acttgactgt    1080
gtaaagcaag ccaaggtctg tgagcgcttg tacaacgtca ttgagcggag tctgtgactg    1140
tttggccata caagccatag ttagacttgg cattgtgcca aattgattgt tcaaaagtga    1200
tgagtctttc acatcccaaa ctcttaccac accacttgca ccctgctgag gctttctcat    1260
cccaactatc tgtaggatct gagatctttg gtctagttgc tgtgttgtta agttccccat    1320
atataccct gaagcctggg gcctttcaga cctcatgatc ttggccttca gcttctcaag    1380
gtcagccgca agagacatca gttcttctgc actgagcctc cccactttca aaacattctt    1440
ctttgatgtt gactttaaat ccacaagaga atgtacagtc tggttgagac ttctgagtct    1500
ctgtaggtct ttgtcatctc tcttttcctt cctcatgatc ctctgaacat tgctgacctc    1560
agagaagtcc aacccattca gaaggttggt tgcatcctta atgacagcag ccttcacatc    1620
tgatgtgaag ctctgcaatt ctcttctcaa tgcttgcgtc cattggaagc tcttaacttc    1680
cttagacaag gacatcttgt tgctcaatgg tttctcaaga caaatgcgca atcaaatgcc    1740
taggatccac tgtgcg                                                   1756

<210> SEQ ID NO 6
<211> LENGTH: 1756
<212> TYPE: DNA
<213> ORGANISM: Lymphocytic choriomeningitis virus

<400> SEQUENCE: 6
agggaggccc agagggtctt agagtgtcac aacatttgga cctctgaaga tcaggtcatg      60

```
tggcagtatg ttgtggatgg acttcaggtc gggaagcctt gccttggagg cactctcaaa    120
aatgatgcaa tccataagtg cgcagtgtgg ggtgatctct ttcttctttt tgtctctcac    180
tatcccggtg tgcatcttgc acagccagcc atacttgtcc cacaccttgt cctcgtactc    240
ccttgaggct tccttggtca tttccacatc tataagcttt atatcccttc tattctgtga    300
gtctagtagc tttctgatgt catcagaacc ctgacagctc aaaaccatcc cctgtggaag    360
ggcaccaagg acagatgagg tcaacccagg ttgtgcatta aagagatcag caagatccat    420
accatgtgag tacttagaat cttgcttgaa ctgtttctga tcagtaggtt ccctataaaa    480
atgtatgaat tgcccagtct gtggttggaa cagtgctatt tccactgggt cattggatct    540
gccttcaatg tcaatccatg taggggcatt agggtcgatc cctcccatga ggtctttcaa    600
cagcattgtc tgactgtagc tcaagcctac ttgaggtggt cctgctgctc caggtgatgg    660
tctgggtaag ttagccacag gtctctcatt tgtgaggtca attgttgtgt ctcccatgc    720 tctccccaca attgatgttc tacatgctat gtacggccat ccttcacctg ataagcaaac    780
cttatagaga atgttttcat aaggattccg atctccaact tggtctgaaa caaacatatt    840
gagctttctt tttgccccga gaactgcttt caagaggtcc tcactgttgc ctggtttgat    900
cagaatggac tccagcatat tgcccccgtc aagagagct gcccctgctt tcacagcagc    960
accgagactg aagttgtagc cagaaatgtt gattcctgat tgctgttcag tgataacccc   1020
taagactggg tgtttgtctt tcagtctctc cagatcacca aggtttgggt acttaactgt   1080
gtaaagtagg ccaaggtctg tgagtgcttg cacgacatca ttgagtgggg tctgtgactg   1140
tttagccatg caagccattg tcaggcttgg cattgtgcca aattgattgt tcagaagtga   1200
tgagtctctc acatcccaga ccctcaccac gccattcgtg ccttgctgag gtctcctcat   1260
cccaaccatc tgcaagatct gggatctttg atcaagttgt tgcaccgtca agttccccat   1320
gtagacccca gaagcctgag gtctctcagt tctcatgatt ttggccttca gtttctcgag   1380
atcagctgca agagacatca gttcctccgc actgagcctt cccaccttca ggacattttt   1440
cttcgaggtt gacttcaagt ccacaagaga atacacagtt tgattgaggc ttctgagcct   1500
ctgtaagtct ttatcatctc ttttttcctt cctcatgatt ctctgacat tgctgacttc   1560 agagaagtcc aatccgttca ggaggctagt tgcatccttg atgacagcag cctttacatc   1620
tgatgtaaag ttctgcaact cccttcttaa cgcctgtgtc cattgaaaac tcttgatttc   1680
tttggacaag gacatcttgt cgctcaatga ttcaccaaga caaatgcgca atcaaatgcc   1740
taggatcccc ggtgcg                                                   1756

<210> SEQ ID NO 7
<211> LENGTH: 1548
<212> TYPE: DNA
<213> ORGANISM: Lymphocytic choriomeningitis virus

<400> SEQUENCE: 7
gtagcgcctc cctgactcac cacctcgaaa gaggtggtga gtcagggagg cccagagggt     60
cttagagtgt tactacattt ggacctctga agatcaggtc atgtggtagg atgttgtgga    120
cagttttcaa gtcggggagc cctgccctgg aggcactctc aaagatgata caatccatga    180
gtgcacagtg tggggtgatc tcttttcttt tcttgtcctt cactattcca gtgtgcatct    240
tgcatagcca gccatatctg tcccaaactt tgtcctcata ttctctcgaa gcttctttag    300
tcatctcaac atcgataagc ttgatgtctc ttctgttttg tgaatctagg agtttcctga    360
```

-continued

| | |
|---|---|
| tgtcatctga accttgacag cttaagacca tcccttgtgg aagagcacct attacagaag | 420 |
| atgtcagccc aggttgtgca ttgaagaggt cagcaaggtc cattccatgt gagtatttgg | 480 |
| agtcctgctt gaattgtttt tgatcagtgg gttctctgta gaaatgtatg tactggccat | 540 |
| tctgtggctg aaatattgct atttctactg ggtcattgaa tctgccctca atgtcaatcc | 600 |
| atgtaggagc gttagggtca atacctccca tgaggtcctt caacaacatt gtttggctga | 660 |
| agcttaagcc cacctgaggt gggcccgctg ctccaggcac tggtttgggt gagttggcca | 720 |
| taggcctctc gtttgtcaga tcaattgttg tgttctccca tgctctccct acaactgatg | 780 |
| ttctgcaggc tatgtatggc caccctttccc ctgaaagaca gactttgtag aggatgttct | 840 |
| cgtagggatt cctgtctcca acctgatcgg aaacaaacat gttgagtttc ttcttggccc | 900 |
| caagaactgc tttcaagaga tcctcgctgt tgcttggctt aattaaaatg gattccagca | 960 |
| tgttgccccc atctaacaag gcrgccctg cttcacagc agcaccgaga ctgaaattgt | 1020 |
| agccagatat gttgatgctg gactgctgct cagtgataac tcccaagact gggtgcttgt | 1080 |
| ctttcagcct ttcaagatca ctcaggttcg ggtatttgac tgtgtaaagc agcccaaggt | 1140 |
| ctgtgagtgc ttgtacaacg tcattgagtg aggtctgtga ttgtttagcc atgcaagcca | 1200 |
| tggttaagct tggcattgtg ccaaattgat tgttcagaag tgatgaatcc ttcacatccc | 1260 |
| agaccctcac cacaccattt gcaccctgct gaggtctcct cattccaacc atttgcagar | 1320 |
| tctgagatct ttgakcaagc tgttgtgctg ttaagttccc catgtagact ccagaagtta | 1380 |
| gaggcctttc agacctcatg atttttggcct tcagttttc aaggtcagct gcaagggaca | 1440 |
| tcagttcttc tgcactaagc ctccctactt ttagaacatt cttttttgat gttgactta | 1500 |
| agtccacaag agaatacaca gtttggttga ggcttctgag tctctgca | 1548 |

<210> SEQ ID NO 8
<211> LENGTH: 1738
<212> TYPE: DNA
<213> ORGANISM: Lymphocytic choriomeningitis virus

<400> SEQUENCE: 8

| | |
|---|---|
| tcagagtgtc acgacatttg gacctctgaa gatcaggtca tgtggcaaga tgttgtggac | 60 |
| agttttcaag tcagggagcc ttgccttggt ggcgctctca agatgatgc agtccatgag | 120 |
| tgcacagtgt ggggtgatct cttctcttct cttgtccttc actattccag tgtgcatctt | 180 |
| gcatagccag ccatatttgt cccagacttt gtcctcatat tctcttgaag cttctttggt | 240 |
| catctcgaca tcaatgagtt tgatgtctct tctgttctgt gaatctagga gtttcctgat | 300 |
| gtcatcagaa ccctgacaac ttaagaccat tccctgtgga agagcaccta ccaccgagga | 360 |
| tgtcagccca ggttgtgcat tgaaaagatc aacaaggtcc ataccatgtg agtatttgga | 420 |
| atcctgcttg aactgttttt ggtcagtggg ttctctataa aatgtatgt actgcccatt | 480 |
| ttgtggttga atattgcta tttctactgg gtcattgaac ctgccctcaa tgtcaatcca | 540 |
| tgtgggagcg ttggggtcaa tgcctcccat aaggtctttc agcaacattg tttggctgta | 600 |
| gcttaaaccc acttgaggtg ggcctgctgc tccaggcgct ggtctgggtg agttagccat | 660 |
| aggcctctca tttgtcagat caattgttgt gttctcccac gctctcccta caactgatgt | 720 |
| tctacaagct atgtatggcc acccctcacc tgaaagacag actttataga ggatgttctc | 780 |
| gtaaggattc ctgtcccaa cttgatcaga aacaaacatg ttgagtttcc ttttggcccc | 840 |
| aagaactgct tcaggaggt cctcactatt gcttggctta attaagatgg attccaacat | 900 |
| gttgccccca tccaacaaag ctgcccctgc ttttacagca gcaccgagac tgaaattata | 960 |

-continued

```
gccagatatg ttgatgctag actgttgctc agtgatgact cccaagactg ggtgcttgtc    1020
tttagccctc tcaaggtcac tcaggttcgg gtatttgact gtgtaaagca acccaaggtc    1080
tgtgagtgcc tgcacaacgt cattaagtga ggtctgtgac tgtttggcca tacaggccat    1140
tgttaggctt ggcattgtgc caaattgatt attcagaagt gatgagtcct tcacatccca    1200
gaccctcacc acaccatttg caccctgctg aggtctcctc atcccaacca tctgcagaat    1260
ttgagatctt tgatcaagct gttgtgctgt taaattcccc atgtagactc cagaagcttg    1320
aggcctttca gacctcatga ttttagcctt cagttttca agatcagctg caagagacat    1380
cagttcttct gcactgagtc tccccacttt tagaacattc ttttttgatg ctgactttag    1440
gtccacaagg gaatacacag tttggttgag gcttctgagc ctctgtaagt ctttatcatc    1500 cctctttcc ttcctcatga ttctctgaac gttgctcact tcagagaaat ccaatccatt    1560
cagaaggctg gtggcatcct tgatcacagc agccttcaca tctgatgtga agctctgaag    1620
ctctcttctc aatgcttggg tccactgaaa acttttgact tctttggaca gagacatttt    1680
gtcactcaat gaatctccaa gacaaatgcg caatcaaatg cctaggatcc ccggtgcg     1738
```

```
<210> SEQ ID NO 9
<211> LENGTH: 1761
<212> TYPE: DNA
<213> ORGANISM: Lymphocytic choriomeningitis virus

<400> SEQUENCE: 9
```

```
gtcagggagg ccctttgagg gttcagaggg tcacaacatt tggacctctg aagaccaggt      60 catgggcag tatattgtgt acagtcttca ggtctggcag cctagccttt gaagcactct     120
caaaaatgat gcagtccatg agagcacagt gtggggtgat ttctttcttc tttttgtcct     180
taacaatccc agtgtgcatt ttgcatagcc agccgtactt gtcccaaact ttatcctcat     240
attctcgtga agcttccttg ttcatctcga catcaatgag cttgatatcc cttctattct     300
gtgagtctaa gagtttcctg atatcatcag acccttgaca gctgagcacc attccctggg     360
gaagggcgcc aattactgag gaagttaatc ccggttgtgc attgaagaga tcggccagat     420
ccatcccatg tgagtacttt gaatcttgtt taaattgttt ttgatcagta ggttccctgt     480
aaaaatgtat gaactgccca ttctgtggct gaaagatagc aacttccacc ggatcattgt     540
atctaccctc aatgtctatc catgtgggtg catttggatc aatcccgctc attagatctt     600
ttaacagcat ggtttgactg tagcttaatc ccacttgggg tggccctgct gctcctggtg     660
aaggtcttgg taagtcggtc ataggcttgt caccagatag atcaattgtt gtgttttccc     720
atgcccttcc cacaacagat gtcctacagg caatgtaggg ccaaccttcc cctgacaggc     780
agatcttgta caagatgttc tcataagggt ttctgtctcc cacttggtct gagacaaaca     840
tattaaactt gcgttttgcc ccgagaactg cttttaggag ttcctcagaa ttgctgggct     900
taattaggat tgattccaac atattgcccc catccagcaa tgcggctcct gctttgacag     960
ctgcacccaa actgaagttg tacccagata tattgatgct ggattgctgc tcggttatca    1020
cacccagaac tgggtgtttg tctttcagcc tgtcaagatc cgacaaattg gggtatttga    1080
ctgtgtagag caggcccagg tctgtgagtg cttgcacaac atcgtttaaa ggggtctgtg    1140 cctgttttggc aatacaagcc attgtcaagc tgggcattgt gccaaattga ttgttcaaaa    1200
gtgatgagtc cttcacatcc caaactctga caacccatt gtttccctgc tggggcctcc    1260
tcatcccaac catttgtaga atttgagatc tttggtcgag ctgctgtgtt gtcagattgc    1320
```

| | |
|---|---|
| ccatatagac ccctgatgct tgtggtctct ctgatctcat tatcttggct ttcagctttt | 1380 |
| ctagatcagc tgctaaagac attaactcct ctgcattgag tctgcccact tttagaatgt | 1440 |
| tcttcttaga cgtggatttt aactccacaa gggagtgtac tgtctggttc aggctcctca | 1500 |
| gtctctgcag atctttgtca tctctcctat cctttctcat aattctctga acgttgctaa | 1560 |
| cttcagagaa gtcaagtcca ttgagaagac tagtggcatc cttgatgaca gcagccttaa | 1620 |
| catttgaggt gaaaccctgt agctctctcc tcagtgcctg tgtccactgg aaactcttga | 1680 |
| tctccttgga cagagacatt gtggtgatgc tcactgtgtc tccaacaaaa gcgcaatcaa | 1740 |
| atgcctagga tccactgtgc g | 1761 |

<210> SEQ ID NO 10
<211> LENGTH: 1761
<212> TYPE: DNA
<213> ORGANISM: Lymphocytic choriomeningitis virus

<400> SEQUENCE: 10

| | |
|---|---|
| gtcagggagg ccctttgagg gttcagaggg tcacaacatt tggacctctg aagaccaggt | 60 |
| catggggcag tatattgtgt acagtcttca ggtctggcag cctagccttt gaagcactct | 120 |
| caaaaatgat gcagtccatg agagcacagt gtggggtgat ttctttcttc tttttgtcct | 180 |
| taacaatccc agtgtgcatt ttgcatagcc agccgtactt gtcccaaact ttatcctcat | 240 |
| attctcgtga agcttccttg ttcatctcga catcaatgag cttgatatcc cttctattct | 300 |
| gtgagtctaa gagtttcctg atatcatcag acccttgaca gctgagcacc attccctggg | 360 |
| gaagggcgcc aattactgag gaagttaatc ccggttgtgc attgaagaga tcggccagat | 420 |
| ccatcccatg tgagtacttt gaatcttgtt taaattgttt ttgatcagta ggttccctgt | 480 |
| aaaaatgtat gaactgccca ttctgtggct gaaagatagc aacttccacc ggatcattgt | 540 |
| atctaccctc aatgtctatc catgtgggtg catttggatc aatcccgctc attagatctt | 600 |
| ttaacagcat ggtttgactg tagcttaatc ccacttgggg tggccctgct gctcctggtg | 660 |
| aaggtcttgg taagtcggtc ataggcttgt caccagatag atcaattgtt gtgttttccc | 720 |
| atgcccttcc cacaacagat gtcctacagg caatgtaggg ccaaccttcc cctgacaggc | 780 |
| agatcttgta caagatgttc tcataagggt ttctgtctcc cacttggtct gagacaaaca | 840 |
| tattaaactt gcgttttgcc ccgagaactg cttttaggag ttcctcagaa ttgctgggct | 900 |
| taattaggat tgattccaac atattgcccc catccagcaa tgcggctcct gctttgacag | 960 |
| ctgcacccaa actgaagttg tacccagata tattgatgct ggattgctgc tcggttatca | 1020 |
| cacccagaac tgggtgtttg tctttcagcc tgtcaagatc cgacaaattg gggtatttga | 1080 |
| ctgtgtagag caggcccagg tctgtgagtg cttgcacaac atcgtttaaa ggggtctgtg | 1140 |
| cctgtttggc aatacaagcc attgtcaagc tgggcattgt gccaaattga ttgttcaaaa | 1200 |
| gtgatgagtc cttcacatcc caaactctga caccccatt gtttccctgc tggggcctcc | 1260 |
| tcatcccaac catttgtaga atttgagatc tttggtcgag ctgctgtgtt gtcagattgc | 1320 |
| ccatatagac ccctgatgct tgtggtctct ctgatctcat tatcttggct ttcagctttt | 1380 |
| ctagatcagc tgctaaagac attaactcct ctgcattgag tctgcccact tttagaatgt | 1440 |
| tcttcttaga cgtggatttt aactccacaa gggagtgtac tgtctggttc aggctcctca | 1500 |
| gtctctgcag atctttgtca tctctcctat cctttctcat aattctctga acgttgctaa | 1560 |
| cttcagagaa gtcaagtcca ttgagaagac tagtggcatc cttgatgaca gcagccttaa | 1620 |
| catttgaggt gaaaccctgt agctctctcc tcagtgcctg tgtccactgg aaactcttga | 1680 |

```
tctccttgga cagagacatt gtggtgatgc tcactgtgtc tccaacaaaa gcgcaatcaa   1740
atgcctagga tccactgtgc g                                              1761

<210> SEQ ID NO 11
<211> LENGTH: 1774
<212> TYPE: DNA
<213> ORGANISM: Lymphocytic choriomeningitis virus
<220> FEATURE:
<221> NAME/KEY: modified_base
<222> LOCATION: (1692)..(1692)
<223> OTHER INFORMATION: a, c, t, g, unknown or other

<400> SEQUENCE: 11
aggtggagag tcagggaggc cccgtgggga ccttagagtg tcacaacatt tggacccctg     60
aagattaggt catgtggcaa aatgttatgg atgttcttca gttcgggcag cctggccttt    120
gaagcagctt caaaaatgat gcagtccata agagcacaat gaggtgtgat ctccttcttt    180
ttcttgtcct tcactacccc agtgtgcatc ttgcacagcc atccataatt gtcccagact    240
ttgtcctcat actctctgga tgcctccctt gacatctcta catcaatcaa tttgatgtcc    300
ctcctgtttt gggaatcaag aagctttctg atgtcatctg agccctgaca gctaaggacc    360
atcccttgtg gtaaagcacc gatgactgat gatgtcagcc ctggttgtgc attgaaaagg    420
tcagcaaggt ccataccatg tgagtacttt gagtcttgtt tgaattgttt ctggtcagct    480
ggttctctgt aaaaatgaat gaactgacca ttttgaggtt gaaatagagc aacctcaaca    540
ggatcattga atcttccctc aatgtcaatc catgtgggtg cattaggatc aatgccactc    600
attaggtcct ttaacagcat ggtttggctg taacttagac caacctgggg tggtcctgca    660
gcacctgggg ttggtcttgg ggtattagtg atcagtttgt cacctgacag gtcaatggtt    720
gtgttctccc aagctcttcc aacaacagat gttctacaag caatataagg ccacccctca    780
ccggacaagc agaccttgta caagatgttt tcataagggt ttctgtcccc aacctggtct    840
gacacaaaca tattcagctt tcgctttgca ccaagaactg ctttcaggag atcctcagag    900
ttgcttggct ttattaagat agactctagc atgttacccc catctaacag tgcggctcca    960
gcttttacag ccgcacctaa gctgaagttg tatccagata tgtttatgct tgattgttgc   1020
tctgtgatga cacccagaac cggatgtttg tctttcaacc tctcaaggtc agaaaggttg   1080
gggtacttta ctgtatagag taaccccagg tctgtgagcg cctgaacaac atcatttaat   1140
ggagtctgtg attgtttggc catgcaagcc attgtcaggc tgggcatcgt tccaaattgg   1200
ttgttcaaga gagaggaatc cttgacatcc cagactctaa caacaccatt gttcccttgc   1260
tggggtctcc tcatcccgac catttgtagg atttgagatc tttggtctag ttgctgggtt   1320
gtcaggttcc ccatgtacac acctgaggcc tgcggcctct cggttctgat tattttggct   1380
tttagctttt caaggtcagc tgcaagggac attagttcct ctgcactgag tctcccaact   1440
tttaggatat tcttttttga ggttgatttc agctccacca aggaatggac agtctggttg   1500
aggctcctaa gtctctgcag atctttatcg tccctcttgt ccttcctcat gatcctctga   1560
acattgctga cttcagagaa gtcaagccca ttcaaaaggc tggtagcatc tttaatcacg   1620
gcagctttaa cattcgaggt gaacccctgc aattccctcc tcaatgcctg agtccattga   1680
aagctcttga cntccttgga cagggacatt ctgatgggca ccactgtgtc actggcaatt   1740
gcgcaatcaa tttgcctagg atccacggtg cgaa                               1774

<210> SEQ ID NO 12
```

<211> LENGTH: 1615
<212> TYPE: DNA
<213> ORGANISM: Lymphocytic choriomeningitis virus

<400> SEQUENCE: 12

```
taccagggga atcctaggct ttttggattg cgcatttctt taggtcaact aagtgtcaaa      60
ctttgtccca cacaaagatg ggtcaaatta tgacaatgtt tgaggcgttg cctcacatca     120
ttgatgaagt catcaacatt gtcattattg tactcatcat aatcaccagt attaaagctg     180
tgtacaattt tgccacctgc ggaatattcg cattggtcag cttccttctc ctagccggta     240
ggtcctgcgg tatgtacggt ctcaatggac ccgacattta caagggatt taccagttca      300
aatcagtgga gtttgatatg tcacatttga acctgacaat gcccaatgca tgttcagcca     360
ataattccca ccactacatc agcatgggga gttctggact ggaactgacc ttcaccaatg     420
attctattct cagccacaat ttttgcaacc taacctctgc tttcaacaag aagaccttcg     480
accacacact catgagcata gtctcaagtc tacaccttag catcagggga aactccaatt     540
acaaagcagt gtcttgtgat ttcaacaatg gcatcacaat ccaatacaac ctgacgtttt     600
cagatgtgca gagtgccaac aaccagtgca gaacttttag aggtagagtt ctagacatgt     660
ttagaactgc ttttggtggg aagtatatgc gaagtgggtg gggctgggca ggttcagatg     720
gcaaaaccac ttggtgcagc cagacaagct atcaatatct aatcatacaa aacagaactt     780
gggaaaatca ctgcacctac gcaggtcctt ttggaatgtc tagaatcctt tttgctcagg     840
aaaagacaaa gttcctcact agaagacttg caggcacatt cacttggact ctgtcagact     900
cttcgggatc agaaaatcca gatggatatt gtttgactaa atggatgatt ttggctgcag     960
aactcaaatg ctttgggaac acggctgttg caaagtgcaa cgtcaatcat gatgaggagt    1020
tctgtgacat gctgcgacta attgattata caaggctgc actaacaaaa ttcaagcaag    1080
atgttgagtc tgccttacac ctatttaaga caactgtcaa ttctctgatt ccgatcagc    1140
tattgatgag gaaccattta agagatttga tgggggtacc atactgcaat tactcaagat    1200
tctggtactt aaaacatgca aaaactggtg agaccagtgg gccaaagtgc tggcttgtca    1260
ccaacggttc ttatttaaat gaaacccact taagtgacca aatagaacaa gaagcagaca    1320
acatgattac agaaatgctg aggaaagact acataaaaag acaggggagt acccctctag    1380
ccttgatgga tatttgatg ttttctacat cagcatacct tataagcatt ttttgcatc     1440
ttgtgaagat accaacacac agacacataa aggtggctc atgtccaaaa ccacaccgtt    1500
tgaccggcaa gggaatttgc agttgtggtg ctttaaggt gccaggagtg aaaactgtct    1560
ggaagagacg ctgaacaacg gcgcctccct ggctttccac ctcagaagag gggag        1615
```

<210> SEQ ID NO 13
<211> LENGTH: 1661
<212> TYPE: DNA
<213> ORGANISM: Lymphocytic choriomeningitis virus

<400> SEQUENCE: 13

```
cgcaccgggg atcctaggct ttttggattg cgctttcctt taggacaact gggtgctgga      60
ttctatccag taaaaggatg ggtcagattg tgacaatgtt tgaggctttg cctcacatca     120
ttgatgaggt catcaacatt gtcattattg tgctcattat aatcacgagc atcaaagctg     180
tgtacaattt cgccacctgt gggatattag cactggtcag cttccttttt ctggctggta     240
ggtcctgtgg catgtacggc cttaatggtc ccgatatcta taagggggtt taccagttca     300
aatcagtgga gtttgatatg tctcacttaa atctgacgat gcccaatgcg tgctcagtca     360
```

```
acaactctca tcactacatc agtatgggaa gctctggact ggagccaact ttcaccaacg     420
actccatcct taatcacaac ttctgcaact taacctccgc tctcaacaaa aagtcttttg     480
accatacact catgagtata gtctcgagtc tacacctcag tatcagaggg aattccaact     540
acaaagcagt gtcttgtgat tttaacaatg gcatcaccat tcaatacaac ttgtcatctt     600
cggacccaca gagcgccatg agccagtgta ggactttcag aggtagagtc ttggacatgt     660
ttagaactgc ctttggagga aagtacatga gaagtggctg ggctggaca ggttcagatg      720
gcaagaccac ttggtgcagc caaacaagct atcagtacct aatcatacaa aacaggactt     780
gggaaaacca ctgtagatat gcaggccctt ttgggatgtc tagaatcctc tttgctcagg     840
aaaagacaaa gtttctcact aggagacttt caggcacatt cacctggacc ctgtcagact     900
cctcaggagt agaaaatcca ggtggttatt gcctgaccaa atggatgatc cttgctgcag     960
agctcaaatg ttttgggaat acagctgttg caaaatgtaa tgtcaatcat gatgaagagt    1020
tctgtgacat gctacgacta attgattaca acaaggctgc cctgagtaag ttcaagcaag    1080
atgtagagtc tgccttgcat gtattcaaaa caacattaaa ttctctgatt tccgatcagc    1140
tgttgatgag gaatcatcta agagatctaa tgggggtacc atactgtaat tactcaaagt    1200
tctggtatct ggaacatgct aagactggtg agactagtgt acccaagtgt tggcttgtca    1260
ctaatggctc ctacttgaat gagacccatt ttagtgatca aatcgaacaa gaagcagata    1320
acatgatcac agagatgttg aggaaggact acataaaaag acaagggagt actcctttag    1380
ccttaatgga tcttttgatg ttttcaacat cagcatactt gatcagcatc tttctgcatt    1440
ttgtgaggat accaacacat agacacataa agggcggttc atgtccaaag ccacatcgct    1500
tgaccaacaa ggggatctgt agttgtggtg cattcaaggt gcctggtgta aaaactatct    1560
ggaaaagacg ctgatcagca gcgcctccct gactctccac ctcgaaagag gtggagagtc    1620
agggaggccc agcgggtctt agagtgtcac aacattgggt c                       1661
```

<210> SEQ ID NO 14
<211> LENGTH: 1661
<212> TYPE: DNA
<213> ORGANISM: Lymphocytic choriomeningitis virus

<400> SEQUENCE: 14

```
cgcaccgggg atcctaggct ttttggattg cgctttcctc tagatcaact gtgtgttgga      60
ctctatcctg tcgaaggatg ggtcaaattg tgacaatgtt tgaggccttg cctcacatta     120
ttgatgaagt catcaatatt gtcatcattg tgctcataat aatcaccagc ataaaggctg     180
tgtacaacct tgccacctgt gggatatttg cattggtcag cttcctcctc ttggctggga     240
gatcatgtgg catgtatggt ctcagtgggc ctgacatcta caaaggtgtt taccagttca     300
aatcagtaga atttgacatg tcacacctga acttaacaat gcccaatgca tgctcagcca     360
acaattccca ccattacatc agcatgggga cttcagggct ggaattgact ttcaccaatg     420
actccatcat tgaccacaag ctctgtaact tgacttctgc tttcaataag aagacctttg     480
accacaccct catgagcata gtgtccagcc tacaccttag tatcagaggg aattcgaatt     540
acaaagcagt atcttgtgat ttcaacaatg gcatcaccat tcaatacaac ttgacatttt     600
cagacgcaca gagtgctttg agccagtgca ggactttcag aggtagagtc ttggacatgt     660
tcagaactgc ttttggtgga aagtacatga ggagtggttg ggctggact ggctcggatg      720
gtaggaccac ctggtgtagc cagacgagtt atcaatacct aatcatacaa aatcggacct     780
```

```
gggagaacca ctgtagatat gcagggccct ttggaatgtc cagaatcctc tttgctcagg      840
aaaagacaaa gttcctcact agaaggcttg ccggtacatt cacctggact ctgtcagact      900
cttcaggagt agaaaaccca ggcggttact gcctgaccaa gtggatgatt cttgctgcag      960
aactcaagtg ttttgggaac acagctgttg caaaatgcaa tgtcaatcat gacgaagagt     1020
tctgtgacat gctacgatta attgattaca ataaggctgc attgagtaag tttaaggaag     1080
atgtagaatc tgcttttgcac ttgtttaaaa caacagtaaa ttctttgatt tccgaccaag    1140
tgctcatgag gaatcactta agagacttga tgggagtgcc atactgcaac tattcaaaat     1200
tctggtatct ggagcacgca aagactggtg aaaccagtgt tcctaagtgt tggcttgtca     1260
ctaacggctc ttatttaaat gagacccatt ttagtgatca aatagagcaa gaggcggaca     1320
acatgatcac agagatgctg aggaaggact atatcaagag gcagggaagc acccccttag     1380
ccttaatgga tcttttgatg ttttccacgt cagcctatct aattagtgtc ttcctgcatc     1440
ttatgaaaat accaacgcac agacacataa agggcggttc atgcccaaag ccacatcgtt     1500
tgaccaacaa ggggatctgt ggctgtggtg cattcagggg acccggtgta aaaactgttt     1560
ggaagagacg ctgagcaaca gcgcctcccct gactctccac ctcgaaagag gtggagagtc    1620
agggaggccc agagggtctt agagtgtcac aacatttgga c                         1661

<210> SEQ ID NO 15
<211> LENGTH: 1641
<212> TYPE: DNA
<213> ORGANISM: Lymphocytic choriomeningitis virus

<400> SEQUENCE: 15
tttttggatt gcgctttcct ttaggtcaac tgaggatcga gtttaccttg tggaaggatg       60
ggtcaaattg tgacgatgtt tgaggctttg cctcacatca tcgatgaagt gatgaatatt     120
gtcatcattg tgctcattat aatcacaagc atcaaagctg tgtataactt tgccacttgt     180
gggatattca cactggttag ctttctcctt ctagctggca ggtcctgtgg tatgtacggc     240
cttaagggac ctgacattta caagggagtc taccaactca agtcagtgga atttgacatg     300
tcacatctga acttgacaat gcccaacgca tgctcagcta taattctca ccactacatt      360 agcatgggga atctgggct agaactaacc ttcaccaatg actccatcat cagtcacaac      420
cactgtaatt tgacttctgc ctttaacaag aaaacccttg atcacacact tatgagcata     480
atttctagcc tacatcttag tattagggga aactctaatt acaaggcagt tcctgtgat     540 ttcaacaatg gcatcaccat ccaatacaac ctgacattct ctgatgcaca gagtgctctg      600
agccaatgca ggaccttcag gggcagagtg ctagacatgt ttagaactgc cttcggggga     660
aagtacatga ggagtggttg gggctggaca ggttcagatg gcaaaaccac atggtgtagt     720 cagacaaaact atcaatactt gatcatacaa aatagaacct gggataacca ctgcacgtat    780 gcaggcccctt ttggaatgtc tagaatcctc tttgcccaag agaaaacaaa gtttatcact    840
agaagacttg caggcacatt cacttggacc ttgtctgatt cctcaggagt agaaaatcca    900
ggtggctact gcttgacaag gtggatgatt attgctgcag atctcaaatg ctttgggaac     960
acagctgttg caaagtgcaa tgtaaatcat gatgaagagt ctgtgacat gttacgatta    1020 attgattaca acaaagctgc cttgacaaag ttcaagaag atgtggaatc cgccctacac     1080
ctattcaaga caacagtaaa ctctctgatt tccgatcagc tactaatgag aaaccacctg    1140
agggatttaa tgggagtgcc atattgtaac tactcaaagt tctggtattt ggaacatgcg     1200
aagactggtg aaactagtgt tccgaaatgt tggcttgtca ccaacggctc ctacttaaat    1260
```

-continued

```
gagacccatt ttagcgatca gattgagcag gaagcagaca acatgattac ggagatgctg    1320
agaaaagatt atataaagag gcaaggaagc acccctttgg ctttaatgga tcttttaatg    1380 tttttccacat ctgcatattt aatcagcatt tttatgcatc tcatgaagat acctacacac    1440
agacatataa aaggtggatc atgtccaaaa ccgcaccgtt taaccagcaa agggatttgt    1500
agttgtggtg catttaaagt tcctggtgta aggaccgttt ggaagagacg ctgagcaaca    1560
gcgcctccct gactctccac ctcagaagag gtggagagtc agggaggccc agcgggtctc    1620
aaagtgtcac aacatttggt c                                             1641
```

<210> SEQ ID NO 16
<211> LENGTH: 1641
<212> TYPE: DNA
<213> ORGANISM: Lymphocytic choriomeningitis virus

<400> SEQUENCE: 16

```
tttttggatt gcgctttcct ttaggtcaac tgaggatcga gtttaccttg tggaaggatg      60
ggccaaattg tgacgatgtt tgaggctttg cctcacatca tcgatgaagt gatgaatatt     120
gtcatcattg tgctcattat aatcacaagc atcaaagctg tgtataactt tgccacttgt     180
gggatattca cactggttag cttttctcctt ctagctggca ggtcctgtgg tatgtacggc    240
cttaagggac ctgacattta caagggagtc taccaactca agtcagtgga atttgacatg    300
tcatatctga acttgacaat gcccaacgca tgctcagcta caattctca ccactacatt     360 agcatgggga aatctgggct agaactaacc ttcaccaatg actccatcat cagtcacaac    420
cactgcaatt tgacttctgc ctttaacaag gaaacctttg atcacacact tatgagcata    480
atttctagcc tacatcttag tattagggga aactctaatt acaaggcagt ttcctgtgat    540
ttcaacaatg gcatcaccat ccaatacaac ctgacattct ctgatgcaca gagtgctctg    600
agccaatgca ggaccttcag gggcagagtg ctagacatgt ttagaactgc cttcggggga    660
aagtacatga ggagtggctg gggctggaca ggttcagatg gcaaaaccac atggtgtagt    720 cagacaaaact atcaatactt gatcatacaa aatagaaccct gggataacca ctgcacgtat    780 gcaggcccctt ttggaatgtc tagaatcctc tttgcccaag agaaaacaaa gtttatcact    840
agaagacttg caggcacatt cacttggacc ttgtctgatt cctcaggagt agaaaatcca    900
ggtggctact gcttgacaag gtggatgatt attgctgcag atctcaagtg ctttgggaac    960
acagctgttg caaatgcaa tgtaaatcat gatgaagagt tctgtgacat gttgcgatta    1020
attgattaca caaagctgc cttgagaag ttcaaagaag atgtggaatc cgccctacac    1080
ctattcaaga caacagtaaa ctctctgatt tccgatcagc tactaatgag aaaaccacctg    1140 agggatttaa tgggagtgcc atattgtaac tactcaaagt tctggtattt ggaacatgcg    1200
aagactggtg aaactagtgt tccgaagtgt tggcttgtca ccaacggctc ctacttaaat    1260
gagacccatt ttagcgatca gattgagcag gaagcagaca acatgattac ggagatgctg    1320
agaaaagatt atataaagag gcaaggaagc acccctttgg ctttaatgga tcttttaatg    1380 tttttccacat ctgcatattt aatcagcatt tttatgcatc tcatgaagat acctacacac    1440
agacatataa aaggtggatc atgtccaaaa ccgcatcgtt taaccagcaa agggatttgt    1500
agttgtggtg catttaaagt tcctggtgta aggaccgttt ggaagagacg ctgagcaaca    1560
gcgcctccct gactctccac ctcagaagag gtggagagtc agggaggccc agcgggtctc    1620
aaagtgtcac aacatttggt c                                             1641
```

<210> SEQ ID NO 17
<211> LENGTH: 1661
<212> TYPE: DNA
<213> ORGANISM: Lymphocytic choriomeningitis virus

<400> SEQUENCE: 17

| | | | | | |
|---|---|---|---|---|---|
| cgcaccgggg | atcctaggct | ttttggattg | cgctttcctc | tagatcaact | gggtgtcagg | 60 |
| ccctatccta | cagaaggatg | ggtcagattg | tgacaatgtt | tgaggctctg | cctcacatca | 120 |
| tcgatgaggt | gatcaacatt | gtcattattg | tgcttatcgt | gatcacgggt | atcaaggctg | 180 |
| tctacaattt | tgccacctgt | gggatattcg | cattgatcag | tttcctactt | ctggctggca | 240 |
| ggtcctgtgg | catgtacggt | cttaagggac | ccgacattta | caaggagtt | taccaattta | 300 |
| agtcagtgga | gtttgatatg | tcacatctga | acctgaccat | gcccaacgca | tgttcagcca | 360 |
| acaactccca | ccattacatc | agtatgggga | cttctggact | agaattgacc | ttcaccaatg | 420 |
| attccatcat | cagtcacaac | ttttgcaatc | tgacctctgc | cttcaacaaa | aagacctttg | 480 |
| accacacact | catgagtata | gtttcgagcc | tacacctcag | tatcagaggg | aactccaact | 540 |
| ataaggcagt | atcctgcgac | ttcaacaatg | cataaccat | ccaatacaac | ttgacattct | 600 |
| cagatcgaca | aagtgctcag | agccagtgta | gaaccttcag | aggtagagtc | ctagatatgt | 660 |
| ttagaactgc | cttcgggggg | aaatacatga | ggagtggctg | gggctggaca | ggctcagatg | 720 |
| gcaagaccac | ctggtgtagc | cagacgagtt | accaataccct | gattatacaa | aatagaacct | 780 |
| gggaaaacca | ctgcacatat | gcaggtcctt | tgggatgtc | caggattctc | ctttcccaag | 840 |
| agaagactaa | gttcttcact | aggagactag | cgggcacatt | cacctggact | tgtcagact | 900 |
| cttcaggggt | ggagaatcca | ggtggttatt | gcctgaccaa | atggatgatt | cttgctgcag | 960 |
| agcttaagtg | tttcgggaac | acagcagttg | cgaaatgcaa | tgtaaatcat | gatgccgaat | 1020 |
| tctgtgacat | gctgcgacta | attgactaca | acaaggctgc | tttgagtaag | ttcaaagagg | 1080 |
| acgtagaatc | tgccttgcac | ttattcaaaa | caacagtgaa | ttctttgatt | tcagatcaac | 1140 |
| tactgatgag | gaaccacttg | agagatctga | tggggtgcc | atattgcaat | tactcaaagt | 1200 |
| tttggtacct | agaacatgca | aagaccggcg | aaactagtgt | ccccaagtgc | tggcttgtca | 1260 |
| ccaatggttc | ttacttaaat | gagacccact | tcagtgatca | aatcgaacag | gaagccgata | 1320 |
| acatgattac | agagatgttg | aggaaggatt | acataaagag | gcaggggagt | accccctag | 1380 |
| cattgatgga | ccttctgatg | ttttccacat | ctgcatatct | agtcagcatc | ttcctgcacc | 1440 |
| ttgtcaaaat | accaacacac | aggcacataa | aaggtggctc | atgtccaaag | ccacaccgat | 1500 |
| taaccaacaa | aggaatttgt | agttgtggtg | catttaaggt | gcctggtgta | aaaaccgtct | 1560 |
| ggaaaagacg | ctgaagaaca | gcgcctccct | gactctccac | ctcgaaagag | gtggagagtc | 1620 |
| agggaggccc | agagggtctt | agagtgtcac | aacatttggg | c | | 1661 |

<210> SEQ ID NO 18
<211> LENGTH: 1584
<212> TYPE: DNA
<213> ORGANISM: Lymphocytic choriomeningitis virus

<400> SEQUENCE: 18

| | | | | | |
|---|---|---|---|---|---|
| atgggccaaa | ttgtgacgat | gtttgaggct | ctgcctcaca | tcattgatga | ggtcattaac | 60 |
| atagtcatta | tcgtgctcat | tatcatcacg | agcatcaaag | ctgtgtacaa | tttcgccact | 120 |
| tgcgggatat | ttgcattaat | cagctttctt | ctcctggctg | gcaggtcctg | tggaatgtat | 180 |
| ggtcttgatg | ggcccaacat | ttacaaaggg | gtttatcaat | tcaagtcagt | agagtttgac | 240 |

```
atgtctcacc ttaatctgac gatgcccaat gcatgttcgg caaacaactc ccatcattat      300
ataagtatgg ggacttctgg attggagtta accttcacaa atgactccat catcagtaac      360
aaaccttgta atctgtcttc ctccttccag aaggaaactt ttgaccacac acttatgagc      420
atagtcacaa gtctgcacct cagcatcaga ggaagcacca accgcaaagc agtgtcctgt      480
gattttaaca atggcatcac tattcaatac aatctgtcat tttctgatgc acagagcgct      540
ctgagtcaat gcaggacttt cagagggaga gtcctggata tgttcagaac tgcttttggg      600
ggaaagtaca tgaggagtgg ctggggctgg acaggttcag atggcaagac cacttggtgc      660
agccagacaa actatcaata tctgatcata caaaacagaa cttgggaaaa ccactgcaga      720
tacgcaggcc ctttcggaat gtccagaatc ctcttcgctc aagaaaagac aaggtttcta      780
actaggaggc ttgcaggcac attcacttgg actttatcag actcatcagg agtggagaat      840
ccaggtggtt actgcttgac caagtggatg atcyttgctg cagagctcaa atgttttggg      900
aacacagctg tagcaaagtg caatgtgaat catgatgaag agttctgtga tatgctacgg      960
ctgattgatt acaacaaggc tgctttgagt aaattcaaag aggatgtgga atctgctctg     1020
catctgttta agacaacagt gaattctctg atttctgatc agcttttgat gagaaatcat     1080
ttaagagact tgatgggagt gccatactgc aattactcga aattctggta tctagagcat     1140
gcaaggactg tgagactagt gtccccaagt gctggcttg tcagcaatgg ttcttatttg     1200
aatgaaaccc atttcagtga ccaaattgag caggaagcag acaatatgat cacagaaatg     1260
ctgagaaagg actacataaa aaggcaagga agcacccctc tagccttgat ggacctgttg     1320
atgtttttcca catcggcata cttgatcagc atctttctgc atcttgtgaa gataccaaca     1380
cacagacaca taaagggcgg ctcatgccca aaaccacatc ggttaaccag catgggaatc     1440
tgtagttgtg gcacattcaa agtgccaggt gtggaaacca cctggaagag acgctgaaca     1500
gtagcgcctc cctgactcac cacctcgaaa gaggtggtga gtcagggagg cccagagggt     1560
cttagagtgt tactacattt ggac                                             1584
```

<210> SEQ ID NO 19
<211> LENGTH: 1643
<212> TYPE: DNA
<213> ORGANISM: Lymphocytic choriomeningitis virus
<400> SEQUENCE: 19

```
cgcaccgggg atcctaggct ttttggattg cgctttcctc aggtccatct tgtagaagaa       60
tgggccaaat agtgacgatg ttcgaggctc tgcctcacat catcgatgaa gtcatcaaca      120
ttgtcatcat cgtgctcatc attatcacga gcatcaaagc tgtgtacaat ttcgccacct      180
gcgggatact tgcactgatc agctttcttt tcctggctgg caggtcctgt ggtatgtatg      240
gtcttagtgg gcctgacatc tacaagggag tttaccaatt taagtcagtg gagtttgata      300
tgtcccacct caacctgacg atgcccaatg catgttcggt gaacaactcc catcattaca      360
taagcatggg gacttctggg ttggagttga cctttacaaa tgactccatt atcaaccaca      420
acttttgtaa tctgacttct gctttcaaca agaaaacctt tgaccacaca ctcatgagta      480
tagtttcgag cctgcacctc agcattagag gaaactccaa ctacaaggcg tgtcctgtg     540
atttcaacaa cggcatcact attcaataca acttgacatt ctctgatgca aagagcgctc      600
tgagccagtg caggacttc aggggaagag ttttggacat gttcagaact gcttttggag      660
gaaaatacat gaggagtggc tggggttgga caggttcaga tggcaaaact acttggtgca      720
```

| | |
|---|---|
| gccagacaag ctatcaatat ctaatcatac aaaatagaac ttgggaaaac cactgcagat | 780 |
| acgcaggccc tttcgggata tctagaatcc tctttgctca agaaaagaca aagtttctta | 840 |
| ctaggaggct tgcaggcaca ttcacctgga ctttatcaga ctcatcagga gtagagaatc | 900 |
| caggtggtta ttgcttgacc aggtggatga tccttgctgc agagctcaag tgttttggaa | 960 |
| acacagctgt tgcaaaatgc aatgtaaatc atgatgagga attctgtgac atgctacgat | 1020 |
| tgattgatta caacaaggct gctctaagca agttcaaaga agatgtagaa tctgcattac | 1080 |
| acttgtttaa aacaacagtg aattctctga tttctgatca gcttctgatg aggaatcacc | 1140 |
| tgagagactt aatgggggtg ccatactgca actactcaaa attttggtat ctggagcatg | 1200 |
| caaagaccgg tgagactagt gtccccaaat gctggcttgt tagcaatggt tcttacttga | 1260 |
| atgaaaccca tttcagtgac caaattgaac aggaagcaga caacatgatc acagaaatgc | 1320 |
| tgagaaagga ttacataaaa aggcaaggga gcacccccTT agctttgatg gatctgctaa | 1380 |
| tgttttctac atcagcatat ttgatcagca tcttcttaca tcttataaag ataccaacac | 1440 |
| acagacacgt aaagggcggc tcatgcccaa agccacaccg gttaaccagc aaaggaatct | 1500 |
| gtagctgtgg tgcgttcaag gtgcctggtg tgaaaaccat ctggaaaaga cgctgaacag | 1560 |
| cagcgcctcc ctgactctcc acctcgaaag aggtggagag tcagggaggc ccagagggtc | 1620 |
| tcagagtgtc acgacatttg gac | 1643 |

<210> SEQ ID NO 20
<211> LENGTH: 1665
<212> TYPE: DNA
<213> ORGANISM: Lymphocytic choriomeningitis virus

<400> SEQUENCE: 20

| | |
|---|---|
| tcgcaccggg gatcctaggc ttattatatt gcgctttgta ttgaagtctg ttctgtgtgg | 60 |
| actgacctca gcacaagtgt tatggggcag atcataacaa tgtttgaggc cctgcctcac | 120 |
| attatcgatg aggtcatcaa cattgttata atagtgctta ataataacaa agcataaag | 180 |
| gctgtgtaca actttgctac ctgtggcatc attgcattga tcagcttctg cttcttggct | 240 |
| ggaaggtctt gtggcttgta tggtgtctct ggctctgaca tttacaaggg actctaccag | 300 |
| ttccagtccg tagagttcaa catgtcacaa ttgaatttaa caatgcccaa tgcgtgctca | 360 |
| gccaacaatt cccaccatta tcatcagcatg gaaaatctg gcctggaact aacctttaca | 420 |
| aatgactcca tcattcaaca caacttctgc aacctaactg atgggttcaa gaaaaaaacc | 480 |
| tttgatcata cacttatgag catagtgtca agcctgcacc tgagcattag aggaaatacc | 540 |
| atctacaaag ctgtgtcctg tgacttcaac aatgggatta caatccagta caacctaacc | 600 |
| ttctctgatg cacaaggtgc catcaatcaa tgtggaacct tcagaggtag agttttagat | 660 |
| atgtttagaa cagcttttgg ggggaaatac atgaggtctg gctatggttg gaaagactcc | 720 |
| aatgggaaga caacctggtg cagtcaaacc aactatcaat acctaatcat acagaacagg | 780 |
| acatgggaaa tcactgtgga gtatgccggt ccttttggtc tctcaagaat tcttttgct | 840 |
| caggagaaaa caaagtttct cactagaaga ttggcaggga cttttacctg acattgtcg | 900 |
| gattcttcgg gaactgaaac cccaggtggg tattgtctga caaggtggat gctcatagct | 960 |
| gctgatctca agtgtttcgg gaacacagca gttgccaaat gcaacatcaa ccatgatgaa | 1020 |
| gaatttgtg acatgttgag gttaattgac tataacaaag ccgctctaaa gaaattcaaa | 1080 |
| gaagacgtag agtctgccct tcacttgttc aaaacaactg tgaattcctt aatatctgac | 1140 |
| cagttgttga tgaggaatca tctaaggggat ctgatgggcg taccctattg caactactca | 1200 |

```
aaatttggt acttacagca tgtaaaaaca ggtgagatga gtgctcctaa gtgctggttg      1260
gtcaccaatg gctcatacct gaatgagacc cattttagtg accaaataga gcaggaggca      1320
gacaatatga ttactgaaat gcttagaaaa gactacatta agaggcaagg aagcactcct      1380
ttggcattaa tggatctttt gatgttttcc acatcagcat atttgatcag cattttcctt      1440
catctgatga aaatcccaac ccacagacac attaaaggcg gcacatgccc taaaccacac      1500
agactaacta gcaaaggcat tgtagttgt ggtgcattca gagtgccagg agtgaagaca      1560
gtttggaaga gacgctagac aacagcgcct ccctgactct ccacctctga gaggtggaga      1620
gtcagggagg ccctttgagg gttcagaggg tcacaacatt tggac                     1665
```

<210> SEQ ID NO 21
<211> LENGTH: 1665
<212> TYPE: DNA
<213> ORGANISM: Lymphocytic choriomeningitis virus

<400> SEQUENCE: 21

```
tcgcaccggg gatcctaggc ttattatatt gcgctttgta ttgaagtctg ttctgtgtgg       60
actgacctca gcacaagtgt tatggggcag atcataacaa tgtttgaggc cctgcctcac      120
attatcgatg aggtcatcaa cattgttata atagtgctta ataataaac aagcataaag       180 gctgtgtaca actttgctac ctgtggcatc attgcattga tcagcttctg cttcttggct      240
ggaaggtctt gtggcttgta tggtgtctct ggctctgaca tttacaaggg actctaccag      300
ttccagtccg tagagttcaa catgtcacaa ttgaatttaa caatgcccaa tgcgtgctca      360
gccaacaatt cccaccatta tcatcagcatg ggaaaatctg gcctggaact aacctttaca      420
aatgactcca tcattcaaca caacttctgc aacctaactg atgggttcaa gaaaaaaacc      480
tttgatcata cacttatgag catagtgtca agcctgcacc tgagcattag aggaaatacc      540
atctacaaag ctgtgtcctg tgacttcaac aatgggatta caatccagta caacctaacc      600
ttctctgatg cacaaggtgc catcaatcaa tgtggaacct tcagaggtag agttttagat      660
atgtttagaa cagcttttgg ggggaaatac atgaggtctg gctatggttg aaagactcc      720 aatgggaaga caacctggtg cagtcaaacc aactatcaat acctaatcat acagaacagg      780
acatgggaaa atcactgtga gtatgccggt ccttttggtc tctcaagaat tcttttgct       840 caggagaaaa caaagtttct cactagaaga ttggcaggga cttttacctg acattgtcg      900 gattcttcgg gaactgaaac cccaggtggg tattgtctga caaggtggat gctcatagct      960
gctgatctca agtgtttcgg gaacacagca gttgccaaat gcaacatcaa ccatgatgaa     1020
gaattttgtg acatgttgag gttaattgac tataacaaag ccgctctaaa gaaattcaaa     1080
gaagacgtag agtctgccct tcacttgttc aaaacaactg tgaattcctt aatatctgac     1140
cagttgttga tgaggaatca tctaagggat ctgatgggcg tacctattg caactactca     1200 aaatttggt acttacagca tgtaaaaaca ggtgagatga gtgctcctaa gtgctggttg     1260
gtcaccaatg gctcatacct gaatgagacc cattttagtg accaaataga gcaggaggca     1320
gacaatatga ttactgaaat gcttagaaaa gactacatta agaggcaagg aagcactcct     1380
ttggcattaa tggatctttt gatgttttcc acatcagcat atttgatcag cattttcctt     1440
catctgatga aaatcccaac ccacagacac attaaaggcg gcacatgccc taaaccacac     1500
agactaacta gcaaaggcat tgtagttgt ggtgcattca gagtgccagg agtgaagaca      1560
gtttggaaga gacgctagac aacagcgcct ccctgactct ccacctctga gaggtggaga     1620
```

```
gtcagggagg cccttttgagg gttcagaggg tcacaacatt tggac              1665
```

<210> SEQ ID NO 22
<211> LENGTH: 1557
<212> TYPE: DNA
<213> ORGANISM: Lymphocytic choriomeningitis virus

<400> SEQUENCE: 22

```
gttagcccta gtcatgcagc accatggggc agctcataac gatgtttgag gctttacctc    60
acgtcattga tgaagtcatc aacatcgtca ttatagtgct tgttataata acaagcataa   120
aggctgtgta caattttgcc acctgtggca tcattgcact catcagcttt tgcctcctgg   180
ctggtagatc atgtgggtca tacggtgtct ctgatcctca cattttcaaa ggactctacc   240
attttaggtc cgtagagttc aacatgtcac aattgaacct aacaatgccc aatgcatgtt   300
cagctaacaa ctctcaccat tacatcagta tggggagatc tggtttggaa ctaaccttta   360
ctaatgactc catccttcaa cacaactttt gcaacctgac tgatgggttc cggaaaaaaa   420
ccttcgacca tacgctcatg agtatagtgg caagcttgca ccttagcatc agagggaaca   480
ccgactataa agctgtgtcc tgtgacttca caatgggat cactattcaa tacaacttgt   540
cattttctga tgcacgaagt gccattaatc aatgcagaac ttttagaggc agagttttag   600
acatgttcag aacagccttt ggagggaagt acatgagatc cggctatggt tggaaggact   660
ctaacgggaa agcaacttgg tgcagtcaaa ctaattatca atacctaatt atacagaaca   720
gaacatggga aaatcactgt gagtatgccg gtccttttgg cctctcaaga attctctttg   780
ctcaagaaaa gacaaaattt ctcactagga ggctagcagg aactttcacc tggacactgt   840
cagattcctc agggactgaa accccaggtg ggtattgtct gacaaggtgg atgctcatag   900
ctgctgatct caagtgtttt ggaaacacag cagttgctag atgcaacatc aaccatgatg   960
aagaattctg tgatatgttg aggctaattg actacaacaa ggctgctctg aagaaattca  1020
aagaagacgt agagtctgcc cttcacttgt ttaagacaac agtgaattcc ttgatatctg  1080
accaattatt gatgagaaat catttgaggg atctgatggg tgtgccctat gcaactact   1140
caaaattttg gtactggag catgtaaaga caaaagaaac gagtgtccct aagtgttggt  1200
tggtcactaa tggctcatac ttgaatgaaa cacatttcag tgatcagata gaacaagagg  1260
cagacaacat gatcaccgag atgcttagga agattacat caaaaggcag ggaagtaccc   1320
ctctagcact aatggatctc ttgatgtttt ccacatcagc gtatttaatc agtgtttttc  1380
ttcatctaat gaagatcca acacatagac acatcaaggg cggcacatgc cccaaaccac  1440
atagattgac tagcaagggc atctgcagtt gtggtgcgtt taaggtgcca ggagtcaaga  1500
cggtttggga gagtcaggga ggccctcagt gggtttagag ggtcacaaca cttgggc    1557
```

<210> SEQ ID NO 23
<211> LENGTH: 1675
<212> TYPE: DNA
<213> ORGANISM: Lymphocytic choriomeningitis virus

<400> SEQUENCE: 23

```
tcgcaccggg ggatcctagg cttttgggat tgcgctttgc gttggtgaca gctaaaagag    60
agaacaggaa agttgctctc atccacagta tgggccaaat catcacaatg tttgaggctt   120
tgccctcacat cattgatgag gcaatcaaca ttgtcatgat tgtgctcata ataataacaa   180
gtctgaaagc tgtgtacaac tttgcaactt gtggcatcat agcactgatc agcttttgcc   240
tgctagctgg tagatcatgc gggatgtatg gtttgtctgg ccctgacatt tacaagggag   300
```

```
tataccagtt caaatccgtt gagtttgaca tgtcacattt gaacctgaca atgccaaatg      360
catgctctgt caacaactct catcattaca tcagcatggg aaagtctggc ctggagctaa      420
ctttcacaaa tgacagcatc cttagccaca attttttgtaa tttgactgat ggctttaaga     480
agagaacctt tgactacaca ctcatgagta ttgtggcaag tctgcacctc agcatcagag      540
gaaacaccca gtacagagct gtctcctgtg acttcaacaa tgggattacc atccaataca     600
acttgagctt cagcaccaca caaagtgctg cgaatcagtg caacactttc agaggtaggg      660
tcttggacat gtttagaacg gcatttgggg gcaagcacat gaggtcaggt tatggctgga     720
cggacgcctc tgggaagaca acctggtgca gccagactga ctatatgttc ttaataatcc     780
agaacaggac gtgggacaat cactgtcagt atgcaggtcc cttcgggctc tcaagaatcc    840
tctttgcaca agagaaaaca aaattcctga ccagaagact cgcagggact ttcacctgga     900
ctttatctga ttcatcggga actgagaatc caggtggtta ctgtttgaca aggtggatga     960
taatcgctgc agaccttaag tgctttggga atactgcagt tgcaaaatgc aacataaacc    1020
atgatgagga attttgtgat atgctaagat tgattgacta caacaaggct gctttgtcca    1080
agttcaagga agatgttgag tcagcttttgc acctgttcaa gacaacagtg aattctttga   1140
tctcagatca gttgttaatg aggaatcatc taagagacct aatgggggta ccctactgca   1200
attattcaaa attctggtac ctggaacatg caaaaacagg tgagaccagt gtgcccaagt    1260
gctggttggt gtccaatggc tcatatctga atgagacaca cttcagtgat cagattgaac    1320
aggaggctga caacatgatc actgagatgc tcagaaagga ttacatcaaa aggcagggaa    1380
gcacccccct agcattgatg gatcttctaa tgttttctac atcggcctac ttaattagca    1440
tcttcctcca tctgctgaag atccctacac atagacacat caaaggaggc tcatgtccca    1500
aaccacaccg gctcaccagt aagggtattt gtagctgcgg ggcattcaaa gtgccaggcg    1560
taaaaacagt ctggaaaaga cgctaaatga tggcgcctcc ctgactctcc acctcgaaag    1620
aggtggagag tcagggaggc cccgtgggga ccttagagtg tcacaacatt tggac          1675
```

<210> SEQ ID NO 24
<211> LENGTH: 361
<212> TYPE: DNA
<213> ORGANISM: Lymphocytic choriomeningitis virus

<400> SEQUENCE: 24

```
cgcaccgggg atcctaggcg tttagttgcg ctgctttatt gcacagcttc actctgctaa      60
actatcagga actgaccgat catcagccat gggccaaggc aagtccaaag aagaaaggca    120
atacaggcag agcagagctt tgccagacac ccacctatct tggtcctcga caccagtaaa    180
ttgtaaatca tgttggcaga aatttgacag cttggttaga tgccatgacc actatctttg    240
cagacactgt ctgaatctcc tgctgtcagt ttccgacaga tgtcctctct gtaagtatcc    300
actgccaacc aaactgaagg tgtcaacagt cccaagctcc ctacctccct atgaggagta    360
a                                                                    361
```

<210> SEQ ID NO 25
<211> LENGTH: 362
<212> TYPE: DNA
<213> ORGANISM: Lymphocytic choriomeningitis virus

<400> SEQUENCE: 25

```
cgcaccgggg atcctaggca ttttgttgcg ctatttggat gcacagtctt cctctgtgaa      60
```

```
cccattgcaa gtgaactaga ccatcagcta tgggtcaaag taaatctaag gaagagaaag      120
gcattagcgg cacgagcaga gctgagattt tgccagatac cacttatctt ggtcctctga      180
attgcaaatc atgctggcaa aaattcgaca gtttagttaa atgccatgac cactatctct      240
gcagacactg tctgaatctc ttgttgacag tctccgacag atgccctctt tgcaaatatc      300
cactgccaac caagttgaag atatcaacag ccccaagctc accgcctccc tacgaagagt      360
ga                                                                    362
```

<210> SEQ ID NO 26
<211> LENGTH: 361
<212> TYPE: DNA
<213> ORGANISM: Lymphocytic choriomeningitis virus

<400> SEQUENCE: 26

```
cgcaccgggg atcctaggcg tttagttgcg ctgtttggtt gcacaacttt cttcgtgagg      60
ctgtcagaag tggacctggc tgatagcgat gggtcaaggc aagtccagag aggagaaagg      120
caccaatagt acaaacaggg ccgaaatcct accagatacc acctatcttg gccctttaag      180
ctgcaaatct tgctggcaga aatttgacag cttggtaaga tgccatgacc actacctttg      240
caggcactgt ttaaaccttc tgctgtcagt atccgacagt gtcctctttt gtaaatatcc      300
attaccaacc agattgaaga tatcaacagc cccaagctct ccacctccct acgaagagta      360
a                                                                     361
```

<210> SEQ ID NO 27
<211> LENGTH: 362
<212> TYPE: DNA
<213> ORGANISM: Lymphocytic choriomeningitis virus

<400> SEQUENCE: 27

```
cgcaccgggg atcctaggca tttccttgcg ctattttatt gcatcgcctt ttcctgcaag      60
accacctggg gcgaagtggg ccatcagcca tgggtcaagc caagtctaga ggtagagaga      120
atgctggcaa gatggacaga gctgagattc tgccagatac cacctacctt ggacccttga      180
actgcaagtc atgctggcag aaactcgaca gtcagtcag gtgtcatgat cactacctttt    240 gcagaaattg cctgaacctt ctcttaacag tgtctgacag gtgccctctc tgcaaacatc      300
cattgccaac caggctcacg atctcaacag ccccgagctc accgcctccc tacgaggagt      360
ga                                                                    362
```

<210> SEQ ID NO 28
<211> LENGTH: 361
<212> TYPE: DNA
<213> ORGANISM: Lymphocytic choriomeningitis virus

<400> SEQUENCE: 28

```
cgcaccgggg atcctaggcg gtttgttgcg ctgtttagtg gcctacatct ccttcacaag      60
accaccagag cacagcaagt cactagccat gggtcaaggt aaatccaagg gggaaagaga      120
aatcagcagt gcgcaaaggg ctgagattct gccagacacc acatatcttg gtcctctaaa      180
ctgcaagtca tgctggcaga ggtttgacag cttagtgagg tgccatgatc actacctctg      240
cagacattgt ctgaatctgc tgctgtcagt ctccgacaga tgtcccctct gcaaacacca      300
gttgccgacc aaactgaaga tatcgacagc cccaagctca ccacctccct acgaggcgtg      360
a                                                                     361
```

<210> SEQ ID NO 29
<211> LENGTH: 348
<212> TYPE: DNA
<213> ORGANISM: Lymphocytic choriomeningitis virus

<400> SEQUENCE: 29

```
cgtttagttg cgctgtttgg ttgaacagcc ttttcctgtg agagtacaga gacaaaccta      60
gtcattggcc atgggtcaag gcaagtccaa ggagaaaaaa gacaccaaca ccggtgacag     120
agccgagatt ctgccagaca ccacctatct cggtccactg aactgcaaat catgctggca     180
gaagttcgac agtctggtca ggtgccatga ccactacctc tgtagacact gtctgaacct     240
tctgttgtca gtctccgaca ggtgtcctct ttgcaagtgt ccattaccaa ccaagctgaa     300
gatatcaaca gccccaagcc caccacctcc ctacgaagag taacaccg                  348
```

<210> SEQ ID NO 30
<211> LENGTH: 361
<212> TYPE: DNA
<213> ORGANISM: Lymphocytic choriomeningitis virus

<400> SEQUENCE: 30

```
gcggttttga cccctccaat tgacaaagag tcaagcacat ccatcatggg caggtcaaaa      60
tccaaacaaa aagaaaccac tgggcagtgg agggtagatc agagattctc cccgacgcaa     120
cataccttgg cccgctcaac tgcaaaatcc tgctggcaaa gacatgacag cctggtcaag     180
tgtcatgacc actacctgtg tagaaactgt ctaaatcttt tgttgacagt ttcagacagg     240
tgccccctct gcaagcaccc actgcccaca agactgagaa tttcaccagc acccagctcg     300
cctccccct acgaagagta gggaccgaga ggagagcggg ccccagtgg ccacacggac     360
a                                                                      361
```

<210> SEQ ID NO 31
<211> LENGTH: 558
<212> TYPE: PRT
<213> ORGANISM: Lymphocytic choriomeningitis virus

<400> SEQUENCE: 31

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125

Leu Thr Thr Gln Gln Leu Asp Gln Arg Ser Gln Ile Leu Gln Ile Val
    130                 135                 140

Gly Met Arg Lys Pro Gln Gln Gly Ala Ser Gly Val Val Arg Val Trp
145                 150                 155                 160
```

```
Asp Val Lys Asp Ser Ser Leu Leu Asn Asn Gln Phe Gly Thr Met Pro
            165                 170                 175

Ser Leu Thr Met Ala Cys Met Ala Lys Gln Ser Gln Thr Pro Leu Asn
        180                 185                 190

Asp Val Val Gln Ala Leu Thr Asp Leu Gly Leu Leu Tyr Thr Val Lys
        195                 200                 205

Tyr Pro Asn Leu Asn Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Pro Ala Val Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555

<210> SEQ ID NO 32
<211> LENGTH: 558
<212> TYPE: PRT
```

<213> ORGANISM: Lymphocytic choriomeningitis virus

<400> SEQUENCE: 32

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Glu Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Thr Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Asn Asp Leu Glu Arg Leu Arg Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Thr
                325                 330                 335

Glu Lys Pro Val Ala Asn Ser Pro Arg Pro Val Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400
```

```
Gly Gln Phe Ile His Phe Tyr Arg Glu Pro Val Asp Gln Lys Gln Phe
                405                 410                 415

Lys Gln Asp Ser Lys His Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Lys Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Ile His Asn Ile Leu
    530                 535                 540

Pro His Asp Leu Ile Phe Arg Gly Pro Asn Val Val Thr Leu
545                 550                 555

<210> SEQ ID NO 33
<211> LENGTH: 558
<212> TYPE: PRT
<213> ORGANISM: Lymphocytic choriomeningitis virus

<400> SEQUENCE: 33

Met Ser Leu Ser Lys Glu Val Lys Ser Phe Gln Trp Thr Gln Ala Leu
1               5                   10                  15

Arg Arg Glu Leu Gln Asn Phe Thr Thr Asp Val Lys Ala Ala Val Ile
                20                  25                  30

Lys Asp Ala Thr Ser Leu Leu Asn Gly Leu Asp Phe Ser Glu Val Ser
            35                  40                  45

Asn Val Gln Arg Ile Met Arg Lys Glu Lys Arg Asp Asp Lys Asp Leu
        50                  55                  60

Gln Arg Leu Arg Ser Leu Asn Gln Thr Val Tyr Ser Leu Val Asp Leu
65                  70                  75                  80

Lys Ser Ala Ser Lys Lys Asn Val Leu Lys Val Gly Arg Leu Ser Ala
                85                  90                  95

Glu Gln Leu Met Ser Leu Ala Ala Asp Leu Glu Lys Leu Lys Gly Lys
            100                 105                 110

Ile Met Arg Ser Glu Arg Pro Gln Thr Ser Gly Val Tyr Met Gly Ser
        115                 120                 125

Leu Thr Thr Gln Gln Leu Asp Gln Arg Ser Gln Ile Leu Gln Met Val
    130                 135                 140

Gly Met Arg Arg Pro Gln Gln Gly Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Asn Asp Leu Glu Lys Leu Lys Asp Lys His Pro Val
    210                 215                 220
```

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
            245                 250                 255

Gly Gly Asn Met Leu Glu Ser Ile Leu Ile Lys Pro Ser Asn Ser Glu
        260                 265                 270

Asp Leu Leu Lys Ala Val Leu Gly Ala Lys Arg Lys Leu Asn Met Phe
    275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Ser Val Thr Asn Ser Pro Arg Pro Val Pro Gly Ala Ala Gly
            340                 345                 350

Pro Pro Gln Val Gly Leu Ser Tyr Gly Gln Ala Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Thr Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Leu Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Asn Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Val His Asn Ile Leu
    530                 535                 540

Pro His Asp Leu Ile Phe Arg Gly Pro Asn Val Val Thr Leu
545                 550                 555

<210> SEQ ID NO 34
<211> LENGTH: 558
<212> TYPE: PRT
<213> ORGANISM: Lymphocytic choriomeningitis virus

<400> SEQUENCE: 34

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser

```
                35                  40                  45
Asn Val Gln Arg Ile Met Arg Lys Glu Lys Arg Asp Asp Lys Asp Leu
 50                  55                  60

Gln Arg Leu Arg Ser Leu Asn Gln Thr Val Tyr Ser Leu Val Asp Leu
 65                  70                  75                  80

Lys Ser Thr Ser Lys Lys Asn Val Leu Lys Val Gly Arg Leu Ser Ala
                 85                  90                  95

Glu Glu Leu Met Ser Leu Ala Ala Asp Leu Glu Lys Leu Lys Ala Lys
                100                 105                 110

Ile Ile Arg Ser Glu Arg Pro Gln Ala Ser Gly Val Tyr Met Gly Asn
            115                 120                 125

Leu Thr Ala Gln Gln Leu Asp Gln Arg Ser Gln Ile Leu His Met Val
        130                 135                 140

Gly Met Arg Arg Pro Gln Gln Gly Ala Thr Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
                180                 185                 190

Asp Val Gln Ala Leu Thr Asp Leu Gly Leu Leu Tyr Thr Val Lys
            195                 200                 205

Tyr Pro Asn Leu Ser Asp Leu Glu Lys Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Val Lys Lys Lys Leu Asn Met Phe
        275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Ser Asn
                325                 330                 335

Glu Arg Leu Ala Thr Ser Ser Pro Arg Pro Val Pro Gly Ser Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
        370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Thr Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
        450                 455                 460
```

```
Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
            485                 490                 495

Trp Leu Cys Lys Met His Thr Gly Ile Val Lys Asp Lys Lys Lys
        500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Thr Ile His Asn Ile Leu
530                 535                 540

Pro His Asp Leu Ile Phe Arg Gly Pro Asn Val Val Thr Leu
545                 550                 555

<210> SEQ ID NO 35
<211> LENGTH: 558
<212> TYPE: PRT
<213> ORGANISM: Lymphocytic choriomeningitis virus

<400> SEQUENCE: 35

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
50                  55                  60

Gln Arg Leu Arg Ser Leu Asn Gln Thr Val Tyr Ser Leu Val Asp Leu
65                  70                  75                  80

Lys Ser Thr Ser Thr Lys Asn Val Leu Lys Val Gly Arg Leu Ser Ala
                85                  90                  95

Glu Glu Leu Met Ser Leu Ala Ala Asp Leu Glu Lys Leu Lys Thr Lys
            100                 105                 110

Ile Ile Arg Ser Glu Arg Pro Gln Ala Ser Gly Val Tyr Met Gly Asn
        115                 120                 125

Leu Thr Ala Gln Gln Leu Asp Gln Arg Ser Gln Ile Leu His Met Val
130                 135                 140

Gly Met Arg Arg Pro Gln Gln Gly Ala Thr Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Lys Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Val Lys Lys Lys Leu Asn Met Phe
```

```
              275                 280                 285
Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Ser Asn
                325                 330                 335

Glu Arg Leu Ala Thr Ser Pro Arg Pro Val Pro Gly Ser Ala Gly
                340                 345                 350

Pro Pro Gln Val Gly Leu Ser Tyr Ser Gln Thr Met Leu Leu Lys Asp
                355                 360                 365

Leu Met Gly Gly Ile Asp Pro Asn Ala Pro Thr Trp Ile Asp Ile Glu
370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Thr Asp Leu Phe
                420                 425                 430

Asn Ala Gln Pro Gly Leu Thr Ser Ser Val Ile Gly Ala Leu Pro Gln
                435                 440                 445

Gly Met Val Leu Ser Cys Gln Gly Ser Asp Asp Ile Arg Lys Leu Leu
450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Lys Asp Lys Lys Lys
                500                 505                 510

Glu Ile Thr Pro His Cys Ala Leu Met Asp Cys Ile Ile Phe Glu Ser
                515                 520                 525

Ala Ser Lys Ala Arg Leu Pro Asp Leu Lys Thr Ile His Asn Ile Leu
530                 535                 540

Pro His Asp Leu Ile Phe Arg Gly Pro Asn Val Val Thr Leu
545                 550                 555

<210> SEQ ID NO 36
<211> LENGTH: 558
<212> TYPE: PRT
<213> ORGANISM: Lymphocytic choriomeningitis virus

<400> SEQUENCE: 36

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
                20                  25                  30

Lys Asp Ala Thr Ser Leu Leu Asn Gly Leu Asp Phe Ser Glu Val Ser
                35                  40                  45

Asn Val Gln Arg Ile Met Arg Lys Glu Lys Arg Asp Asp Lys Asp Leu
                50                  55                  60

Gln Arg Leu Arg Ser Leu Asn Gln Thr Val Tyr Ser Leu Val Asp Leu
65                  70                  75                  80

Lys Ser Ala Ser Lys Lys Asn Val Leu Lys Val Gly Arg Leu Ser Ala
                85                  90                  95
```

```
Glu Glu Leu Met Ser Leu Ala Ala Asp Leu Glu Lys Leu Lys Ala Lys
                100                 105                 110

Ile Met Arg Ser Glu Arg Pro Gln Ala Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Gly Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Ser Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Arg Pro Met Ala Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Tyr Ile His Phe Tyr Arg Glu Pro Thr Asp Gln Lys Gln Phe
                405                 410                 415

Lys Gln Asp Ser Lys Tyr Ser His Gly Met Asp Leu Val Asp Leu Phe
            420                 425                 430

Asn Ala Gln Pro Gly Leu Thr Ser Ser Val Val Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Lys Asp Lys Lys Lys
            500                 505                 510

Glu Ile Thr Pro His Cys Ala Leu Met Asp Cys Ile Ile Phe Glu Ser
```

```
            515                 520                 525
Ala Thr Lys Ala Arg Leu Pro Asp Leu Lys Thr Val His Asn Ile Leu
        530                 535                 540

Pro His Asp Leu Ile Phe Arg Gly Pro Asn Val Val Thr Leu
545                 550                 555

<210> SEQ ID NO 37
<211> LENGTH: 558
<212> TYPE: PRT
<213> ORGANISM: Lymphocytic choriomeningitis virus

<400> SEQUENCE: 37

Met Ser Leu Ser Lys Glu Ile Lys Ser Phe Gln Trp Thr Gln Ala Leu
1               5                   10                  15

Arg Arg Glu Leu Gln Asn Phe Thr Ser Asp Val Lys Ala Ala Val Ile
            20                  25                  30

Lys Asp Ala Thr Ser Leu Leu Asn Gly Leu Asp Phe Ser Glu Val Ser
                35                  40                  45

Asn Val Gln Arg Ile Met Arg Lys Glu Lys Arg Asp Asp Lys Asp Leu
        50                  55                  60

Gln Arg Leu Arg Ser Leu Asn Gln Thr Val Tyr Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Thr Glu Arg Pro Gln Ala Ser Gly Val Tyr Met Gly Asn
        115                 120                 125

Leu Thr Val Gln Gln Leu Asp Gln Arg Ser Gln Ile Leu Gln Met Val
130                 135                 140

Gly Met Arg Arg Pro Gln Gln Gly Thr Asn Gly Val Val Arg Val Trp
145                 150                 155                 160

Asp Val Arg Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Gly Asp Leu Glu Arg Leu Lys Asp Lys His Pro Val
    210                 215                 220

Leu Gly Val Ile Thr Glu Gln Gln Ser Gly Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Gly Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Asn
                325                 330                 335
```

-continued

Glu Arg Pro Val Ala Asn Leu Pro Arg Pro Ser Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
    370                 375                 380

Gly Arg Ser Asn Asp Pro Val Glu Ile Ala Leu Phe Gln Pro Gln Thr
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Leu Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
        515                 520                 525

Ala Ser Lys Ala Arg Leu Pro Asp Leu Lys Ser Ile His Asn Ile Leu
    530                 535                 540

Pro His Asp Leu Ile Phe Arg Gly Pro Asn Val Val Thr Leu
545                 550                 555

<210> SEQ ID NO 38
<211> LENGTH: 558
<212> TYPE: PRT
<213> ORGANISM: Lymphocytic choriomeningitis virus

<400> SEQUENCE: 38

Met Ser Leu Ser Lys Glu Ile Lys Ser Phe Gln Trp Thr Gln Ala Leu
1               5                   10                  15

Arg Arg Glu Leu Gln Gly Phe Thr Ser Asn Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Asp Arg Arg Asp Asp Lys Asp Leu
    50                  55                  60

Gln Arg Leu Arg Ser Leu Asn Gln Thr Val His Ser Leu Val Glu Leu
65                  70                  75                  80

Lys Ser Thr Ser Lys Lys Asn Ile Leu Lys Val Gly Arg Leu Asn Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125

Leu Thr Thr Gln Gln Leu Asp Gln Arg Ser Gln Ile Leu Gln Met Val
    130                 135                 140

Gly Met Arg Arg Pro Gln Gln Gly Asn Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Ile Ala Lys Gln Ala Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Asp Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Glu Leu Leu Lys Ala Val Leu Gly Ala Lys Arg Lys Phe Asn Met Phe
        275                 280                 285

Val Ser Asp Gln Val Gly Asp Arg Asn Pro Tyr Glu Asn Ile Leu Tyr
    290                 295                 300

Lys Ile Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Ser Gly
                325                 330                 335

Asp Lys Pro Met Thr Asp Leu Pro Arg Pro Ser Pro Gly Ala Ala Gly
            340                 345                 350

Pro Pro Gln Val Gly Leu Ser Tyr Ser Gln Thr Met Leu Leu Lys Asp
        355                 360                 365

Leu Met Ser Gly Ile Asp Pro Asn Ala Pro Thr Trp Ile Asp Ile Glu
    370                 375                 380

Gly Arg Tyr Asn Asp Pro Val Glu Val Ala Ile Phe Gln Pro Gln Asn
385                 390                 395                 400

Gly Gln Phe Ile His Phe Tyr Arg Glu Pro Thr Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
        435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Asn
465                 470                 475                 480

Lys Glu Ala Ser Arg Glu Tyr Glu Asp Lys Val Trp Asp Lys Tyr Gly
                485                 490                 495

Trp Leu Cys Lys Met His Thr Gly Ile Val Lys Asp Lys Lys Lys
            500                 505                 510

Glu Ile Thr Pro His Cys Ala Leu Met Asp Cys Ile Phe Glu Ser
    515                 520                 525

Ala Ser Lys Ala Arg Leu Pro Asp Leu Lys Thr Val His Asn Ile Leu
530                 535                 540

Pro His Asp Leu Val Phe Arg Gly Pro Asn Val Val Thr Leu
545                 550                 555

<210> SEQ ID NO 39
<211> LENGTH: 558

<212> TYPE: PRT
<213> ORGANISM: Lymphocytic choriomening

```
Gly Gln Phe Ile His Phe Tyr Arg Glu Pro Thr Asp Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
                435                 440                 445

Gly Met Val Leu Ser Cys Gln Gly Ser Asp Asp Ile Arg Lys Leu Leu
450                 455                 460

Asp Ser Gln Asn Arg Arg Asp Ile Lys Leu Ile Asp Val Glu Met Asn
465                 470                 475                 480

Lys Glu Ala Ser Arg Glu Tyr Glu Asp Lys Val Trp Asp Lys Tyr Gly
            485                 490                 495

Trp Leu Cys Lys Met His Thr Gly Ile Val Lys Asp Lys Lys Lys
                500                 505                 510

Glu Ile Thr Pro His Cys Ala Leu Met Asp Cys Ile Ile Phe Glu Ser
                515                 520                 525

Ala Ser Lys Ala Arg Leu Pro Asp Leu Lys Thr Val His Asn Ile Leu
530                 535                 540

Pro His Asp Leu Val Phe Arg Gly Pro Asn Val Val Thr Leu
545                 550                 555

<210> SEQ ID NO 40
<211> LENGTH: 558
<212> TYPE: PRT
<213> ORGANISM: Lymphocytic choriomeningitis virus
<220> FEATURE:
<221> NAME/KEY: MOD_RES
<222> LOCATION: (6)..(6)
<223> OTHER INFORMATION: Any amino acid

<400> SEQUENCE: 40

Met Ser Leu Ser Lys Xaa Val Lys Ser Phe Gln Trp Thr Gln Ala Leu
1               5                   10                  15

Arg Arg Glu Leu Gln Gly Phe Thr Ser Asn Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Asp Lys Arg Asp Asp Lys Asp Leu
    50                  55                  60

Gln Arg Leu Arg Ser Leu Asn Gln Thr Val His Ser Leu Val Glu Leu
65                  70                  75                  80

Lys Ser Thr Ser Lys Lys Asn Ile Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Ile Arg Thr Glu Arg Pro Gln Ala Ser Gly Val Tyr Met Gly Asn
        115                 120                 125

Leu Thr Thr Gln Gln Leu Asp Gln Arg Ser Gln Ile Leu Gln Met Val
    130                 135                 140

Gly Met Arg Arg Pro Gln Gln Gly Asn Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190
```

Asp Val Val Gln Ala Leu Thr Asp Leu Gly Leu Leu Tyr Thr Val Lys
                195                 200                 205

Tyr Pro Asn Leu Ser Asp Leu Glu Arg Leu Lys Asp Lys His Pro Val
            210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
            275                 280                 285

Val Ser Asp Gln Val Gly Asp Arg Asn Pro Tyr Glu Asn Ile Leu Tyr
            290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Ser Gly
                325                 330                 335

Asp Lys Leu Ile Thr Asn Thr Pro Arg Pro Thr Pro Gly Ala Ala Gly
            340                 345                 350

Pro Pro Gln Val Gly Leu Ser Tyr Ser Gln Thr Met Leu Leu Lys Asp
            355                 360                 365

Leu Met Ser Gly Ile Asp Pro Asn Ala Pro Thr Trp Ile Asp Ile Glu
            370                 375                 380

Gly Arg Phe Asn Asp Pro Val Glu Val Ala Leu Phe Gln Pro Gln Asn
385                 390                 395                 400

Gly Gln Phe Ile His Phe Tyr Arg Glu Pro Ala Asp Gln Lys Gln Phe
                405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
            435                 440                 445

Gly Met Val Leu Ser Cys Gln Gly Ser Asp Asp Ile Arg Lys Leu Leu
450                 455                 460

Asp Ser Gln Asn Arg Arg Asp Ile Lys Leu Ile Asp Val Glu Met Ser
465                 470                 475                 480

Arg Glu Ala Ser Arg Glu Tyr Glu Asp Lys Val Trp Asp Asn Tyr Gly
                485                 490                 495

Trp Leu Cys Lys Met His Thr Gly Val Val Lys Asp Lys Lys Lys Lys
            500                 505                 510

Glu Ile Thr Pro His Cys Ala Leu Met Asp Cys Ile Ile Phe Glu Ala
            515                 520                 525

Ala Ser Lys Ala Arg Leu Pro Glu Leu Lys Asn Ile His Asn Ile Leu
            530                 535                 540

Pro His Asp Leu Ile Phe Arg Gly Pro Asn Val Val Thr Leu
545                 550                 555

<210> SEQ ID NO 41
<211> LENGTH: 498
<212> TYPE: PRT
<213> ORGANISM: Lymphocytic choriomeningitis virus

<400> SEQUENCE: 41

Met Gly Gln Ile Met Thr Met Phe Glu Ala Leu Pro His Ile Ile Asp
1               5                   10                  15

```
Glu Val Ile Asn Ile Val Ile Val Leu Ile Ile Thr Ser Ile
             20                  25                  30

Lys Ala Val Tyr Asn Phe Ala Thr Cys Gly Ile Phe Ala Leu Val Ser
             35                  40                  45

Phe Leu Leu Leu Ala Gly Arg Ser Cys Gly Met Tyr Gly Leu Asn Gly
 50                      55                  60

Pro Asp Ile Tyr Lys Gly Ile Tyr Gln Phe Lys Ser Val Glu Phe Asp
 65                      70                  75                  80

Met Ser His Leu Asn Leu Thr Met Pro Asn Ala Cys Ser Ala Asn Asn
                     85                  90                  95

Ser His His Tyr Ile Ser Met Gly Ser Ser Gly Leu Glu Leu Thr Phe
                100                 105                 110

Thr Asn Asp Ser Ile Leu Ser His Asn Phe Cys Asn Leu Thr Ser Ala
            115                 120                 125

Phe Asn Lys Lys Thr Phe Asp His Thr Leu Met Ser Ile Val Ser Ser
130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Val Gln Ser Ala Asn Asn Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Ser Glu Asn Pro Asp Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Thr Lys Phe Lys Gln Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Arg Phe Trp Tyr Leu Lys His Ala Lys Thr Gly
    370                 375                 380

Glu Thr Ser Gly Pro Lys Cys Trp Leu Val Thr Asn Gly Ser Tyr Leu
385                 390                 395                 400

Asn Glu Thr His Leu Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430
```

```
Pro Leu Ala Leu Met Asp Ile Leu Met Phe Ser Thr Ser Ala Tyr Leu
            435                 440                 445

Ile Ser Ile Phe Leu His Leu Val Lys Ile Pro Thr His Arg His Ile
450                 455                 460

Lys Gly Gly Ser Cys Pro Lys Pro His Arg Leu Thr Gly Lys Gly Ile
465                 470                 475                 480

Cys Ser Cys Gly Ala Phe Lys Val Pro Gly Val Lys Thr Val Trp Lys
                485                 490                 495

Arg Arg

<210> SEQ ID NO 42
<211> LENGTH: 498
<212> TYPE: PRT
<213> ORGANISM: Lymphocytic choriomeningitis virus

<400> SEQUENCE: 42

Met Gly Gln Ile Val Thr Met Phe Glu Ala Leu Pro His Ile Ile Asp
1               5                   10                  15

Glu Val Ile Asn Ile Val Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Val Asn Asn
            85                  90                  95

Ser His His Tyr Ile Ser Met Gly Ser Ser Gly Leu Glu Pro Thr Phe
        100                 105                 110

Thr Asn Asp Ser Ile Leu Asn His Asn Phe Cys Asn Leu Thr Ser Ala
    115                 120                 125

Leu Asn Lys Lys Ser Phe Asp His Thr Leu Met Ser Ile Val Ser Ser
130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Ser Ser Ser Asp
            165                 170                 175

Pro Gln Ser Ala Met Ser Gln Cys Arg Thr Phe Arg Gly Arg Val Leu
        180                 185                 190

Asp Met Phe Arg Thr Ala Phe Gly Gly Lys Tyr Met Arg Ser Gly Trp
    195                 200                 205

Gly Trp Thr Gly Ser Asp Gly Lys Thr Thr Trp Cys Ser Gln Thr Ser
210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
            245                 250                 255

Thr Lys Phe Leu Thr Arg Arg Leu Ser Gly Thr Phe Thr Trp Thr Leu
        260                 265                 270

Ser Asp Ser Ser Gly Val Glu Asn Pro Gly Gly Tyr Cys Leu Thr Lys
    275                 280                 285

Trp Met Ile Leu Ala Ala Glu Leu Lys Cys Phe Gly Asn Thr Ala Val
290                 295                 300
```

```
Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
            325                 330                 335

Glu Ser Ala Leu His Val Phe Lys Thr Thr Leu Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Phe Val Arg Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg

<210> SEQ ID NO 43
<211> LENGTH: 498
<212> TYPE: PRT
<213> ORGANISM: Lymphocytic choriomeningitis virus

<400> SEQUENCE: 43

Met Gly Gln Ile Val Thr Met Phe Glu Ala Leu Pro His Ile Ile Asp
1               5                   10                  15

Glu Val Ile Asn Ile Val Ile Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175
```

Ala Gln Ser Ala Gln Ser Gln Cys Arg Thr Phe Arg Gly Arg Val Leu
        180             185                 190

Asp Met Phe Arg Thr Ala Phe Gly Gly Lys Tyr Met Arg Ser Gly Trp
            195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Phe Thr Arg Arg Leu Ala Gly Thr Phe Thr Trp Thr Leu
        260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
    290                 295                 300

Ala Lys Cys Asn Val Asn His Asp Ala Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
        340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
        420                 425                 430

Pro Leu Ala Leu Met Asp Leu Leu Met Phe Ser Thr Ser Ala Tyr Leu
            435                 440                 445

Val Ser Ile Phe Leu His Leu Val Lys Ile Pro Thr His Arg His Ile
450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg

<210> SEQ ID NO 44
<211> LENGTH: 498
<212> TYPE: PRT
<213> ORGANISM: Lymphocytic choriomeningitis virus

<400> SEQUENCE: 44

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Leu Ala Thr Cys Gly Ile Phe Ala Leu Val Ser
        35                  40                  45

-continued

```
Phe Leu Leu Leu Ala Gly Arg Ser Cys Gly Met Tyr Gly Leu Ser Gly
         50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Ala Asn Asn
                 85                  90                  95

Ser His His Tyr Ile Ser Met Gly Thr Ser Gly Leu Glu Leu Thr Phe
                100                 105                 110

Thr Asn Asp Ser Ile Ile Asp His Lys Leu Cys Asn Leu Thr Ser Ala
                115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Leu Ser Gln Cys Arg Thr Phe Arg Gly Arg Val Leu
                180                 185                 190

Asp Met Phe Arg Thr Ala Phe Gly Gly Lys Tyr Met Arg Ser Gly Trp
            195                 200                 205

Gly Trp Thr Gly Ser Asp Gly Arg Thr Thr Trp Cys Ser Gln Thr Ser
210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
                260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
            290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Val Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
                420                 425                 430

Pro Leu Ala Leu Met Asp Leu Leu Met Phe Ser Thr Ser Ala Tyr Leu
            435                 440                 445

Ile Ser Val Phe Leu His Leu Met Lys Ile Pro Thr His Arg His Ile
450                 455                 460

Lys Gly Gly Ser Cys Pro Lys Pro His Arg Leu Thr Asn Lys Gly Ile
```

<210> SEQ ID NO 45
<211> LENGTH: 498
<212> TYPE: PRT
<213> ORGANISM: Lymphocytic choriomeningitis virus

<400> SEQUENCE: 45

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Ile Ser
        35                  40                  45

Phe Leu Phe Leu Ala Gly Arg Ser Cys Gly Met Tyr Gly Leu Ser Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Val Asn Asn
                85                  90                  95

Ser His His Tyr Ile Ser Met Gly Thr Ser Gly Leu Glu Leu Thr Phe
            100                 105                 110

Thr Asn Asp Ser Ile Ile Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Lys Ser Ala Leu Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Ile Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Arg
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser

```
                  340                 345                 350
Asp Gln Leu Leu Met Arg Asn His Leu Arg Asp Leu Met Gly Val Pro
            355                 360                 365
Tyr Cys Asn Tyr Ser Lys Phe Trp Tyr Leu Glu His Ala Lys Thr Gly
            370                 375                 380
Glu Thr Ser Val Pro Lys Cys Trp Leu Val Ser Asn Gly Ser Tyr Leu
385                 390                 395                 400
Asn Glu Thr His Phe Ser Asp Gln Ile Glu Gln Glu Ala Asp Asn Met
                405                 410                 415
Ile Thr Glu Met Leu Arg Lys Asp Tyr Ile Lys Arg Gln Gly Ser Thr
                420                 425                 430
Pro Leu Ala Leu Met Asp Leu Leu Met Phe Ser Thr Ser Ala Tyr Leu
            435                 440                 445
Ile Ser Ile Phe Leu His Leu Ile Lys Ile Pro Thr His Arg His Val
            450                 455                 460
Lys Gly Gly Ser Cys Pro Lys Pro His Arg Leu Thr Ser Lys Gly Ile
465                 470                 475                 480
Cys Ser Cys Gly Ala Phe Lys Val Pro Gly Val Lys Thr Ile Trp Lys
                485                 490                 495
Arg Arg

<210> SEQ ID NO 46
<211> LENGTH: 498
<212> TYPE: PRT
<213> ORGANISM: Lymphocytic choriomeningitis virus
<220> FEATURE:
<221> NAME/KEY: MOD_RES
<222> LOCATION: (292)..(292)
<223> OTHER INFORMATION: Any amino acid

<400> SEQUENCE: 46

Met Gly Gln Ile Val Thr Met Phe Glu Ala Leu Pro His Ile Ile Asp
1               5                   10                  15
Glu Val Ile Asn Ile Val Ile Val Leu Ile Ile Ile Thr Ser Ile
                20                  25                  30
Lys Ala Val Tyr Asn Phe Ala Thr Cys Gly Ile Phe Ala Leu Ile Ser
            35                  40                  45
Phe Leu Leu Leu Ala Gly Arg Ser Cys Gly Met Tyr Gly Leu Asp Gly
        50                  55                  60
Pro Asn Ile Tyr Lys Gly Val Tyr Gln Phe Lys Ser Val Glu Phe Asp
65                  70                  75                  80
Met Ser His Leu Asn Leu Thr Met Pro Asn Ala Cys Ser Ala Asn Asn
                85                  90                  95
Ser His His Tyr Ile Ser Met Gly Thr Ser Gly Leu Glu Leu Thr Phe
            100                 105                 110
Thr Asn Asp Ser Ile Ile Ser Asn Lys Pro Cys Asn Leu Ser Ser Ser
            115                 120                 125
Phe Gln Lys Glu Thr Phe Asp His Thr Leu Met Ser Ile Val Thr Ser
        130                 135                 140
Leu His Leu Ser Ile Arg Gly Ser Thr Asn Arg Lys Ala Val Ser Cys
145                 150                 155                 160
Asp Phe Asn Asn Gly Ile Thr Ile Gln Tyr Asn Leu Ser Phe Ser Asp
                165                 170                 175
Ala Gln Ser Ala Leu Ser Gln Cys Arg Thr Phe Arg Gly Arg Val Leu
            180                 185                 190
```

Asp Met Phe Arg Thr Ala Phe Gly Gly Lys Tyr Met Arg Ser Gly Trp
            195                 200                 205

Gly Trp Thr Gly Ser Asp Gly Lys Thr Trp Cys Ser Gln Thr Asn
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Arg Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
            275                 280                 285

Trp Met Ile Xaa Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Arg Thr Gly
    370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
            435                 440                 445

Ile Ser Ile Phe Leu His Leu Val Lys Ile Pro Thr His Arg His Ile
450                 455                 460

Lys Gly Gly Ser Cys Pro Lys Pro His Arg Leu Thr Ser Met Gly Ile
465                 470                 475                 480

Cys Ser Cys Gly Thr Phe Lys Val Pro Gly Val Glu Thr Thr Trp Lys
                485                 490                 495

Arg Arg

<210> SEQ ID NO 47
<211> LENGTH: 498
<212> TYPE: PRT
<213> ORGANISM: Lymphocytic choriomeningitis virus

<400> SEQUENCE: 47

Met Gly Gln Ile Val Thr Met Phe Glu Ala Leu Pro His Ile Ile Asp
1               5                   10                  15

Glu Val Met Asn Ile Val Ile Val Leu Ile Ile Thr Ser Ile
            20                  25                  30

Lys Ala Val Tyr Asn Phe Ala Thr Cys Gly Ile Phe Thr Leu Val Ser
            35                  40                  45

Phe Leu Leu Leu Ala Gly Arg Ser Cys Gly Met Tyr Gly Leu Lys Gly
        50                  55                  60

-continued

```
Pro Asp Ile Tyr Lys Gly Val Tyr Gln Leu Lys Ser Val Glu Phe Asp
 65                  70                  75                  80

Met Ser Tyr Leu Asn Leu Thr Met Pro Asn Ala Cys Ser Ala Asn Asn
                 85                  90                  95

Ser His His Tyr Ile Ser Met Gly Lys Ser Gly Leu Glu Leu Thr Phe
            100                 105                 110

Thr Asn Asp Ser Ile Ile Ser His Asn His Cys Asn Leu Thr Ser Ala
        115                 120                 125

Phe Asn Lys Glu Thr Phe Asp His Thr Leu Met Ser Ile Ile Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Leu Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Asn
    210                 215                 220

Tyr Gln Tyr Leu Ile Ile Gln Asn Arg Thr Trp Asp Asn His Cys Thr
225                 230                 235                 240

Tyr Ala Gly Pro Phe Gly Met Ser Arg Ile Leu Phe Ala Gln Glu Lys
                245                 250                 255

Thr Lys Phe Ile Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Arg
        275                 280                 285

Trp Met Ile Ile Ala Ala Asp Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Arg Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Met His Leu Met Lys Ile Pro Thr His Arg His Ile
    450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Arg Thr Val Trp Lys
```

Arg Arg

<210> SEQ ID NO 48
<211> LENGTH: 498
<212> TYPE: PRT
<213> ORGANISM: Lymphocytic choriomeningitis virus

<400> SEQUENCE: 48

```
Met Gly Gln Ile Val Thr Met Phe Glu Ala Leu Pro His Ile Ile Asp
 1               5                  10                  15
Glu Val Met Asn Ile Val Ile Ile Val Leu Ile Ile Thr Ser Ile
             20                  25                  30
Lys Ala Val Tyr Asn Phe Ala Thr Cys Gly Ile Phe Thr Leu Val Ser
         35                  40                  45
Phe Leu Leu Leu Ala Gly Arg Ser Cys Gly Met Tyr Gly Leu Lys Gly
     50                  55                  60
Pro Asp Ile Tyr Lys Gly Val Tyr Gln Leu Lys Ser Val Glu Phe Asp
 65                  70                  75                  80
Met Ser His Leu Asn Leu Thr Met Pro Asn Ala Cys Ser Ala Asn Asn
                 85                  90                  95
Ser His His Tyr Ile Ser Met Gly Lys Ser Gly Leu Glu Leu Thr Phe
            100                 105                 110
Thr Asn Asp Ser Ile Ile Ser His Asn His Cys Asn Leu Thr Ser Ala
        115                 120                 125
Phe Asn Lys Lys Thr Leu Asp His Thr Leu Met Ser Ile Ile Ser Ser
    130                 135                 140
Leu His Leu Ser Ile Arg Gly Asn Ser Asn Tyr Lys Ala Val Ser Cys
145                 150                 155                 160
Asp Phe Asn Asn Gly Ile Thr Ile Gln Tyr Asn Leu Thr Phe Ser Asp
                165                 170                 175
Ala Gln Ser Ala Leu Ser Gln Cys Arg Thr Phe Arg Gly Arg Val Leu
            180                 185                 190
Asp Met Phe Arg Thr Ala Phe Gly Gly Lys Tyr Met Arg Ser Gly Trp
        195                 200                 205
Gly Trp Thr Gly Ser Asp Gly Lys Thr Thr Trp Cys Ser Gln Thr Asn
    210                 215                 220
Tyr Gln Tyr Leu Ile Ile Gln Asn Arg Thr Trp Asp Asn His Cys Thr
225                 230                 235                 240
Tyr Ala Gly Pro Phe Gly Met Ser Arg Ile Leu Phe Ala Gln Glu Lys
                245                 250                 255
Thr Lys Phe Ile Thr Arg Arg Leu Ala Gly Thr Phe Thr Trp Thr Leu
            260                 265                 270
Ser Asp Ser Ser Gly Val Glu Asn Pro Gly Gly Tyr Cys Leu Thr Arg
        275                 280                 285
Trp Met Ile Ile Ala Ala Asp Leu Lys Cys Phe Gly Asn Thr Ala Val
    290                 295                 300
Ala Lys Cys Asn Val Asn His Asp Glu Glu Phe Cys Asp Met Leu Arg
305                 310                 315                 320
Leu Ile Asp Tyr Asn Lys Ala Ala Leu Thr Lys Phe Lys Glu Asp Val
                325                 330                 335
Glu Ser Ala Leu His Leu Phe Lys Thr Thr Val Asn Ser Leu Ile Ser
            340                 345                 350
Asp Gln Leu Leu Met Arg Asn His Leu Arg Asp Leu Met Gly Val Pro
```

```
                355                 360                 365
Tyr Cys Asn Tyr Ser Lys Phe Trp Tyr Leu Glu His Ala Lys Thr Gly
        370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                    405                 410                 415

Ile Thr Glu Met Leu Arg Lys Asp Tyr Ile Lys Arg Gln Gly Ser Thr
                420                 425                 430

Pro Leu Ala Leu Met Asp Leu Leu Met Phe Ser Thr Ser Ala Tyr Leu
            435                 440                 445

Ile Ser Ile Phe Met His Leu Met Lys Ile Pro Thr His Arg His Ile
        450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Arg Thr Val Trp Lys
                485                 490                 495

Arg Arg

<210> SEQ ID NO 49
<211> LENGTH: 498
<212> TYPE: PRT
<213> ORGANISM: Lymphocytic choriomeningitis virus

<400> SEQUENCE: 49

Met Gly Gln Ile Ile Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Ile Ala Leu Ile Ser
        35                  40                  45

Phe Cys Phe Leu Ala Gly Arg Ser Cys Gly Leu Tyr Gly Val Ser Gly
    50                  55                  60

Ser Asp Ile Tyr Lys Gly Leu Tyr Gln Phe Gln Ser Val Glu Phe Asn
65                  70                  75                  80

Met Ser Gln Leu Asn Leu Thr Met Pro Asn Ala Cys Ser Ala Asn Asn
                85                  90                  95

Ser His His Tyr Ile Ser Met Gly Lys Ser Gly Leu Glu Leu Thr Phe
            100                 105                 110

Thr Asn Asp Ser Ile Ile Gln His Asn Phe Cys Asn Leu Thr Asp Gly
        115                 120                 125

Phe Lys Lys Lys Thr Phe Asp His Thr Leu Met Ser Ile Val Ser Ser
    130                 135                 140

Leu His Leu Ser Ile Arg Gly Asn Thr Ile Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Gly Ala Ile Asn Gln Cys Gly Thr Phe Arg Gly Arg Val Leu
            180                 185                 190

Asp Met Phe Arg Thr Ala Phe Gly Gly Lys Tyr Met Arg Ser Gly Tyr
        195                 200                 205

Gly Trp Lys Asp Ser Asn Gly Lys Thr Thr Trp Cys Ser Gln Thr Asn
    210                 215                 220

Tyr Gln Tyr Leu Ile Ile Gln Asn Arg Thr Trp Glu Asn His Cys Glu
```

```
                225                 230                 235                 240
Tyr Ala Gly Pro Phe Gly Leu Ser Arg Ile Leu Phe Ala Gln Glu Lys
                245                 250                 255

Thr Lys Phe Leu Thr Arg Arg Leu Ala Gly Thr Phe Thr Trp Thr Leu
                260                 265                 270

Ser Asp Ser Ser Gly Thr Glu Thr Pro Gly Gly Tyr Cys Leu Thr Arg
                275                 280                 285

Trp Met Leu Ile Ala Ala Asp Leu Lys Cys Phe Gly Asn Thr Ala Val
                290                 295                 300

Ala Lys Cys Asn Ile Asn His Asp Glu Glu Phe Cys Asp Met Leu Arg
305                 310                 315                 320

Leu Ile Asp Tyr Asn Lys Ala Ala Leu Lys Lys Phe Lys Glu Asp Val
                325                 330                 335

Glu Ser Ala Leu His Leu Phe Lys Thr Thr Val Asn Ser Leu Ile Ser
                340                 345                 350

Asp Gln Leu Leu Met Arg Asn His Leu Arg Asp Leu Met Gly Val Pro
                355                 360                 365

Tyr Cys Asn Tyr Ser Lys Phe Trp Tyr Leu Gln His Val Lys Thr Gly
                370                 375                 380

Glu Met Ser Ala Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
                420                 425                 430

Pro Leu Ala Leu Met Asp Leu Leu Met Phe Ser Thr Ser Ala Tyr Leu
                435                 440                 445

Ile Ser Ile Phe Leu His Leu Met Lys Ile Pro Thr His Arg His Ile
                450                 455                 460

Lys Gly Gly Thr Cys Pro Lys Pro His Arg Leu Thr Ser Lys Gly Ile
465                 470                 475                 480

Cys Ser Cys Gly Ala Phe Arg Val Pro Gly Val Lys Thr Val Trp Lys
                485                 490                 495

Arg Arg

<210> SEQ ID NO 50
<211> LENGTH: 498
<212> TYPE: PRT
<213> ORGANISM: Lymphocytic choriomeningitis virus

<400> SEQUENCE: 50

Met Gly Gln Ile Ile Thr Met Phe Glu Ala Leu Pro His Ile Ile Asp
1               5                   10                  15

Glu Val Ile Asn Ile Val Ile Ile Val Leu Ile Ile Ile Thr Ser Ile
                20                  25                  30

Lys Ala Val Tyr Asn Phe Ala Thr Cys Gly Ile Ile Ala Leu Ile Ser
                35                  40                  45

Phe Cys Phe Leu Ala Gly Arg Ser Cys Gly Leu Tyr Gly Val Ser Gly
                50                  55                  60

Ser Asp Ile Tyr Lys Gly Leu Tyr Gln Phe Gln Ser Val Glu Phe Asn
65                  70                  75                  80

Met Ser Gln Leu Asn Leu Thr Met Pro Asn Ala Cys Ser Ala Asn Asn
                85                  90                  95

Ser His His Tyr Ile Ser Met Gly Lys Ser Gly Leu Glu Leu Thr Phe
```

```
               100                 105                 110
Thr Asn Asp Ser Ile Ile Gln His Asn Phe Cys Asn Leu Thr Asp Gly
            115                 120                 125
Phe Lys Lys Lys Thr Phe Asp His Thr Leu Met Ser Ile Val Ser Ser
            130                 135                 140
Leu His Leu Ser Ile Arg Gly Asn Thr Ile Tyr Lys Ala Val Ser Cys
145                 150                 155                 160
Asp Phe Asn Asn Gly Ile Thr Ile Gln Tyr Asn Leu Thr Phe Ser Asp
                165                 170                 175
Ala Gln Gly Ala Ile Asn Gln Cys Gly Thr Phe Arg Gly Arg Val Leu
            180                 185                 190
Asp Met Phe Arg Thr Ala Phe Gly Gly Lys Tyr Met Arg Ser Gly Tyr
            195                 200                 205
Gly Trp Lys Asp Ser Asn Gly Lys Thr Thr Trp Cys Ser Gln Thr Asn
            210                 215                 220
Tyr Gln Tyr Leu Ile Ile Gln Asn Arg Thr Trp Glu Asn His Cys Glu
225                 230                 235                 240
Tyr Ala Gly Pro Phe Gly Leu Ser Arg Ile Leu Phe Ala Gln Glu Lys
                245                 250                 255
Thr Lys Phe Leu Thr Arg Arg Leu Ala Gly Thr Phe Thr Trp Thr Leu
            260                 265                 270
Ser Asp Ser Ser Gly Thr Glu Thr Pro Gly Gly Tyr Cys Leu Thr Arg
            275                 280                 285
Trp Met Leu Ile Ala Ala Asp Leu Lys Cys Phe Gly Asn Thr Ala Val
            290                 295                 300
Ala Lys Cys Asn Ile Asn His Asp Glu Glu Phe Cys Asp Met Leu Arg
305                 310                 315                 320
Leu Ile Asp Tyr Asn Lys Ala Ala Leu Lys Lys Phe Lys Glu Asp Val
                325                 330                 335
Glu Ser Ala Leu His Leu Phe Lys Thr Thr Val Asn Ser Leu Ile Ser
            340                 345                 350
Asp Gln Leu Leu Met Arg Asn His Leu Arg Asp Leu Met Gly Val Pro
            355                 360                 365
Tyr Cys Asn Tyr Ser Lys Phe Trp Tyr Leu Gln His Val Lys Thr Gly
            370                 375                 380
Glu Met Ser Ala Pro Lys Cys Trp Leu Val Thr Asn Gly Ser Tyr Leu
385                 390                 395                 400
Asn Glu Thr His Phe Ser Asp Gln Ile Glu Gln Glu Ala Asp Asn Met
                405                 410                 415
Ile Thr Glu Met Leu Arg Lys Asp Tyr Ile Lys Arg Gln Gly Ser Thr
            420                 425                 430
Pro Leu Ala Leu Met Asp Leu Leu Met Phe Ser Thr Ser Ala Tyr Leu
            435                 440                 445
Ile Ser Ile Phe Leu His Leu Met Lys Ile Pro Thr His Arg His Ile
            450                 455                 460
Lys Gly Gly Thr Cys Pro Lys Pro His Arg Leu Thr Ser Lys Gly Ile
465                 470                 475                 480
Cys Ser Cys Gly Ala Phe Arg Val Pro Gly Val Lys Thr Val Trp Lys
                485                 490                 495
Arg Arg

<210> SEQ ID NO 51
<211> LENGTH: 504
```

<212> TYPE: PRT
<213> ORGANISM: Lymphocytic choriomeningitis virus

<400> SEQUENCE: 51

```
Met Gly Gln Leu Ile Thr Met Phe Glu Ala Leu Pro His Val Ile Asp
1               5                   10                  15

Glu Val Ile Asn Ile Val Ile Val Leu Val Ile Ile Thr Ser Ile
            20                  25                  30

Lys Ala Val Tyr Asn Phe Ala Thr Cys Gly Ile Ile Ala Leu Ile Ser
        35                  40                  45

Phe Cys Leu Leu Ala Gly Arg Ser Cys Gly Ser Tyr Gly Val Ser Asp
    50                  55                  60

Pro His Ile Phe Lys Gly Leu Tyr His Phe Arg Ser Val Glu Phe Asn
65                  70                  75                  80

Met Ser Gln Leu Asn Leu Thr Met Pro Asn Ala Cys Ser Ala Asn Asn
                85                  90                  95

Ser His His Tyr Ile Ser Met Gly Arg Ser Gly Leu Glu Leu Thr Phe
            100                 105                 110

Thr Asn Asp Ser Ile Leu Gln His Asn Phe Cys Asn Leu Thr Asp Gly
        115                 120                 125

Phe Arg Lys Lys Thr Phe Asp His Thr Leu Met Ser Ile Val Ala Ser
    130                 135                 140

Leu His Leu Ser Ile Arg Gly Asn Thr Asp Tyr Lys Ala Val Ser Cys
145                 150                 155                 160

Asp Phe Asn Asn Gly Ile Thr Ile Gln Tyr Asn Leu Ser Phe Ser Asp
                165                 170                 175

Ala Arg Ser Ala Ile Asn Gln Cys Arg Thr Phe Arg Gly Arg Val Leu
            180                 185                 190

Asp Met Phe Arg Thr Ala Phe Gly Gly Lys Tyr Met Arg Ser Gly Tyr
        195                 200                 205

Gly Trp Lys Asp Ser Asn Gly Lys Ala Thr Trp Cys Ser Gln Thr Asn
    210                 215                 220

Tyr Gln Tyr Leu Ile Ile Gln Asn Arg Thr Trp Glu Asn His Cys Glu
225                 230                 235                 240

Tyr Ala Gly Pro Phe Gly Leu Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Thr Glu Thr Pro Gly Gly Tyr Cys Leu Thr Arg
        275                 280                 285

Trp Met Leu Ile Ala Ala Asp Leu Lys Cys Phe Gly Asn Thr Ala Val
    290                 295                 300

Ala Arg Cys Asn Ile Asn His Asp Glu Glu Phe Cys Asp Met Leu Arg
305                 310                 315                 320

Leu Ile Asp Tyr Asn Lys Ala Ala Leu Lys Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Val Lys Thr Lys
    370                 375                 380

Glu Thr Ser Val Pro Lys Cys Trp Leu Val Thr Asn Gly Ser Tyr Leu
385                 390                 395                 400
```

Asn Glu Thr His Phe Ser Asp Gln Ile Glu Gln Ala Asp Asn Met
            405                 410                 415

Ile Thr Glu Met Leu Arg Lys Asp Tyr Ile Lys Arg Gln Gly Ser Thr
        420                 425                 430

Pro Leu Ala Leu Met Asp Leu Leu Met Phe Ser Thr Ser Ala Tyr Leu
            435                 440                 445

Ile Ser Val Phe Leu His Leu Met Lys Ile Pro Thr His Arg His Ile
    450                 455                 460

Lys Gly Gly Thr Cys Pro Lys Pro His Arg Leu Thr Ser Lys Gly Ile
465                 470                 475                 480

Cys Ser Cys Gly Ala Phe Lys Val Pro Gly Val Lys Thr Val Trp Glu
                485                 490                 495

Ser Gln Gly Gly Pro Gln Trp Val
            500

<210> SEQ ID NO 52
<211> LENGTH: 90
<212> TYPE: PRT
<213> ORGANISM: Lymphocytic choriomeningitis virus

<400> SEQUENCE: 52

Met Gly Gln Gly Lys Ser Lys Glu Lys Lys Asp Thr Asn Thr Gly Asp
1               5                   10                  15

Arg Ala Glu Ile Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Ser Val Ser Asp Arg
    50                  55                  60

Cys Pro Leu Cys Lys Cys Pro Leu Pro Thr Lys Leu Lys Ile Ser Thr
65                  70                  75                  80

Ala Pro Ser Pro Pro Pro Tyr Glu Glu
            85                  90

<210> SEQ ID NO 53
<211> LENGTH: 90
<212> TYPE: PRT
<213> ORGANISM: Lymphocytic choriomeningitis virus

<400> SEQUENCE: 53

Met Gly Gln Gly Lys Ser Lys Glu Glu Arg Asp Thr Ser Asn Thr Gly
1               5                   10                  15

Arg Ala Glu Leu Leu Pro Asp Thr Thr Tyr Leu Gly Pro Leu Asn Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Lys Leu Lys Val Ser Thr
65                  70                  75                  80

Val Pro Ser Ser Leu Pro Pro Tyr Glu Glu
            85                  90

<210> SEQ ID NO 54
<211> LENGTH: 90
<212> TYPE: PRT
<213> ORGANISM: Lymphocytic choriomeningitis virus

<400> SEQUENCE: 54

Met Gly Gln Gly Lys Ser Arg Glu Glu Lys Gly Thr Asn Ser Thr Asn
1               5                   10                  15

Arg Ala Glu Ile Leu Pro Asp Thr Thr Tyr Leu Gly Pro Leu Ser Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys Tyr Pro Leu Pro Thr Arg Leu Lys Ile Ser Thr
65                  70                  75                  80

Ala Pro Ser Ser Pro Pro Tyr Glu Glu
                85                  90

<210> SEQ ID NO 55
<211> LENGTH: 90
<212> TYPE: PRT
<213> ORGANISM: Lymphocytic choriomeningitis virus

<400> SEQUENCE: 55

Met Gly Gln Ser Lys Ser Lys Glu Glu Lys Gly Ile Ser Gly Thr Ser
1               5                   10                  15

Arg Ala Glu Ile Leu Pro Asp Thr Thr Tyr Leu Gly Pro Leu Asn Cys
            20                  25                  30

Lys Ser Cys Trp Gln Lys Phe Asp Ser Leu Val Lys Cys His Asp His
        35                  40                  45

Tyr Leu Cys Arg His Cys Leu Asn Leu Leu Leu Thr Val Ser Asp Arg
    50                  55                  60

Cys Pro Leu Cys Lys Tyr Pro Leu Pro Thr Lys Leu Lys Ile Ser Thr
65                  70                  75                  80

Ala Pro Ser Ser Pro Pro Tyr Glu Glu
                85                  90

<210> SEQ ID NO 56
<211> LENGTH: 90
<212> TYPE: PRT
<213> ORGANISM: Lymphocytic choriomeningitis virus

<400> SEQUENCE: 56

Met Gly Gln Gly Lys Ser Lys Gly Glu Arg Glu Ile Ser Ser Ala Gln
1               5                   10                  15

Arg Ala Glu Ile Leu Pro Asp Thr Thr Tyr Leu Gly Pro Leu Asn Cys
            20                  25                  30

Lys Ser Cys Trp Gln Arg Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys His Gln Leu Pro Thr Lys Leu Lys Ile Ser Thr
65                  70                  75                  80

Ala Pro Ser Ser Pro Pro Tyr Glu Ala
                85                  90

<210> SEQ ID NO 57
<211> LENGTH: 90
<212> TYPE: PRT
<213> ORGANISM: Lymphocytic choriomeningitis virus

```
<400> SEQUENCE: 57

Met Gly Gln Ala Lys Ser Arg Gly Arg Glu Asn Ala Gly Lys Met Asp
1               5                   10                  15

Arg Ala Glu Ile Leu Pro Asp Thr Thr Tyr Leu Gly Pro Leu Asn Cys
            20                  25                  30

Lys Ser Cys Trp Gln Lys Leu Asp Ser Leu Val Arg Cys His Asp His
        35                  40                  45

Tyr Leu Cys Arg Asn Cys Leu Asn Leu Leu Thr Val Ser Asp Arg
50                  55                  60

Cys Pro Leu Cys Lys His Pro Leu Pro Thr Arg Leu Thr Ile Ser Thr
65                  70                  75                  80

Ala Pro Ser Ser Pro Pro Tyr Glu Glu
                85                  90

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gatcagaaac agttcaaaca ggact                                           25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtcccacact ttgtcttcat actct                                           25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaccagtgca gaacttttag aggta                                           25

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcaagtcttc tagtgaggaa ctttg                                           25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 62
cctgtgagag tacagagaca aacct                                         25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gatatcttca gcttggttgg taatg                                         25

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccaaccgcga gaagatga                                                 18

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gatcttcatg aggtagtcag t                                             21

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caaggtcggc agcgagagac atca                                          24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agaaggctag ttgcgtcctt gatg                                          24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 68
ggctgaacat gcattgggca ttgt                                    24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
taggagaagg aagctgacca atgc                                    24

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcctggacac acaactccgg actcta                                  26

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acagccactt ttgtctgcac tgtc                                    24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cttcgtaggg aggtggtggg cttg                                    24

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agttcagtgg accgagatag gtggt                                   25

<210> SEQ ID NO 74
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
50                  55                  60

Glu Trp Val Ala Tyr Ile Ser Ser Gly Ser Thr Leu His Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Lys Leu Pro Ser Leu Cys Tyr Gly Leu Leu
            100                 105                 110

Gly Ser Arg Asn Leu Ser His Arg Leu Leu Ser Gln Asn Asp Thr Pro
        115                 120                 125

Ile Arg Leu Ser Ile Gly Pro Trp Lys Leu Gly Ile
    130                 135                 140

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Asp Ser Arg Leu Asn Leu Val Phe Leu Val Leu Ile Leu Lys Gly
1               5                   10                  15

Val Gln Cys

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Phe Thr Phe Ser Ser Phe Gly Met His Trp Val
1               5                   10

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Ser Ser Gly Ser Ser Thr Leu His Tyr Ala Asp Thr Val Lys Gly
1               5                   10                  15

Arg Phe Thr

<210> SEQ ID NO 78
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 78

His Arg Leu Leu Ser Gln Asn Asp Thr Pro Ile Arg Leu Ser Ile Gly
1               5                   10                  15

Pro

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccgaattcat gtctctgtcc aaggaagtca                                        30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggctcgaggt aaagcagacc aaggtctgtg                                        30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gggaattcct cacagacctt ggtctgcttt                                        30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccctcgagca ctggatcatt gaacctaccc                                        30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccgaattcga gggtaggttc aatgatccag                                        30

<210> SEQ ID NO 84
```

<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cctcgagtta gagtgtcaca acatttggtc                                      30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ccgaattcat gtctctgtcc aaggaagtca                                      30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctcgagtta gagtgtcaca acatttggtc                                      30

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttggatcctg tcaaactttg tcccacacaa ag                                   32

<210> SEQ ID NO 88
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agaattctca tcatctagtg aggaactttg tcttttc                              37

<210> SEQ ID NO 89
<211> LENGTH: 14
<212> TYPE: PRT
<213> ORGANISM: Lymphocytic choriomeningitis virus

<400> SEQUENCE: 89

Arg Ser Gly Trp Gly Trp Ala Gly Ser Asp Gly Lys Thr Thr
1 5 10

<210> SEQ ID NO 90
<211> LENGTH: 140
<212> TYPE: PRT
<213> ORGANISM: Artificial Sequence -continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (126)..(126)
<223> OTHER INFORMATION: Any amino acid

<400> SEQUENCE: 90

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Leu His Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Lys Leu Pro Ser Leu Cys Tyr Gly Leu Leu
            100                 105                 110

Gly Ser Arg Asn Leu Ser His Arg Leu Leu Ser Gln Asn Xaa Thr Pro
        115                 120                 125

Ile Arg Leu Ser Ile Gly Pro Trp Lys Leu Gly Ile
130                 135                 140
```